(12) United States Patent
Behzadi et al.

(10) Patent No.: US 11,026,809 B2
(45) Date of Patent: Jun. 8, 2021

(54) PROSTHESIS INSTALLATION AND ASSEMBLY

(71) Applicant: Kambiz Behzadi, Pleasanton, CA (US)

(72) Inventors: Kambiz Behzadi, Pleasanton, CA (US); Paul Kardel, Greenbrae, CA (US)

(73) Assignee: Kambiz Behzadi, Pleasanton, CA (US)

( * ) Notice: Subject to any disclaimer, the term of this patent is extended or adjusted under 35 U.S.C. 154(b) by 0 days.

(21) Appl. No.: 16/154,033

(22) Filed: Oct. 8, 2018

(65) Prior Publication Data

US 2020/0138598 A1    May 7, 2020

Related U.S. Application Data

(63) Continuation-in-part of application No. 15/716,529, filed on Sep. 27, 2017, which is a continuation-in-part of application No. 15/453,219, filed on Mar. 8, 2017, now Pat. No. 10,426,540, and a continuation-in-part of application No. 15/398,996, filed on Jan. 5, 2017, (Continued)

(51) Int. Cl.
*A61F 2/46*      (2006.01)
*A61F 2/28*      (2006.01)

(52) U.S. Cl.
CPC .......... *A61F 2/4607* (2013.01); *A61F 2/4609* (2013.01); *A61F 2002/2828* (2013.01); *A61F 2002/2832* (2013.01)

(58) Field of Classification Search
CPC .................................................... A61F 2/4607
See application file for complete search history.

(56) References Cited

U.S. PATENT DOCUMENTS

| 1,455,621 A | 5/1923 | Joyner |
| 2,121,193 A | 6/1938 | Erich Hanicke Paul |
| (Continued) | | |

FOREIGN PATENT DOCUMENTS

| EP | 1433445 A1 | 6/2004 |
| WO | 2017029173 A1 | 2/2017 |
| WO | 2018031752 A1 | 2/2018 |

OTHER PUBLICATIONS

International Search Report for International application No. PCT/US2017/012753, dated May 5, 2017.
(Continued)

*Primary Examiner* — Olivia C Chang
(74) *Attorney, Agent, or Firm* — Patent Law Offices Michael E. Woods; Michael E. Woods

(57) ABSTRACT

A system and method for improving installation of a prosthesis, particularly an acetabular cup. The system and method may include implementation of a constant velocity relative motion between a prosthesis and an installation site. For example, an installation system may be fixed relative to the installation site, with the prosthesis fixed into an initial position. The prosthesis is moved at constant speed (i.e., with minimal if any acceleration or applied impulses) relative to the installation site. That is, one or both of the prosthesis or the installation site may be in motion. Resistive forces to installation of a prosthesis may thus be reduced by maintaining the prosthesis constantly in motion relative to the installation site. Securing a processing/implanting tool directly to the installation site may offer advantages.

8 Claims, 42 Drawing Sheets

Related U.S. Application Data now Pat. No. 10,251,663, said application No. 15/453,219 is a continuation-in-part of application No. 15/398,996, filed on Jan. 5, 2017, now Pat. No. 10,251,663, and a continuation-in-part of application No. 15/396,785, filed on Jan. 2, 2017, now Pat. No. 10,653,533, said application No. 15/716,529 is a continuation-in-part of application No. 15/396,785, filed on Jan. 2, 2017, now Pat. No. 10,653,533, which is a continuation-in-part of application No. 15/362,675, filed on Nov. 28, 2016, now Pat. No. 10,660,767, said application No. 15/716,529 is a continuation-in-part of application No. 15/362,675, filed on Nov. 28, 2016, now Pat. No. 10,660,767, said application No. 15/453,219 is a continuation-in-part of application No. 15/362,675, filed on Nov. 28, 2016, now Pat. No. 10,660,767, said application No. 15/398,996 is a continuation-in-part of application No. 15/202,434, filed on Jul. 5, 2016, said application No. 15/716,529 is a continuation-in-part of application No. 15/202,434, filed on Jul. 5, 2016, said application No. 15/362,675 is a continuation-in-part of application No. 15/202,434, filed on Jul. 5, 2016.

(60) Provisional application No. 62/373,515, filed on Aug. 11, 2016, provisional application No. 62/277,294, filed on Jan. 11, 2016.

(56) References Cited

U.S. PATENT DOCUMENTS

| | | | |
|---|---|---|---|
| 3,818,514 | A | 6/1974 | Clark |
| 4,135,517 | A | 1/1979 | Reale |
| 4,457,306 | A | 7/1984 | Borzone |
| 4,530,114 | A | 7/1985 | Tepic |
| 4,712,951 | A | 12/1987 | Brown |
| 5,108,400 | A | 4/1992 | Appel et al. |
| 5,133,765 | A | 7/1992 | Cuilleron |
| 5,318,570 | A | 6/1994 | Hood et al. |
| 5,534,006 | A | 7/1996 | Szabo et al. |
| 5,665,091 | A | 9/1997 | Noble et al. |
| 5,769,092 | A | 6/1998 | Williamson, Jr. |
| 5,806,518 | A | 9/1998 | Mittelstadt |
| 5,849,015 | A | 12/1998 | Haywood et al. |
| 5,980,528 | A | 11/1999 | Salys |
| 6,110,179 | A | 8/2000 | Flivik et al. |
| 6,161,545 | A | 12/2000 | Chow |
| 6,204,592 | B1 | 3/2001 | Hur |
| 6,585,771 | B1 | 7/2003 | Buttermilch et al. |
| 7,036,211 | B1 | 5/2006 | Panks |
| 8,167,823 | B2 | 5/2012 | Nycz et al. |
| 8,603,100 | B2 | 12/2013 | Muller |
| 9,999,518 | B2 | 6/2018 | Mani |
| 10,251,663 | B2 | 4/2019 | Behzadi |
| 10,849,766 | B2 | 12/2020 | Behzadi |
| 2002/0183851 | A1 | 12/2002 | Spiegelberg et al. |
| 2003/0065398 | A1 | 4/2003 | Cueille et al. |
| 2003/0229357 | A1 | 12/2003 | Dye |
| 2004/0097952 | A1 | 5/2004 | Sarin et al. |
| 2005/0101962 | A1 | 5/2005 | Schwenke et al. |
| 2005/0154398 | A1 | 7/2005 | Miniaci et al. |
| 2005/0209597 | A1* | 9/2005 | Long ............. A61F 2/4607 606/86 R |
| 2006/0015110 | A1 | 1/2006 | Pepper |
| 2006/0142754 | A1 | 6/2006 | Irion et al. |
| 2007/0005144 | A1 | 1/2007 | Leisinger et al. |
| 2007/0162038 | A1 | 7/2007 | Tuke |
| 2007/0233131 | A1 | 10/2007 | Song et al. |
| 2008/0109085 | A1* | 5/2008 | Tulkis ............. A61B 17/175 623/22.11 |
| 2009/0192626 | A1 | 7/2009 | Keefer et al. |
| 2010/0023014 | A1 | 1/2010 | Romagnoli et al. |
| 2010/0249796 | A1 | 9/2010 | Nycz |
| 2011/0004318 | A1 | 1/2011 | Tulkis et al. |
| 2011/0178521 | A1 | 7/2011 | Siravo et al. |
| 2011/0264009 | A1 | 10/2011 | Walter et al. |
| 2012/0172939 | A1 | 7/2012 | Pedicini |
| 2012/0209277 | A1 | 8/2012 | Leparmentier et al. |
| 2013/0204264 | A1 | 8/2013 | Mani et al. |
| 2013/0211535 | A1 | 8/2013 | Cueille |
| 2013/0226189 | A1 | 8/2013 | Young |
| 2013/0261762 | A1 | 10/2013 | Kennedy |
| 2014/0135773 | A1 | 5/2014 | Stein et al. |
| 2014/0135791 | A1 | 5/2014 | Nikou et al. |
| 2014/0207123 | A1 | 7/2014 | Mueller |
| 2014/0330281 | A1 | 11/2014 | Aghazadeh |
| 2015/0182350 | A1 | 7/2015 | Behzadi |
| 2015/0182351 | A1 | 7/2015 | Behzadi |
| 2015/0196343 | A1 | 7/2015 | Donald et al. |
| 2015/0201918 | A1 | 7/2015 | Kumar et al. |
| 2015/0282856 | A1 | 10/2015 | Haiat et al. |
| 2016/0166390 | A1 | 6/2016 | Dye et al. |
| 2016/0206430 | A1 | 7/2016 | Grostefon et al. |
| 2016/0206433 | A1 | 7/2016 | Grostefon et al. |
| 2016/0220315 | A1 | 8/2016 | Falardeau et al. |
| 2017/0056205 | A1 | 3/2017 | Biegun et al. |
| 2017/0196506 | A1 | 7/2017 | Behzadi |
| 2017/0196701 | A1 | 7/2017 | Behzadi et al. |
| 2017/0196704 | A1 | 7/2017 | Behzadi et al. |
| 2017/0196705 | A1 | 7/2017 | Behzadi |
| 2017/0196706 | A1 | 7/2017 | Behzadi |
| 2017/0196707 | A1 | 7/2017 | Behzadi |
| 2017/0196708 | A1 | 7/2017 | Behzadi et al. |
| 2017/0196710 | A1 | 7/2017 | Behzadi |
| 2017/0196711 | A1 | 7/2017 | Behzadi |
| 2017/0325972 | A1 | 11/2017 | Steif |
| 2017/0340456 | A1 | 11/2017 | Behzadi |
| 2018/0049891 | A1 | 2/2018 | Termanini |
| 2018/0235764 | A1 | 8/2018 | Moore et al. |
| 2018/0235765 | A1 | 8/2018 | Welker et al. |
| 2018/0296364 | A1 | 10/2018 | Harris et al. |
| 2018/0325695 | A1 | 11/2018 | Wozencroft |
| 2019/0336307 | A1 | 11/2019 | Sungu et al. |

OTHER PUBLICATIONS

Written Opinion of the International Searching Authority for International application No. PCT/US2017/012753 dated May 5, 2017.
International Search Report for International application No. PCT/US2017/046261, dated Oct. 18, 2017.
Written Opinion of the International Searching Authority for International application No. PCT/US2017/046261, dated Oct. 18, 2017.

* cited by examiner

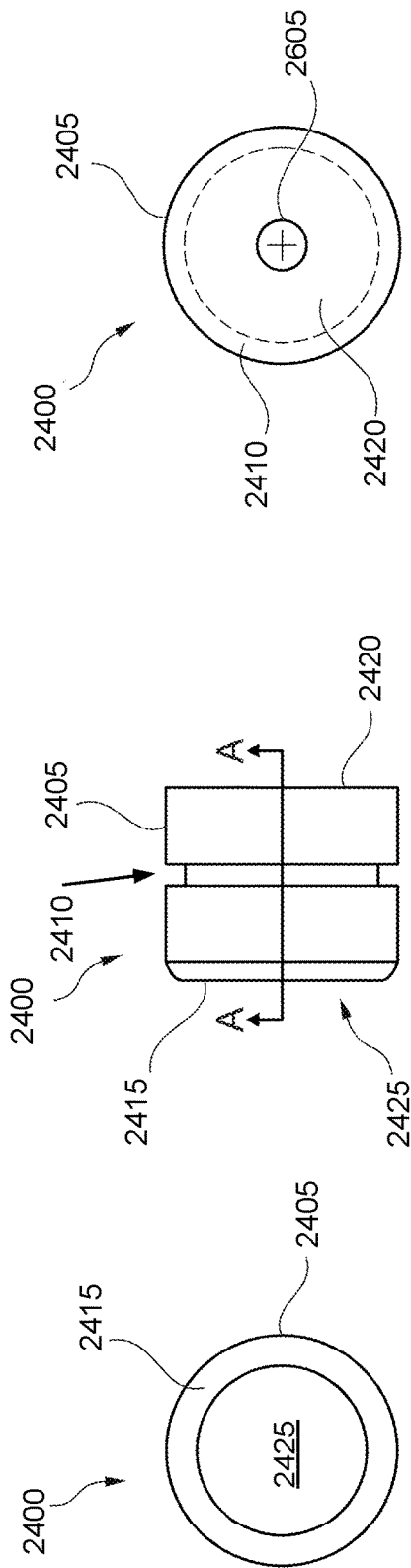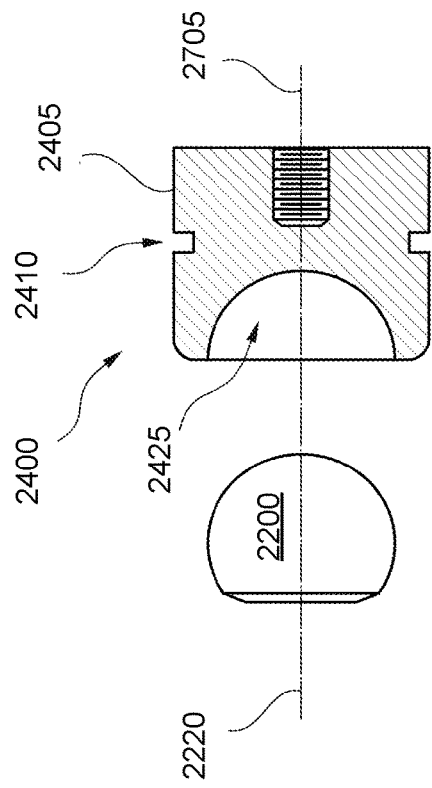

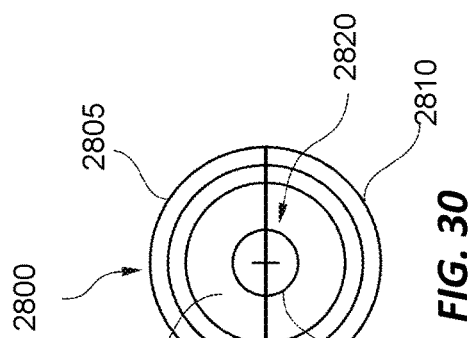
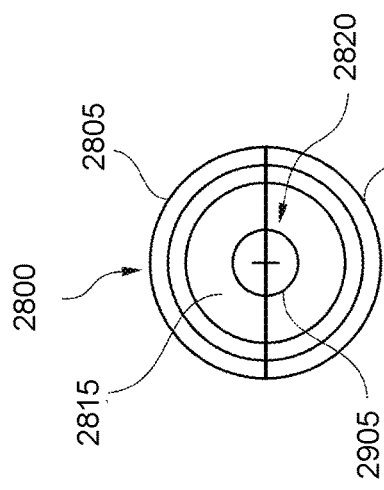
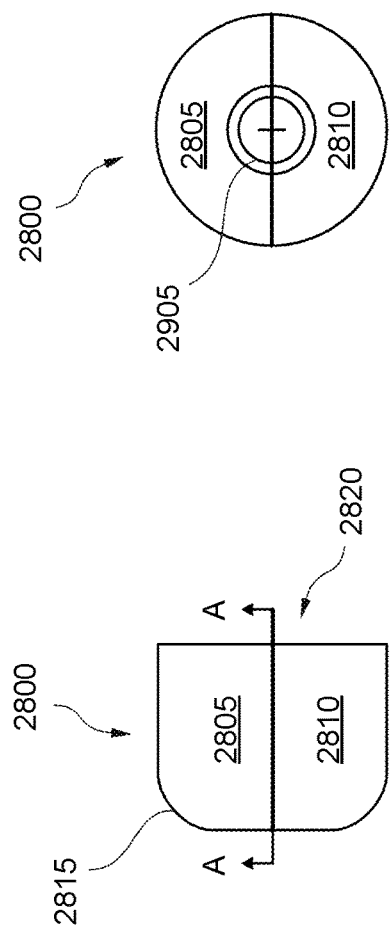
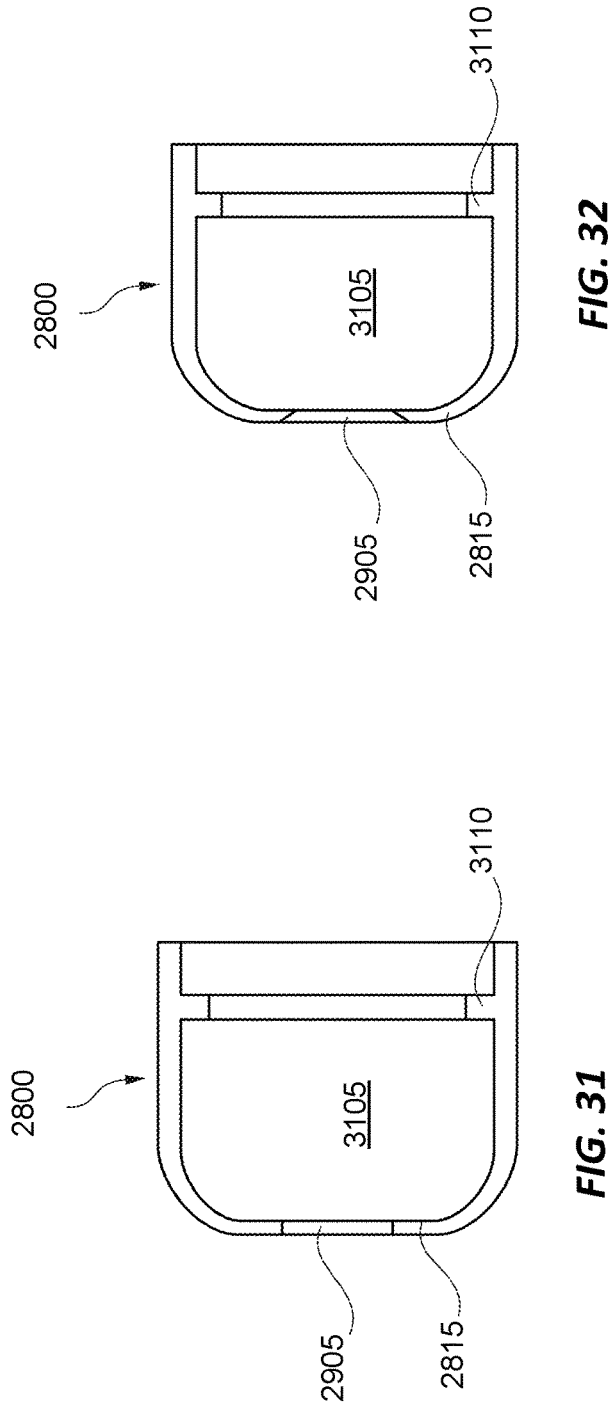

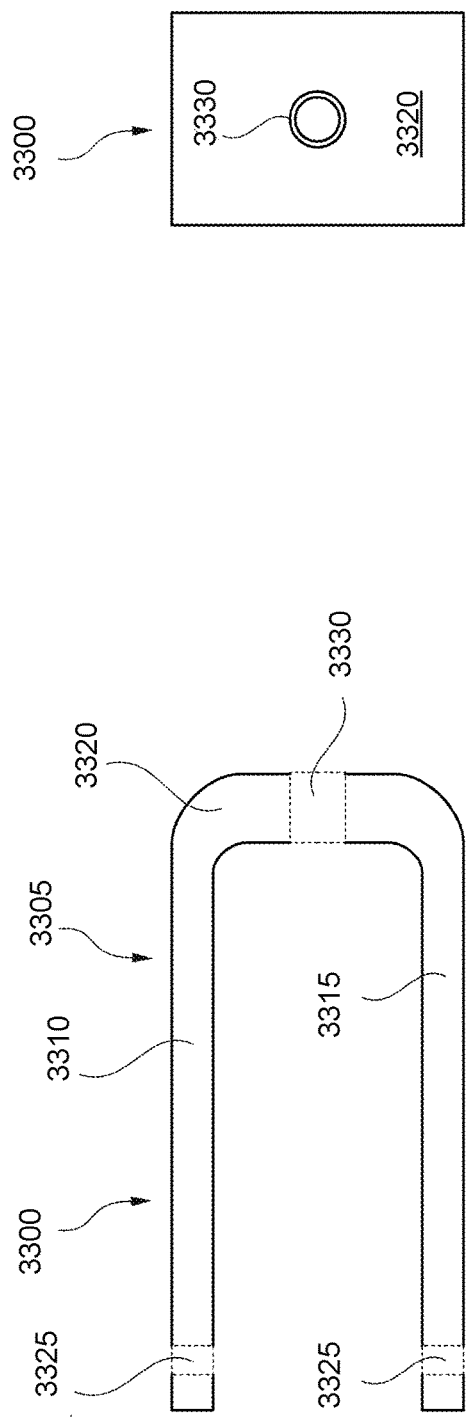
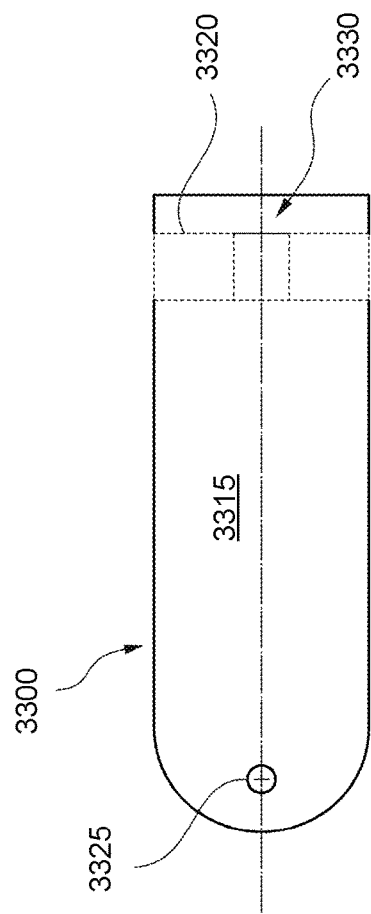
FIG. 33
FIG. 34
FIG. 35

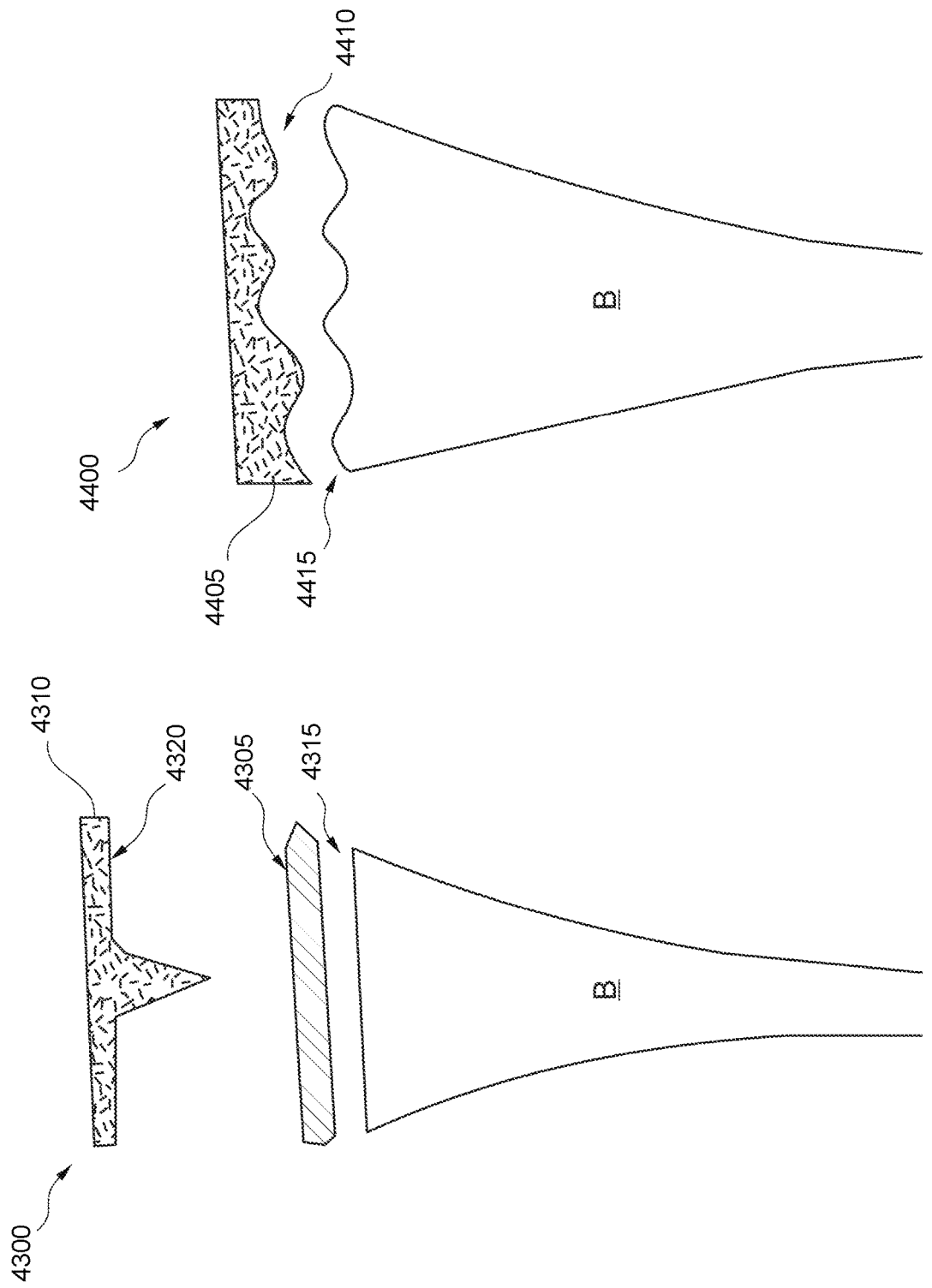

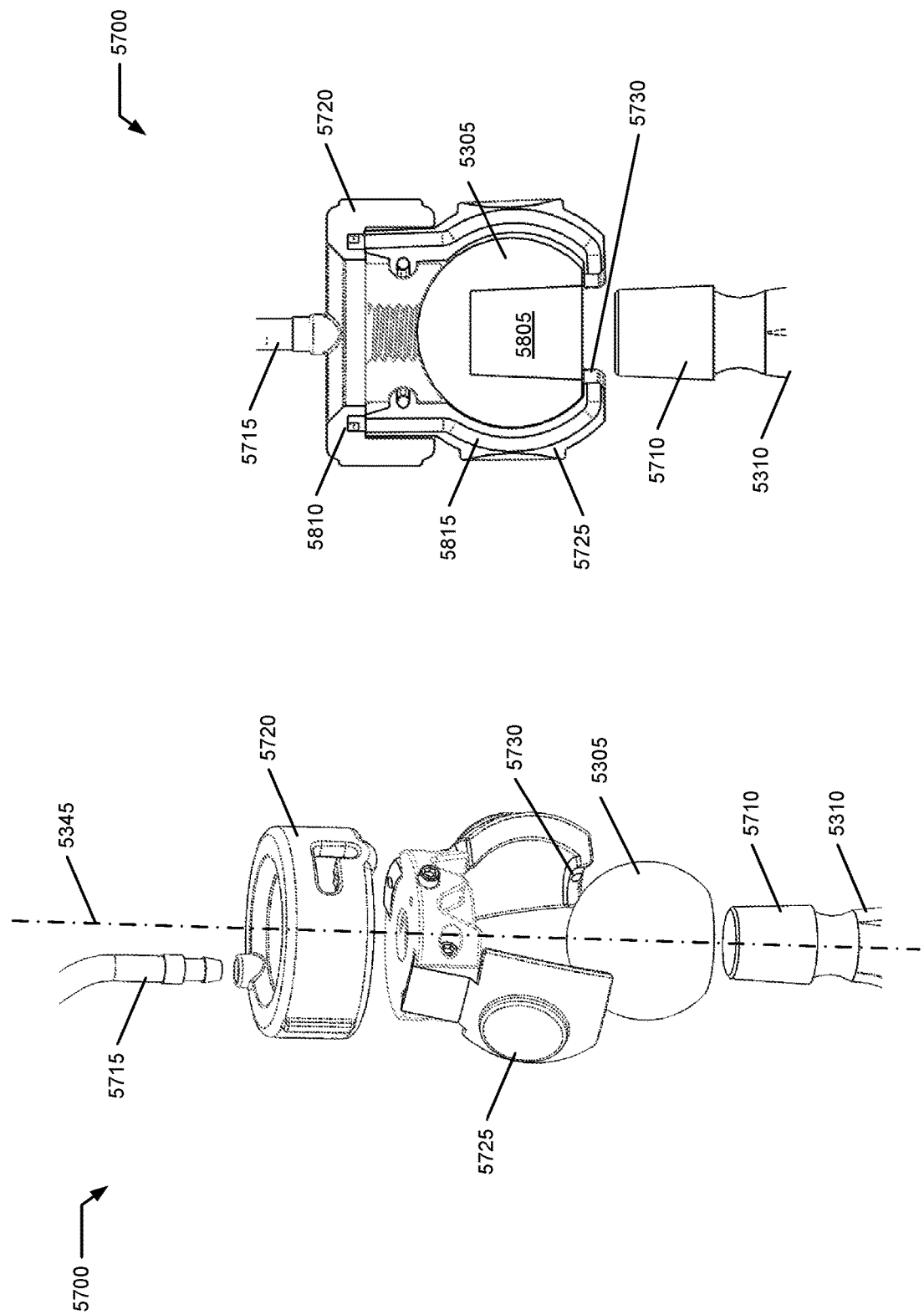

PROSTHESIS INSTALLATION AND ASSEMBLY

CROSS REFERENCE TO RELATED APPLICATIONS

This application is a continuation in part of U.S. patent application Ser. No. 15/716,529 filed 27 Sep. 2017 which is a continuation in part of the following five US Patent Applications Numbers: U.S. application Ser. No. 15/202,434 filed 5 Jul. 2016, U.S. application Ser. No. 15/362,675 filed 28 Nov. 2016, U.S. application Ser. No. 15/396,785 filed 2 Jan. 2017, U.S. application Ser. No. 15/398,996 filed 5 Jan. 2017, and U.S. application Ser. No. 15/453,219 filed 8 Mar. 2017, which in turn variously directly or indirectly claim benefit of one or two provisional patent applications: U.S. Application No. 62/277,294 filed 11 Jan. 2016 and U.S. Application No. 62/373,515 filed 11 Aug. 2016, the contents of which are all hereby expressly incorporated by reference thereto in their entireties for all purposes. This application is also related to U.S. patent application Ser. No. 14/584,656 (now U.S. Pat. No. 9,168,154), the contents of which is hereby expressly incorporated by reference thereto in its entirety for all purposes.

FIELD OF THE INVENTION

The present invention relates generally to installation of a prosthesis, and more specifically, but not exclusively, to non-impactful installation of an acetabular cup into an acetabulum during total hip replacement procedures as well as to improvements in prosthesis placement and positioning.

BACKGROUND OF THE INVENTION

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

Earlier patents issued to the present applicant have described problems associated with prosthesis installation, for example acetabular cup placement in total hip replacement surgery. See U.S. Pat. Nos. 9,168,154 and 9,220,612, which are hereby expressly incorporated by reference thereto in their entireties for all purposes. Even though hip replacement surgery has been one of the most successful operations, it continues to be plagued with a problem of inconsistent acetabular cup placement. Cup mal-positioning is the single greatest cause of hip instability, a major factor in polyethylene wear, osteolysis, impingement, component loosening and the need for hip revision surgery.

The incorporated U.S. Pat. No. 9,168,154, and several of its child applications, detail a concern with conventional installation of a prosthesis in which a surgeon employs a mallet to strike a rod mechanically coupled to the prosthesis. Through a series of discrete, relatively high force strikes, the surgeon drives the prosthesis into the living bone. There are several problems with this solution including non-quantified forces that may fracture the bone at the installation site and/or may not properly seat the prosthesis within the bone.

There are several applications in the family of the incorporated US Patent Applications that detail various Behzadi Medical Devices for decreasing or minimizing impactful strikes and for improving installation of a prosthesis, particularly an acetabular cup.

Earlier patents issued to the present applicant have described problems associated with prosthesis installation, for example acetabular cup placement in total hip replacement surgery. See U.S. Pat. Nos. 9,168,154 and 9,220,612, which are hereby expressly incorporated by reference thereto in their entireties for all purposes. Even though hip replacement surgery has been one of the most successful operations, it continues to be plagued with a problem of inconsistent acetabular cup placement. Cup mal-positioning is the single greatest cause of hip instability, a major factor in polyethylene wear, osteolysis, impingement, component loosening and the need for hip revision surgery.

These incorporated patents explain that the process of cup implantation with a mallet is highly unreliable and a significant cause of this inconsistency. The patents note two specific problems associated with the use of the mallet. First is the fact that the surgeon is unable to consistently hit on the center point of the impaction plate, which causes undesirable torques and moment arms, leading to mal-alignment of the cup. Second, is the fact that the amount of force utilized in this process is non-standardized.

In these patents there is presented a new apparatus and method of cup insertion which uses an oscillatory motion to insert the prosthesis. Prototypes have been developed and continue to be refined, and illustrate that vibratory force may allow insertion of the prosthesis with less force, as well, in some embodiments, of allowing simultaneous positioning and alignment of the implant.

There are other ways of breaking down the large undesirable, torque-producing forces associated with the discrete blows of the mallet into a series of smaller, axially aligned controlled taps, which may achieve the same result incrementally, and in a stepwise fashion to those set forth in the incorporated patents, (with regard to, for example, cup insertion without unintended divergence).

There are two problems that may be considered independently, though some solutions may address both in a single solution. These problems include i) undesirable and unpredictable torques and moment arms that are related to the primitive method currently used by surgeons, which involves manually banging the mallet on an impaction plate mated to the prosthesis and ii) non-standardized and essentially uncontrolled and unquantized amounts of force utilized in these processes. These unpredictable torqueing forces may also be present in assembly of modular prosthetic systems, especially those that employ a mallet to strike one component onto another component during assembly.

Some of these procedures, including a manual non-quantized unpredictable striking of an element of an implant with a mallet are present in other situations such as assembly of a modular prosthesis. In addition to some of the related problems described herein, mallet-struck prosthesis assembly may be associated with various physiologic problems (e.g., trunnionosis) which may limit use of surgeon-assembled modular prosthesis systems.

BRIEF SUMMARY OF THE INVENTION

Disclosed is a system and method for improving assembly of a prosthesis. The following summary of the invention is provided to facilitate an understanding of some of the technical features related to assembly of a prosthesis, particularly installation of a head on a trunnion neck, and is not intended to be a full description of the present invention. A full appreciation of the various aspects of the invention can be gained by taking the entire specification, claims, drawings, and abstract as a whole. The present invention is applicable to other prosthesis and to assembly of modular prosthesis and systems intended for installation into a living body.

Further disclosed is a system and method for improving assembly, preparation, and installation of a prosthesis. The following summary of the invention is provided to facilitate an understanding of some of the technical features related to prosthesis assembly and installation, and is not intended to be a full description of the present invention. A full appreciation of the various aspects of the invention can be gained by taking the entire specification, claims, drawings, and abstract as a whole. The present invention is applicable to other prosthesis in addition to acetabular cups, other modular prosthesis in addition to assembly of modular femoral and humeral prosthesis, and to other alignment and navigation systems in addition to referenced light guides.

An embodiment of the present invention may include implementation of a constant velocity relative motion between a prosthesis and an installation site. For example, an installation system may be fixed relative to the installation site, with the prosthesis fixed into an initial position. The prosthesis is moved at constant speed (i.e., with minimal if any acceleration or applied impulses) relative to the installation site. That is, one or both of the prosthesis or the installation site may be in motion. For example, a hip may be fixed in place on an operating platform and the installation tool secured to the platform and/or to the hip. The tool is advanced toward the hip to insert the prosthesis into the installation site. Alternatively, or in addition, the hip may be moved toward the installation tool, such as by fixing the installation tool above the operating platform and then elevating the platform at a constant speed. In some applications, the installation tool may be part of a robotic tool to help provide accurate orientation during installation.

In an embodiment, it may be desirable to reduce forces that are resistive to the constant speed/velocity insertion. For example, as detailed in U.S. Patent Application No. 62/319,377 filed 7 Apr. 2016 and its non-provisional conversion U.S. patent application Ser. No. 15/234,927 filed 11 Aug. 2016 and a continuation-in-part thereof, U.S. patent application Ser. No. 15/406,752 filed 15 Jan. 2017, the contents of these applications are hereby expressly incorporated by reference thereto in their entireties for all purposes, a surface modification or a surface treatment of the surface of the prosthesis engaging the installation site may further reduce the resistive forces. The surface treatment may vary, for example, and include unidirectional surface elements for biasing the installation or use of a paste, cream, slurry, and/or ice to provide a low resistive film.

An embodiment of the present invention may include axial alignment of force transference, such as, for example, an axially sliding hammer moving between stops to impart a non-torqueing installation force. There are various ways of motivating and controlling the sliding hammer, including a magnitude of transferred force. Optional enhancements may include pressure and/or sound sensors for gauging when a desired depth of implantation has occurred.

Other embodiments include adaptation of various devices for accurate assembly of modular prostheses, such as those that include a head accurately impacted onto a trunnion taper that is part of a stem or other element of the prosthesis.

Still other embodiments include an alignment system to improve site preparation, such as, for example, including a projected visual reference of a desired orientation of a tool and then having that reference marked and available for use during operation of the tool to ensure that the alignment remains proper throughout its use, such as during a reaming operation.

Further embodiments include enhancement of various tools, such as those used for cutting, trimming, drilling, and the like, with ultrasonic enhancement to make the device a better cutting, trimming, drilling, etc. device to enable its use with less strength and with improved accuracy.

An embodiment of the present invention may include a grip structure on a body of modular assembly that may provide an anchor for defining an alignment axis for a trunnion of the body and a head to be installed onto the trunnion.

An embodiment of the present invention may include a head grasper that secures the head into an optimized assembly position relative to the alignment axis/trunnion. The optimized assembly position may include non-relative canting and alignment with the alignment axis.

An embodiment of the present invention may include a holder that engages a grip structure and is coupled to a head grasper. The holder may aid in reducing waste of energy used in assembly of the head onto the trunnion and it may aid in the optimized positioning of the head relative to the alignment axis/trunnion before and/or during installation of the head onto the trunnion.

An embodiment of the present invention may include use of force source coupled to a head grasper/tool to generate assembly forces to install the head onto the trunnion. The force source may deliver one or more of a dynamic assembly force, a vibratory assembly force, a set of discrete assembly impacts, other assembly forces, and combinations thereof. The assembly force(s) may be applied the head grasper/tool to install the head onto the trunnion. The assembly force(s) may be constrained to operate along the alignment axis, and may be reduced by securing/anchoring the body of the modular prosthesis, such as by using a grip structure.

An embodiment of the present invention may include use of a force sensing mechanism coupled to a head grasper/tool to measure, possibly in true realtime (e.g., during dynamic operation of the tool to apply the assembly force(s)), the assembly force(s).

An embodiment of the present invention may include development and production of standards, guidelines, recommendations for an optimum force, or force range for the assembly force(s) to achieve a desired cold weld.

An apparatus for acting on a portion of bone, including a force transfer anchor fixed to the portion of bone, the force transfer anchor including a tool mount; and a tool, coupled to the tool mount, including an operational end configured to interface with the portion of bone using an interface force; wherein a portion of the interface force is transferred between the portion of bone and the tool through the force transfer anchor.

A method for acting on a portion of bone, including a) fixing a force transfer anchor to the portion of bone, the force transfer anchor including a tool mount; b) interfacing a tool, coupled to the tool mount and with the tool including an operational end, with the portion of bone using an interface force; c) transferring a portion of the interface force between the portion of bone and the tool through the force transfer anchor.

A modular prosthesis body, including a stem portion; a trunnion portion coupled to the stem portion, the trunnion portion having an insertion profile defining an insertion axis and further defining a pair of opposing side faces including a first side face and a second side face; a first grip structure coupled to the first side face and disposed on the insertion axis; and a second grip structure coupled to the second side face and disposed on the insertion axis.

A system for assembly of a modular prosthesis including a stem portion, a trunnion portion coupled to the stem portion, the trunnion portion having an insertion profile defining an insertion axis and a pair of opposing side faces defining a non-planar grip structure, and a prosthesis head configured to be installed on the trunnion portion and defining an installation aperture complementary to the insertion profile with the installation aperture defining an installation axis, including a head grasper including a housing defining a cavity complementary to an outer portion of the prosthesis head with the housing having a grasper axis extending through the cavity wherein the housing is configured to secure the prosthesis head within the cavity and align the grasper axis with the installation axis; wherein the head grasper includes a pair of mating engagement structures, complementary to the grip structures, for non-rotatingly securement of the head grasper to the trunnion portion.

An embodiment of the present invention may include a system having a portion of a living bone of a patient or other foundation, a tool for acting upon that portion of bone or foundation, and a force transfer anchor that secures, constrains, and/or fixes a known relative relationship between the tool and the portion of bone or foundation. A wide range of tools may be used for acting directly or indirectly on the portion of bone (e.g., milling, subtracting, or removing or adding bone, bone material, and/or foundation material, installing an implant, repositioning an implant, and the like). The tools may operate with many different force modes relative to the portion of bone/foundation (e.g., constant force, vibratory force, and/or a series of discrete impacts). The anchor, a controller, and/or the tool may be provided with a set of sensors for collecting and/or assessing a set of parameters. In some implementations, the anchor helps to reduce wasting energy applied at an interface between the tool and the portion of bone. The anchor may aid in force transfer in some cases. An implementation of the anchor may include essentially a passive static structure. In other instances, the anchor may include dynamic adjustable elements. An embodiment of the present invention may include a substitute for a surgical robot or other robotic system by providing a smart three-dimensional processing tool that may include relativistic navigational and force sensing elements to reference processings to the patient and become relatively free of an absolute reference system calibrated to a space or environment, such as a particular operating room. For example, use of inertial measurement units and force sensors may allow for an embodiment that is simple and efficient.

A modular prosthesis body, including a stem portion; a trunnion portion coupled to the stem portion, the trunnion portion having an insertion profile defining an insertion axis and further defining a pair of opposing side faces including a first side face and a second side face; a first grip structure coupled to the first side face and disposed on the insertion axis; and a second grip structure coupled to the second side face and disposed on the insertion axis.

A system for assembly of a modular prosthesis including a stem portion, a trunnion portion coupled to the stem portion, the trunnion portion having an insertion profile defining an insertion axis and a pair of opposing side faces defining a non-planar grip structure, and a prosthesis head configured to be installed on the trunnion portion and defining an installation aperture complementary to the insertion profile with the installation aperture defining an installation axis, including a head grasper including a housing defining a cavity complementary to an outer portion of the prosthesis head with the housing having a grasper axis extending through the cavity wherein the housing is configured to secure the prosthesis head within the cavity and align the grasper axis with the installation axis; wherein the head grasper includes a pair of mating engagement structures, complementary to the grip structures, for non-rotatingly securement of the head grasper to the trunnion portion.

An apparatus for assembly of a modular prosthesis including a stem portion, a trunnion portion coupled to the stem portion, the trunnion portion having an insertion profile defining an insertion axis and a pair of opposing side faces defining a non-planar grip structure, and a prosthesis head configured to be installed on the trunnion portion and defining an installation aperture complementary to the insertion profile with the installation aperture defining an installation axis, including a clamp including a pair of mating engagement structures, complementary to the grip structures, for non-rotatingly securement of the prosthesis head to the trunnion portion, the clamp including a force applicator configured to apply a relative assembly force between the trunnion portion and to the prosthesis head to install the prosthesis head on the trunnion portion wherein the clamp aligns the axes and wherein the relative assembly force is constrained by the clamp to be coaxial with the axes.

Any of the embodiments described herein may be used alone or together with one another in any combination. Inventions encompassed within this specification may also include embodiments that are only partially mentioned or alluded to or are not mentioned or alluded to at all in this brief summary or in the abstract. Although various embodiments of the invention may have been motivated by various deficiencies with the prior art, which may be discussed or alluded to in one or more places in the specification, the embodiments of the invention do not necessarily address any of these deficiencies. In other words, different embodiments of the invention may address different deficiencies that may be discussed in the specification. Some embodiments may only partially address some deficiencies or just one deficiency that may be discussed in the specification, and some embodiments may not address any of these deficiencies.

Other features, benefits, and advantages of the present invention will be apparent upon a review of the present disclosure, including the specification, drawings, and claims.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

FIG. 1 illustrates an initial orientation of the installation system and the installation site;

FIG. 2 illustrates a first period after an initiation of a constant velocity installation process;

FIG. 3 illustrates a second period after the initiation of the constant velocity installation process;

FIG. 4 illustrates a third period after Initiation of the constant velocity installation process in which the prosthesis has been installed without meaningful acceleration or impacts;

FIG. 5 illustrates an embodiment of the present invention for a sliding impact device;

FIG. 6 illustrates a lengthwise cross-section of the embodiment illustrated in FIG. 5 including an attachment of a navigation device;

FIG. 7 illustrates a cockup mechanical gun embodiment, an alternative embodiment to the sliding impact device illustrated in FIG. 5 and FIG. 6;

FIG. 8 illustrates an alternative embodiment to the devices of FIG. 5-7 including a robotic structure;

FIG. 9 illustrates an alternative embodiment to the devices of FIG. 5-8 including a pressure sensor to provide feedback;

FIG. 10 illustrates an alternative embodiment to the feedback system of FIG. 9 including a sound sensor to provide feedback for the embodiments of FIG. 5-9;

FIG. 11 illustrates a modular prosthesis and assembly tools;

FIG. 12 illustrates a femoral head to be assembled onto a trunnion attached to a femoral stem;

FIG. 13 illustrates alignment of an installation device with the femoral head for properly aligned impaction onto the trunnion, such as an embodiment of FIG. 1-FIG. 6 adapted for this application;

FIG. 14 illustrates use of a modified vibratory system for assembly of the modular prosthesis;

FIG. 15 illustrates an environment in which a prosthesis is installed highlighting problem with site preparation;

FIG. 16 illustrates an alignment system for preparation and installation of a prosthesis;

FIG. 21 through FIG. 37 illustrate a particular implementation of a mechanical alignment system for use with an embodiment of a BMD5 tool;

FIG. 21 illustrates a side view of a prosthetic body to be mechanically joined to an installable prosthetic head;

FIG. 22 and FIG. 23 illustrate a set of views of a prosthetic head to be installed on the prosthetic body of FIG. 21;

FIG. 22 illustrates a top view of the prosthetic head;

FIG. 23 illustrates a side view of the prosthetic head;

FIG. 24 through FIG. 27 illustrate a set of views for an anvil for imparting an assembly force to the prosthetic head;

FIG. 24 illustrates a side view of the anvil;

FIG. 25 illustrates a top view of the anvil;

FIG. 26 illustrates a bottom view of the anvil; and

FIG. 27 illustrates a sectional view through the anvil;

FIG. 28 through FIG. 32 illustrate a set of views of a two-part clamp for securing the anvil to the prosthetic head;

FIG. 28 illustrates a side view of the two-part clamp;

FIG. 29 illustrates a top view of the two-part clamp;

FIG. 30 illustrates a bottom view of the two-part clamp;

FIG. 31 illustrates a sectional view through the two-part clamp; and

FIG. 32 illustrates an enlarged view of FIG. 31;

FIG. 33 through FIG. 35 illustrate a set of views of a clamp for attachment to the prosthetic body and apply an aligned assembly force to the prosthetic head by use of the two-part clamp;

FIG. 33 illustrates a top view of the clamp;

FIG. 34 illustrates an end view of the clamp; and

FIG. 35 illustrates a side view of the clamp;

FIG. 36 illustrates a stackup view for the mechanical alignment system shown securing, aligning, and applying an assembly force to the prosthetic head to install it onto the prosthetic body;

FIG. 37 illustrates a representative manual torque wrench which may be used with the system illustrated in FIG. 36 to apply a predetermined assembly force to produce a desired mechanical join of the prosthetic head onto the prosthetic body;

FIG. 39 illustrates a perspective view of a powered bone saw;

FIG. 40 illustrates a broach attachment for a powered reciprocating bone preparation tool;

FIG. 41 illustrates a hand-operated reamer; and

FIG. 42 illustrates a set of bone preparation burrs;

FIG. 43 illustrates a side view of a first set of components for a conventional bone preparation process;

FIG. 44 illustrates a side view of a second set of components for a three-dimensional bone sculpting process that may be enabled by some embodiments of the present invention;

FIG. 46 illustrates a side view of an alternative prosthetic body to be mechanically joined to an installable prosthetic head;

FIG. 47 illustrates a top view of the alternative prosthetic body of FIG. 46;

FIG. 48 illustrates an enlarged front view of the alternative prosthetic body of FIG. 46; and FIG. 49 illustrates an alternative clamping system for use with the alternative prosthetic body of FIG. 46;

FIG. 50 illustrates a generic fluid injection system for use with a modular assembly system;

FIG. 51 illustrates a fluid jet system directing a fluid into a cavity of the installable prosthetic head;

FIG. 52 illustrates an alternative fluid jet system for directing a fluid into a cavity of the installable prosthetic head;

FIG. 57 illustrates a detailed view of an addition of a fluid system to the trunnion head system illustrated in FIG. 55; and FIG. 58 illustrates a detailed view of the addition of the fluid system to the trunnion head system illustrated in FIG. 56.

DETAILED DESCRIPTION OF THE INVENTION

Figure 1:
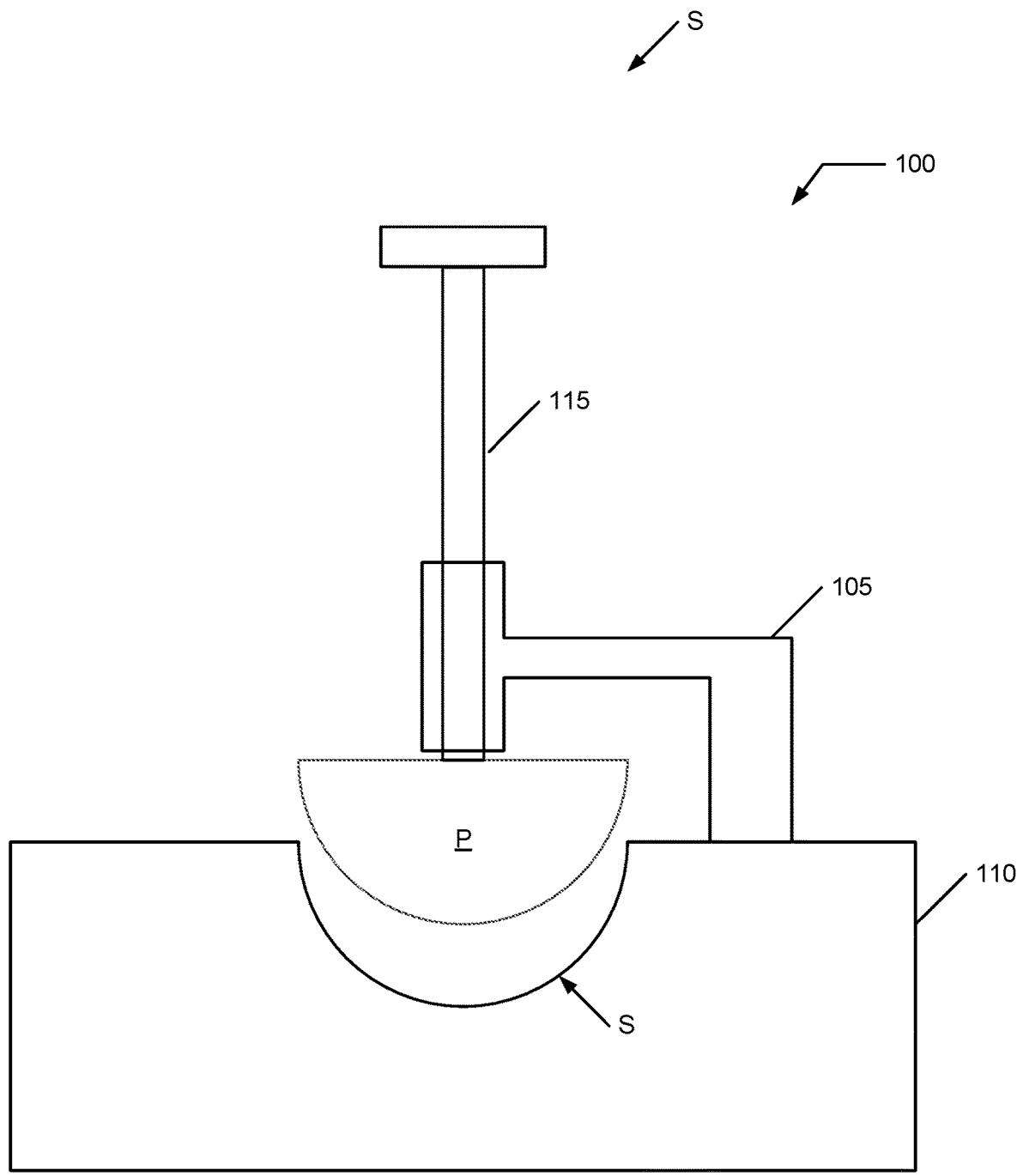
FIG. 1-FIG. 4 illustrate a time-lapse series of constant velocity relative motion between a prosthesis engaged by an installation system and an installation site for the prosthesis.

Embodiments of the present invention provide a system and method for improving installation of a prosthesis, particularly an acetabular cup. The following description is presented to enable one of ordinary skill in the art to make and use the invention and is provided in the context of a patent application and its requirements.

Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

Definitions

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The following definitions apply to some of the aspects described with respect to some embodiments of the invention. These definitions may likewise be expanded upon herein.

As used herein, the term "or" includes "and/or" and the term "and/or" includes any and all combinations of one or more of the associated listed items. Expressions such as "at least one of," when preceding a list of elements, modify the entire list of elements and do not modify the individual elements of the list.

As used herein, the singular terms "a," "an," and "the" include plural referents unless the context clearly dictates otherwise. Thus, for example, reference to an object can include multiple objects unless the context clearly dictates otherwise.

Also, as used in the description herein and throughout the claims that follow, the meaning of "in" includes "in" and "on" unless the context clearly dictates otherwise. It will be understood that when an element is referred to as being "on" another element, it can be directly on the other element or intervening elements may be present therebetween. In contrast, when an element is referred to as being "directly on" another element, there are no intervening elements present.

As used herein, the term "set" refers to a collection of one or more objects. Thus, for example, a set of objects can include a single object or multiple objects. Objects of a set also can be referred to as members of the set. Objects of a set can be the same or different. In some instances, objects of a set can share one or more common properties.

As used herein, the term "adjacent" refers to being near or adjoining. Adjacent objects can be spaced apart from one another or can be in actual or direct contact with one another. In some instances, adjacent objects can be coupled to one another or can be formed integrally with one another.

As used herein, the terms "connect," "connected," and "connecting" refer to a direct attachment or link. Connected objects have no or no substantial intermediary object or set of objects, as the context indicates.

As used herein, the terms "couple," "coupled," and "coupling" refer to an operational connection or linking. Coupled objects can be directly connected to one another or can be indirectly connected to one another, such as via an intermediary set of objects.

The use of the term "about" applies to all numeric values, whether or not explicitly indicated. This term generally refers to a range of numbers that one of ordinary skill in the art would consider as a reasonable amount of deviation to the recited numeric values (i.e., having the equivalent function or result). For example, this term can be construed as including a deviation of ±10 percent of the given numeric value provided such a deviation does not alter the end function or result of the value. Therefore, a value of about 1% can be construed to be a range from 0.9% to 1.1%.

As used herein, the terms "substantially" and "substantial" refer to a considerable degree or extent. When used in conjunction with an event or circumstance, the terms can refer to instances in which the event or circumstance occurs precisely as well as instances in which the event or circumstance occurs to a close approximation, such as accounting for typical tolerance levels or variability of the embodiments described herein.

As used herein, the terms "optional" and "optionally" mean that the subsequently described event or circumstance may or may not occur and that the description includes instances where the event or circumstance occurs and instances in which it does not.

As used herein, the term "size" refers to a characteristic dimension of an object. Thus, for example, a size of an object that is spherical can refer to a diameter of the object. In the case of an object that is non-spherical, a size of the non-spherical object can refer to a diameter of a corresponding spherical object, where the corresponding spherical object exhibits or has a particular set of derivable or measurable properties that are substantially the same as those of the non-spherical object. Thus, for example, a size of a non-spherical object can refer to a diameter of a corresponding spherical object that exhibits light scattering or other properties that are substantially the same as those of the non-spherical object. Alternatively, or in conjunction, a size of a non-spherical object can refer to an average of various orthogonal dimensions of the object. Thus, for example, a size of an object that is a spheroidal can refer to an average of a major axis and a minor axis of the object. When referring to a set of objects as having a particular size, it is contemplated that the objects can have a distribution of sizes around the particular size. Thus, as used herein, a size of a set of objects can refer to a typical size of a distribution of sizes, such as an average size, a median size, or a peak size.

FIG. 1-FIG. 4 illustrate a time-lapse series of constant velocity relative motion between a prosthesis P, engaged by an installation system 100, and an installation site (S) for the prosthesis P. For purposes of this description, prosthesis P will be described as an acetabular cup to be installed into the installation site S—a prepared cavity in an acetabulum 110 as may be part of a hip replacement procedure.

System 100 includes a fixation apparatus 105 that fixes relative motion between a tool 115 mechanically communicated to prosthesis P and installation site S. There may be several ways to achieve this mechanical linkage, for example one or more Shantz screws fixed in the pelvic bone may secure tool 115 in the desired relative position. As described herein, installation system 100 moves prosthesis P into placement in installation site S with constant relative motion. There may be several mechanisms by which this constant relative motion is achieved. The specifics of which may impact the manner by which fixation apparatus 105 is configured and implemented. The term "constant relative motion" is not to require that the relative motion be necessarily uniform, though in some implementations uniform constant relative motion may be preferred. As illustrated, system 100 places prosthesis P in motion relative to installation site S and motion continues once started (hence constant motion) until the desired installation parameters are achieved (e.g., complete seating of prosthesis P in installation site S).

Fixation apparatus 105, sometimes referred to herein as a force transfer anchor, may be implemented in many different formats and modes. In some embodiments, apparatus 105 may consist almost exclusively of fixed static elements that secure, constrain, and/or fix tool 115 to a portion of bone or active foundation to be processed (e.g., acetabulum 110). In some embodiments, apparatus 110 may include a more complex dynamically adjustable structure for interacting with tool 115. Some functions described herein associated with apparatus 105, bone 110, and/or tool 115 may be shared, distributed, reallocated to some or others of the devices. For example in some embodiments, tool 115 and/or apparatus 105 may include force generators, such as to impart an implanting force to an implant. Apparatus 105 helps to improve the implanting (and other processings) in a number of possible ways as described herein.

Tool 115 may include a robotic system or other medical device (for example, one of the Behzadi Medical Devices (BMDs) described in an incorporated application).

Figure 2:
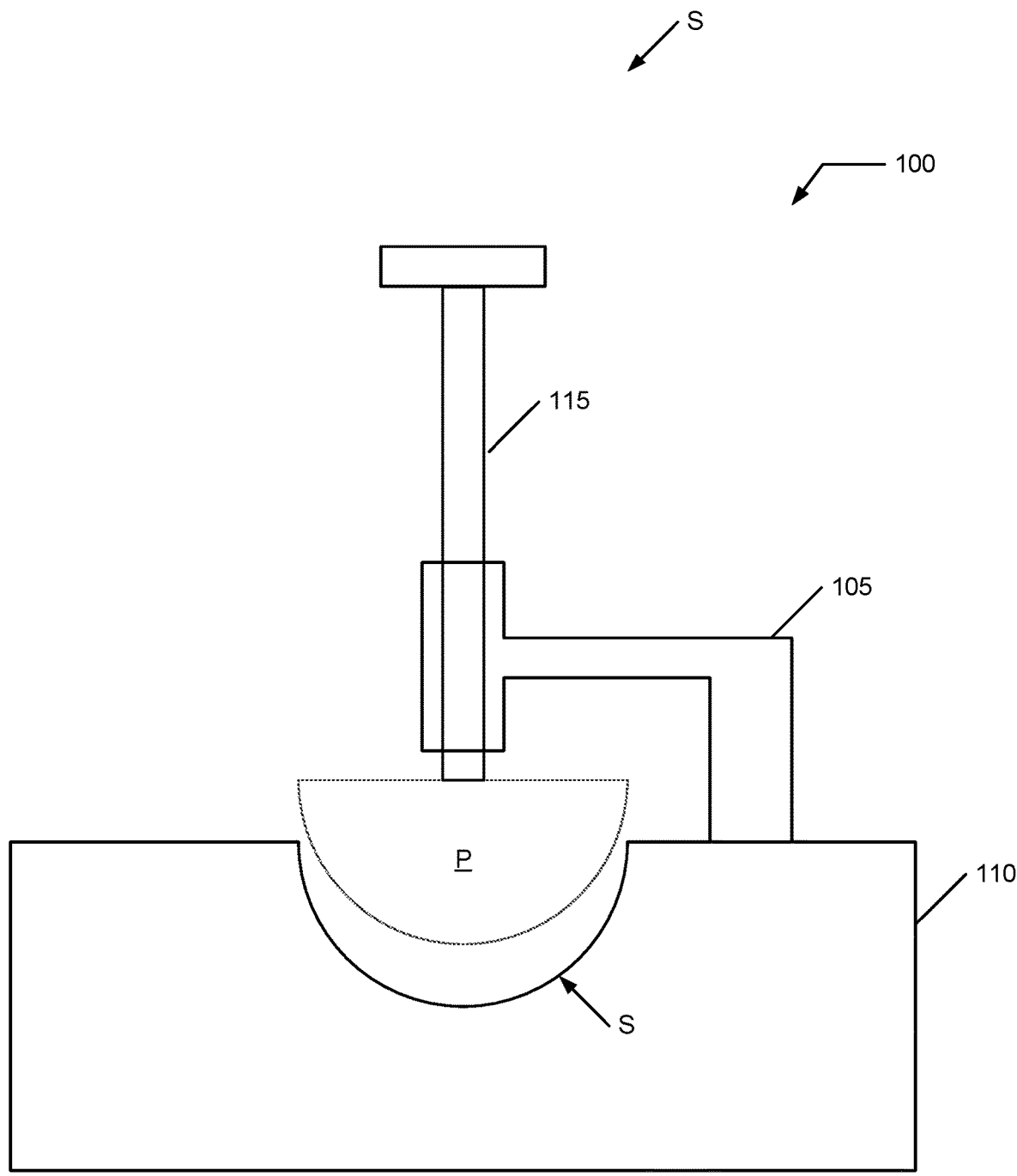
Figure 3:
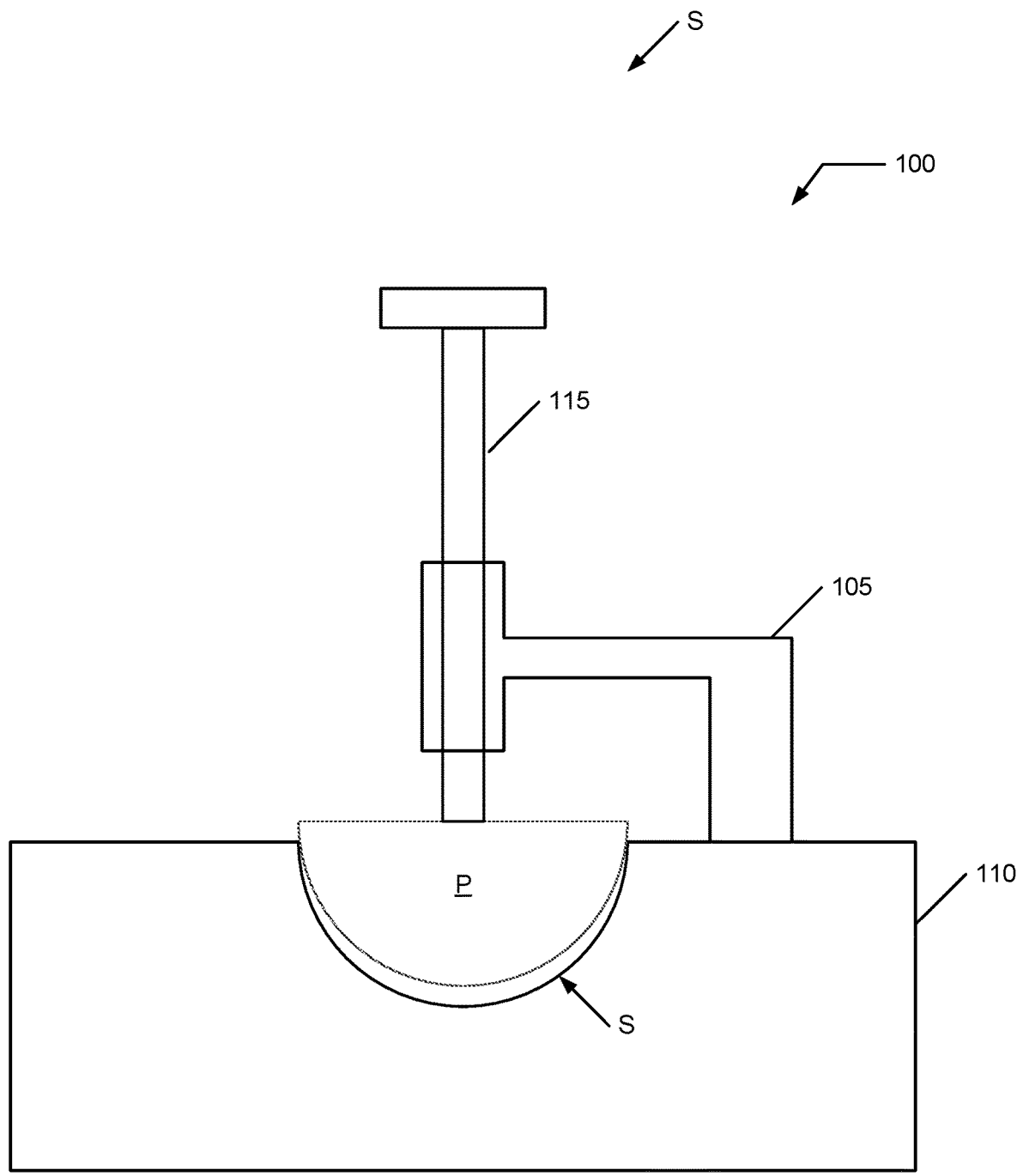
Figure 4:
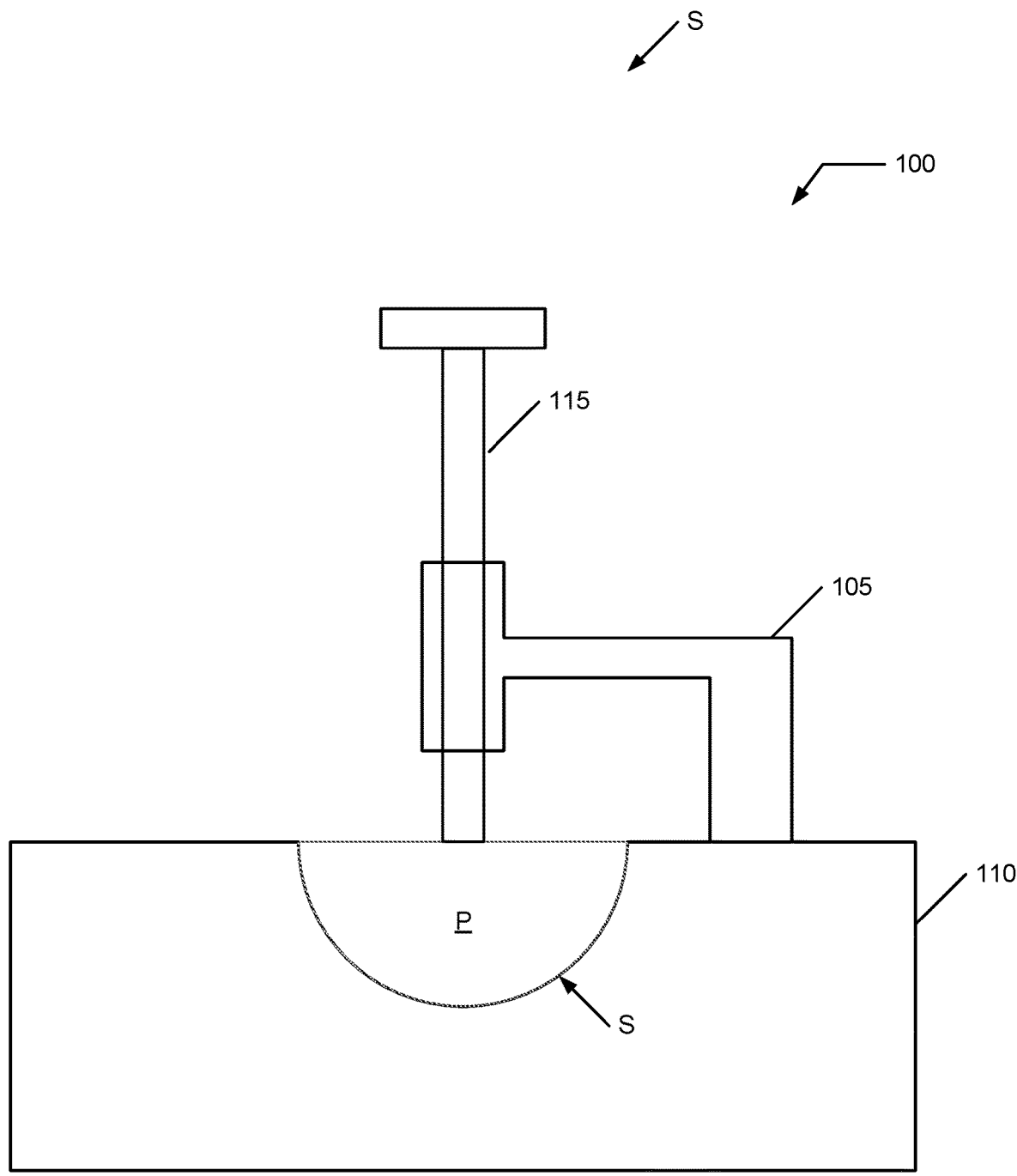

FIG. 1 illustrates an initial orientation of installation system 100 and installation site S, FIG. 2 illustrates a first period after an initiation of a constant velocity installation process, FIG. 3 illustrates a second period after the initiation of the constant velocity installation process, and FIG. 4 illustrates a third period after Initiation of the constant velocity installation process in which prosthesis P has been installed without meaningful acceleration or impacts.

One expression of acceleration is a change of velocity with respect to time. Thus any non-uniform constant motion may be considered to have some acceleration as the direction or speed changes. In the present context, as long as any acceleration does not produce impactful-type forces on prosthesis P or installation site S, such an embodiment may include the present invention. Preferably, the constant motion varies no more than a predetermined amount once started, for example, relative speed is maintained within a 25%, within 10%, within 5%, and within 1% variation.

As noted, an important consideration for some embodiments is relative motion which may include one or both of prosthesis P and installation site S being in motion, or being stationary, at any given time. Which element moves, and in which direction, is less important than that the relative motion be uniform.

It has been experimentally measured that when a cup is inserted without impacts, but rather at a constant velocity, that once the movement starts, the system may be exposed only to the coefficient of kinetic friction $U_k$. Some calculations suggest that the coefficient of kinetic friction for certain cup/cavity interfaces may be as much as 30% to 50% lower than the coefficient of static friction. The illustrated embodiment contemplates that the acetabular prosthetic cup be inserted into the pelvic acetabular bone at constant velocity (without significant acceleration and without impulsive forces). Some embodiments may be particularly appealing when the hip replacement procedure includes use of a robotic tool, such as MAKO robot, where the position of the robot is very stable. Or any system where the inserting tool such as BMD is able to be fastened to the OR table to become a rigid and stable structure.

The following is a possible representative technique. The robotic arm (or the rigid BMD tool) inserts one or more Schantz screws into pelvis around the periphery of the acetabular rim, and in that way, stabilizes the pelvis's position in relation to the robotic end effector arm (or a stabilized BMD tool). The robotic arm (or the stabilized BMD tool) can then push the cup into the pelvis at constant velocity without impacts, dealing only with the coefficient of kinetic friction once the motion has started, and hence (the resistive forces of kinetic friction regime). The resistive force (FR) that are encountered may be up to 30% to 50% lower, than an alternative where the cup would be inserted with impulsive forces. Adding ice, slurry or other surface treatment or surface application (see for example, U.S. Patent Application No. 62/319,377 filed 7 Apr. 2016 and its non-provisional conversion U.S. patent application Ser. No. 15/234,927 filed 11 Aug. 2016 and a continuation-in-part thereof, U.S. patent application Ser. No. 15/406,752 filed 15 Jan. 2017, the contents of these applications are hereby expressly incorporated by reference thereto in their entireties for all purposes) to this method of constant insertion can diminish the force of static friction potentially by greater than 50%, making insertion with constant force even more attractive.

Embodiments of the present invention may include one of more solutions to the above problems. The incorporated U.S. Pat. No. 9,168,154 includes a description of several embodiments, sometimes referred to herein as a BMD3 device, some of which illustrate a principle for breaking down large forces associated with the discrete blows of a mallet into a series of small taps, which in turn perform similarly in a stepwise fashion while being more efficient and safer. The BMD3 device produces the same displacement of the implant without the need for the large forces from the repeated impacts from the mallet. The BMD3 device may allow modulation of force required for cup insertion based on bone density, cup geometry, and surface roughness. Further, a use of the BMD3 device may result in the acetabulum experiencing less stress and deformation and the implant may experience a significantly smoother sinking pattern into the acetabulum during installation. Some embodiments of the BMD3 device may provide a superior approach to these problems, however, described herein are two problems that can be approached separately and with more basic methods as an alternative to, or in addition to, a BMD3 device. An issue of undesirable torques and moment arms is primarily related to the primitive method currently used by surgeons, which involves manually banging the mallet on the impaction plate. The amount of force utilized in this process is also non-standardized and somewhat out of control.

With respect to the impaction plate and undesirable torques, an embodiment of the present invention may include a simple mechanical solution as an alternative to some BMD3 devices, which can be utilized by the surgeon's hand or by a robotic machine. A direction of the impact may be directed or focused by any number of standard techniques (e.g., A-frame, C-arm or navigation system). Elsewhere described herein is a refinement of this process by considering directionality in the reaming process, in contrast to only considering it just prior to impaction. First, we propose to eliminate the undesirable torques by delivering the impacts by a sledgehammer device or a structure (e.g., hollow cylindrical mass) that travels over a stainless rod.

Figure 5:
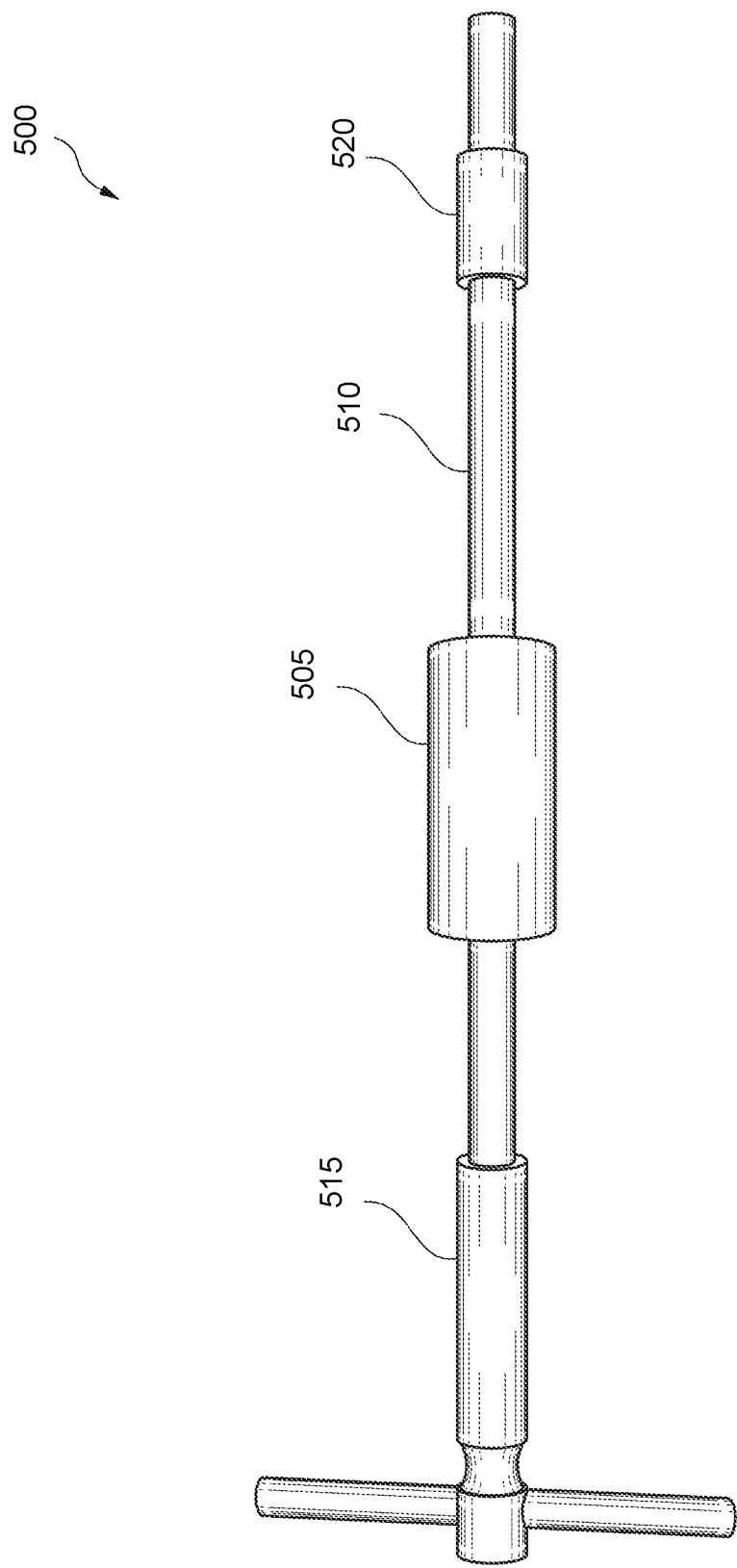
FIG. 5-FIG. 10 illustrate embodiments including installation of a prosthesis, including installation into living bone.
Figure 6:
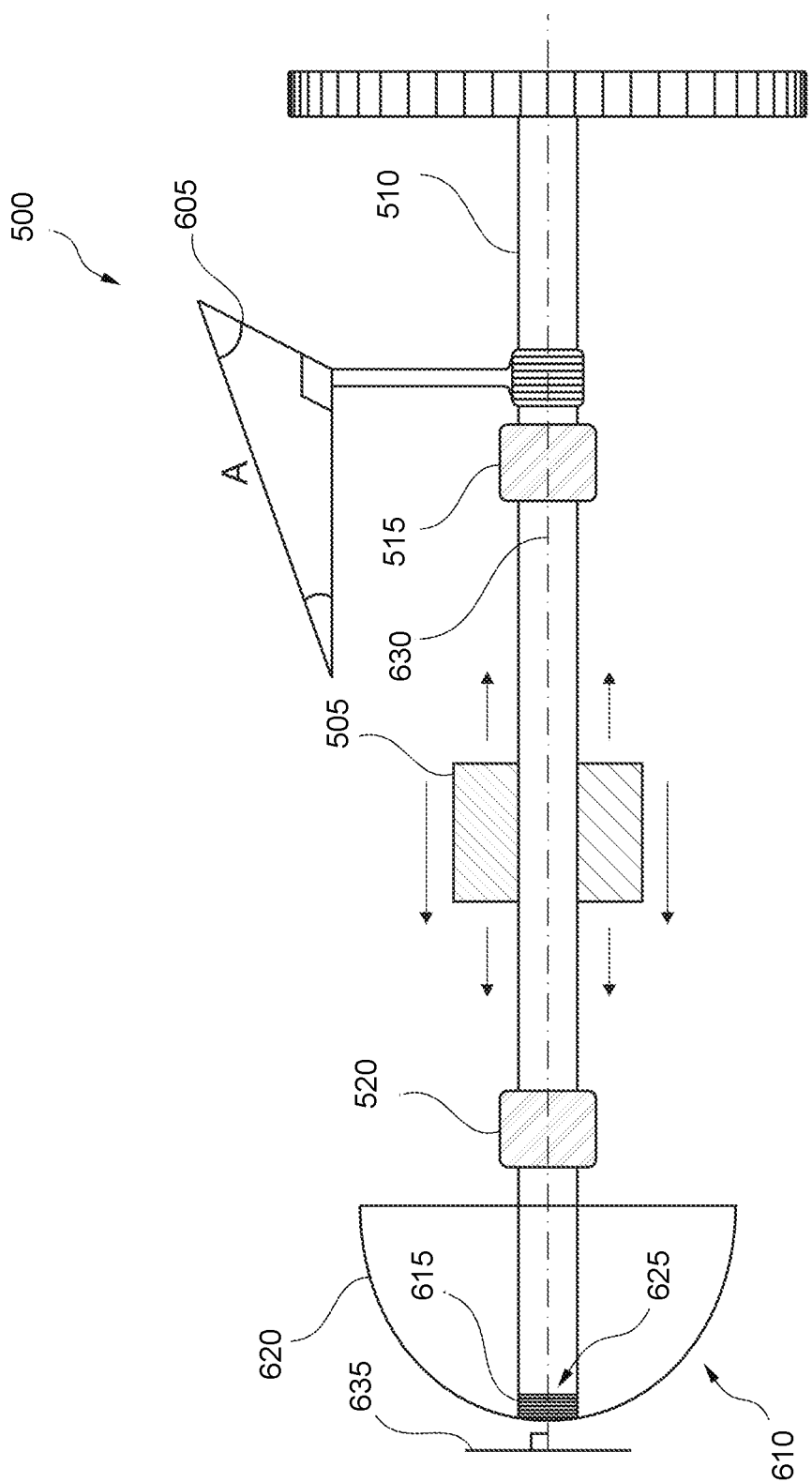

FIG. 5 illustrates an embodiment of the present invention for a sliding impact device 500, and FIG. 6 illustrates a lengthwise cross-section of sliding impact device 500 including an attachment of a navigation device 605.

Device 500 includes a moveable hammer 505 sliding axially and freely along a rod 510. Rod 510 includes a proximal stop 515 and distal stop 520. These stops that may be integrated into rod 510 to allow transference of force to rod 510 when hammer 505 strikes distal stop 520. At a distal end 610 of rod 510, device 500 includes an attachment system 615 for a prosthesis 620. For example, when prosthesis 620 includes an acetabular cup having a threaded cavity 625, attachment system 615 may include a complementary threaded structure that screws into threaded cavity 625. The illustrated design of device 500 allows only a perfect axial force to be imparted. The surgeon cannot deliver a blow to the edge of an impaction plate. Therefore the design of this instrument is in and of itself protective, eliminating a problem of "surgeon's mallet hitting on the edge of the impaction plate" or other mis-aligned force transference, and creating undesirable torques, and hence unintentional mal-alignment of prosthesis 620 from an intended position/orientation.

A longitudinal axis 630 extends through the ends of rod 510. Attachment system 615 aligns prosthesis 620 to axis 630 when rod 510 is coupled to threaded cavity 625. An apex of prosthesis 620 (when it generally defines a hollow semispherical shell) supports a structure that defines threaded cavity 625 and that structure may define a plane 635 that may be tangent to the apex, with plane 635 about perpendicular to axis 630 when rod 510 engages prosthesis 620. Operation of device 500 is designed to deliver only axial (e.g., aligned with axis 630 and thus non-torqueing) forces to prosthesis 620. Other embodiments illustrated in FIG. 7-FIG. 10 may be similarly configured.

Figure 7:
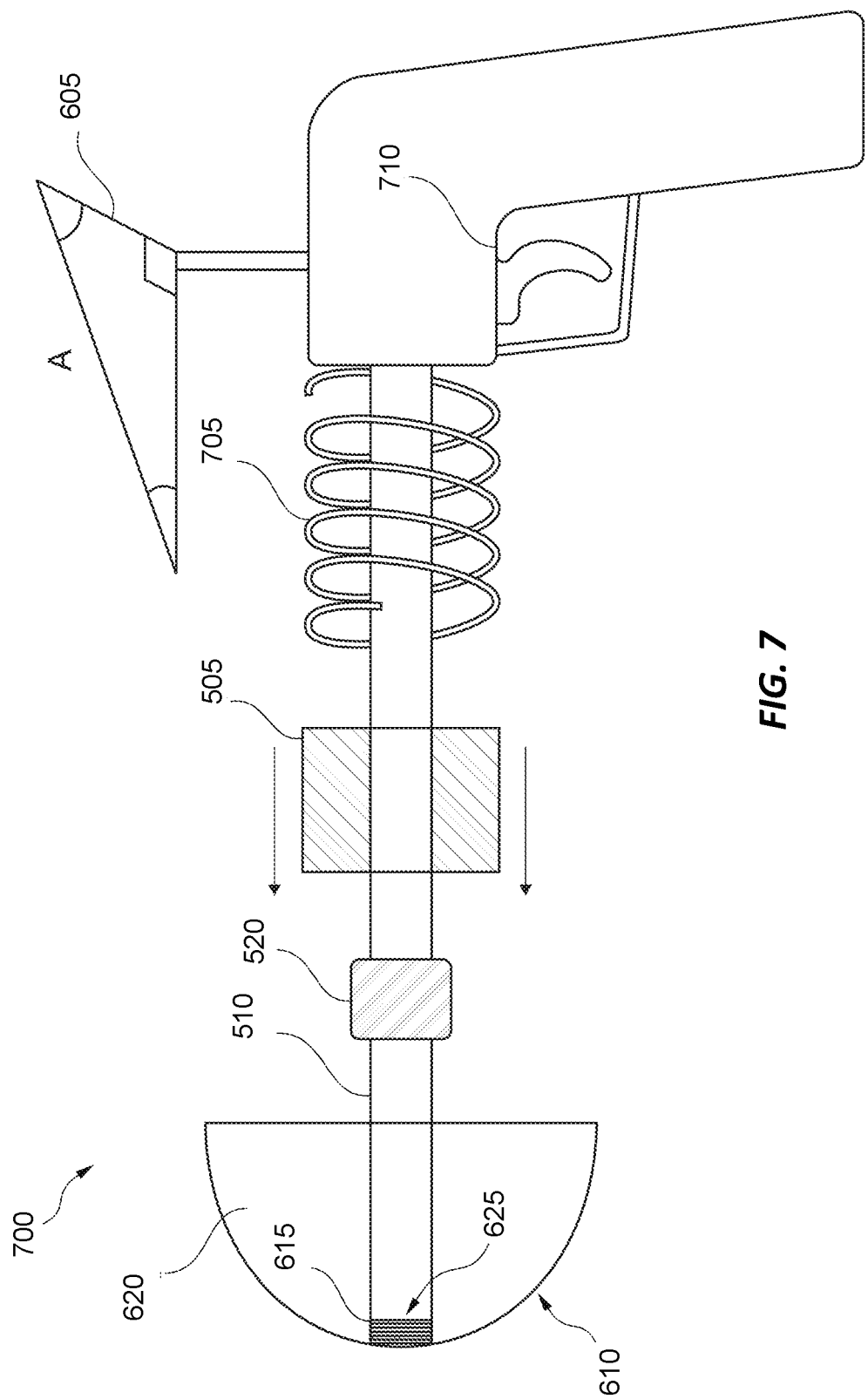

FIG. 7 illustrates a cockup mechanical gun 700 embodiment, an alternative embodiment to the sliding impact device illustrated in FIG. 5 and FIG. 6. An alternate embodiment includes cockup mechanical gun 700 that uses the potential energy of a cocked up spring 705 to create an axially aligned impaction force. Hammer 505 is drawn back and spring 705 is locked until an operator actuates a trigger 710 to release spring 705 and drive hammer 505 along rod 510 to strike distal stop 520 and transfer an axially aligned impacting force to prosthesis 620.

Each pull of trigger 710 creates the same predetermined fixed unit of force (some alternatives may provide a variably predetermined force). The surgeon cannot deliver a misaligning impact to an impaction plate with this design.

Figure 8:
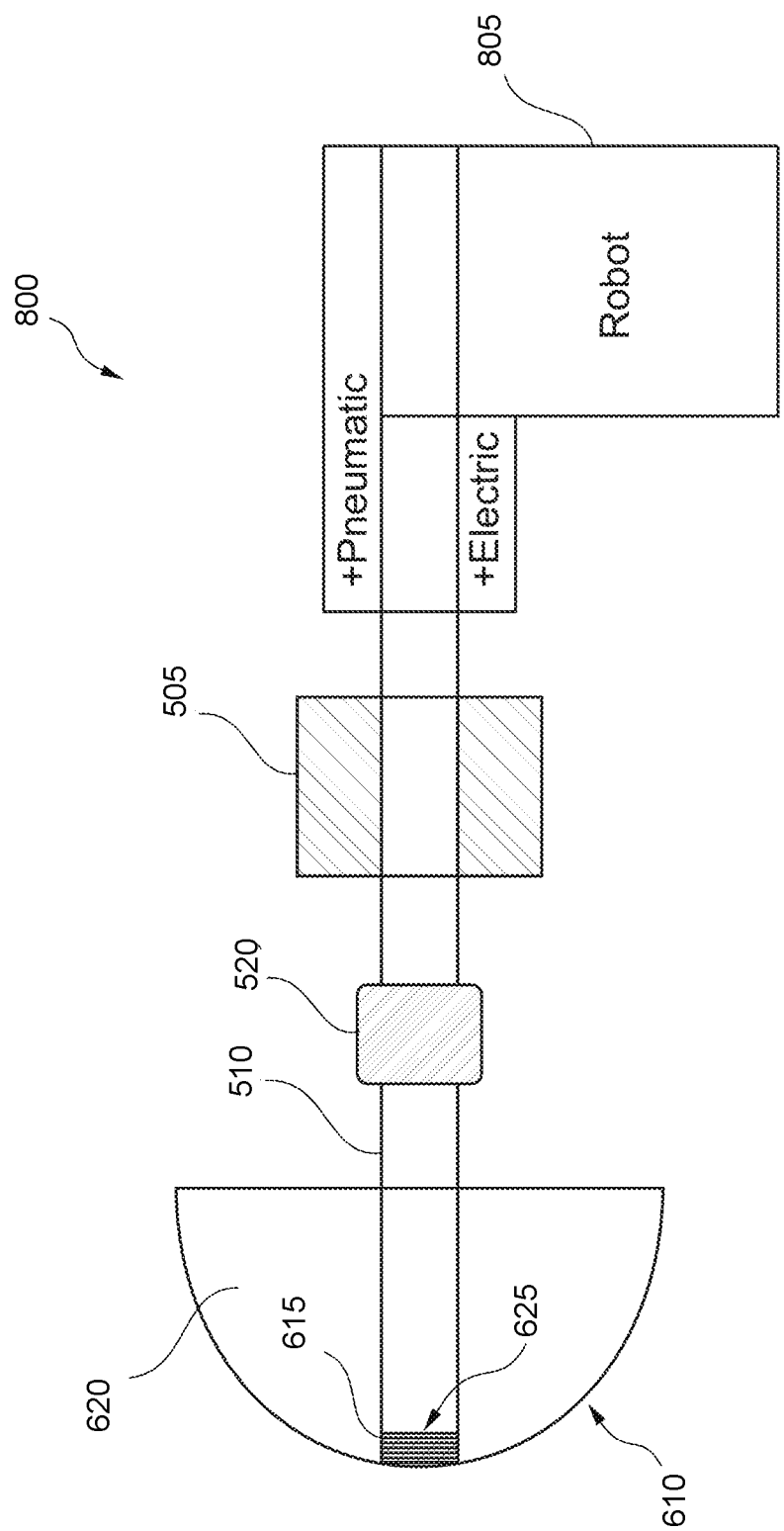

FIG. 8 illustrates an alternative robotic device 800 embodiment to the devices of FIG. 5-7 including a robotic control structure 805. For example, device 500 and/or gun 700 may be mounted with robot control structure 805 and the co-axial impacts may be delivered mechanically by a robotic tool using pneumatic or electric energy.

Figure 9:
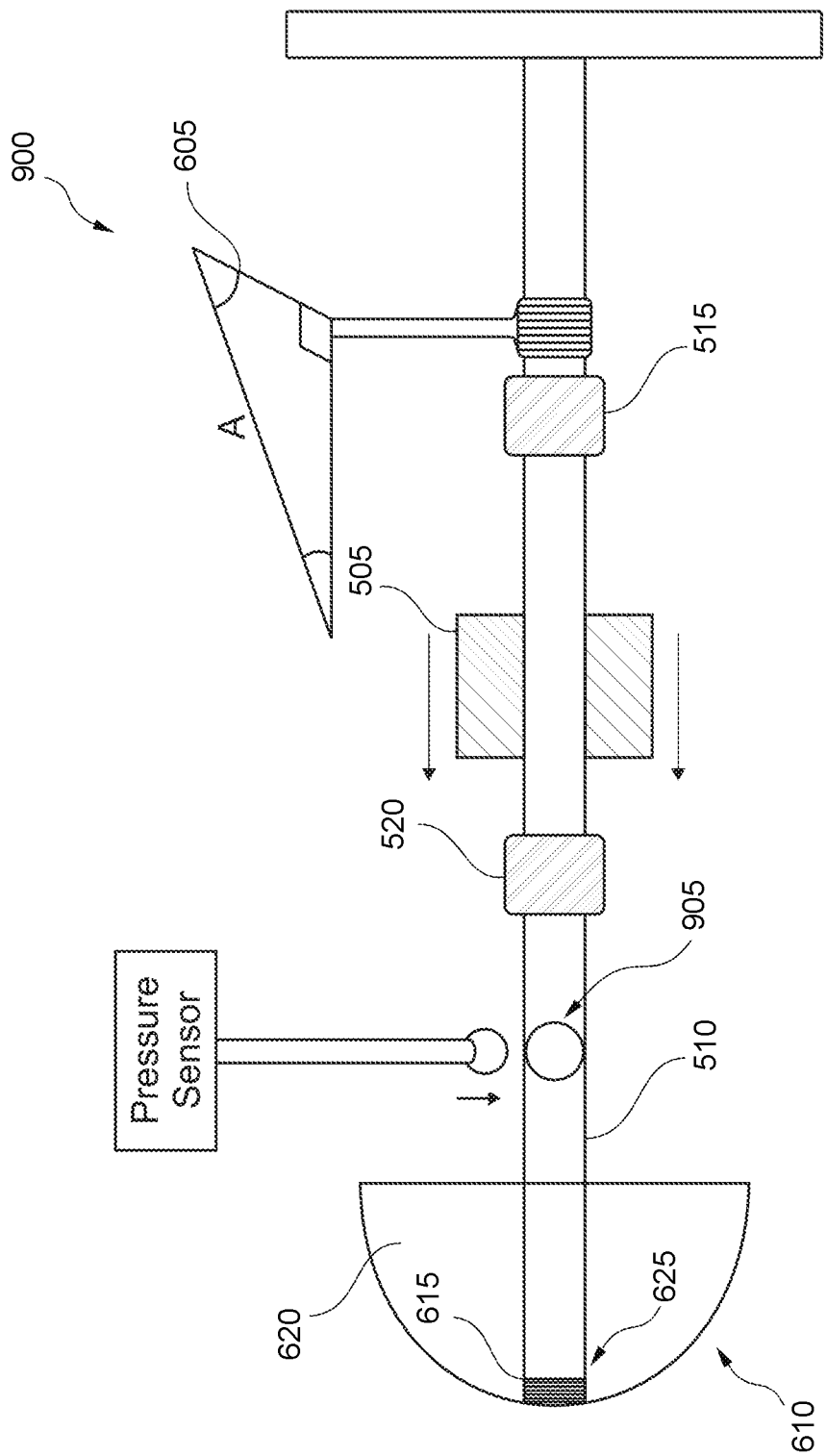

FIG. 9 illustrates an alternative embodiment 900 to the devices of FIG. 5-8 including a pressure sensor 905 to provide feedback during installation. With respect to management of the force required for some of these tasks, it is noted that with current techniques (the use of the mallet) the surgeon has no indication of how much force is being imparted onto the implant and/or the implant site (e.g., the pelvis). Laboratory tests may be done to estimate what range of force should be utilized in certain age groups (as a rough guide) and then fashioning a device 900, for example a modified sledgehammer 500 or cockup gun 700 to produce just the right amount of force. Typically the surgeon may use up to 2000N to 3000N of force to impact a cup into the acetabular cavity. Also, since some embodiments cannot deliver the force in an incremental fashion as described in association with the BMD3 device, device 900 includes a stopgap mechanism. Some embodiments of the BMD3 device have already described the application of a sensor in the body of the impaction rod. Device 900 includes sensing system/assembly 905 embedded in device 900, for example proximate rod 510 near distal end 610, and used to provide valuable feedback information to the surgeon. Pressure sensor 905 can let the surgeon know when the pressures seems to have maximized, whether used for the insertion of an acetabular cup, or any other implant including knee and shoulder implants and rods used to fix tibia and femur fractures. When pressure sensor 905 is not showing an advance or increase in pressure readings and has plateaued, the surgeon may determine it is time to stop operation/ impacting. An indicator, for example an alarm can go off or a red signal can show when maximal peak forces are repeatedly achieved. As noted above, the incorporated patents describe a presence of a pressure sensor in an installation device, the presence of which was designed as part of a system to characterize an installation pulse pattern communicated by a pulse transfer assembly. The disclosure here relates to a pressure sensor provided not to characterize the installation pulse pattern but to provide an in situ feedback mechanism to the surgeon as to a status of the installation, such as to reduce a risk of fracturing the installation site. Some embodiments may also employ this pressure sensor for multiple purposes including characterization of an applied pulse pattern such as, for example, when the device includes automated control of an impacting engine coupled to the hammer. Other embodiments of this invention may dispose the sensor or sensor reading system within a handle or housing of the device rather than in the central rod or shaft.

Figure 10:
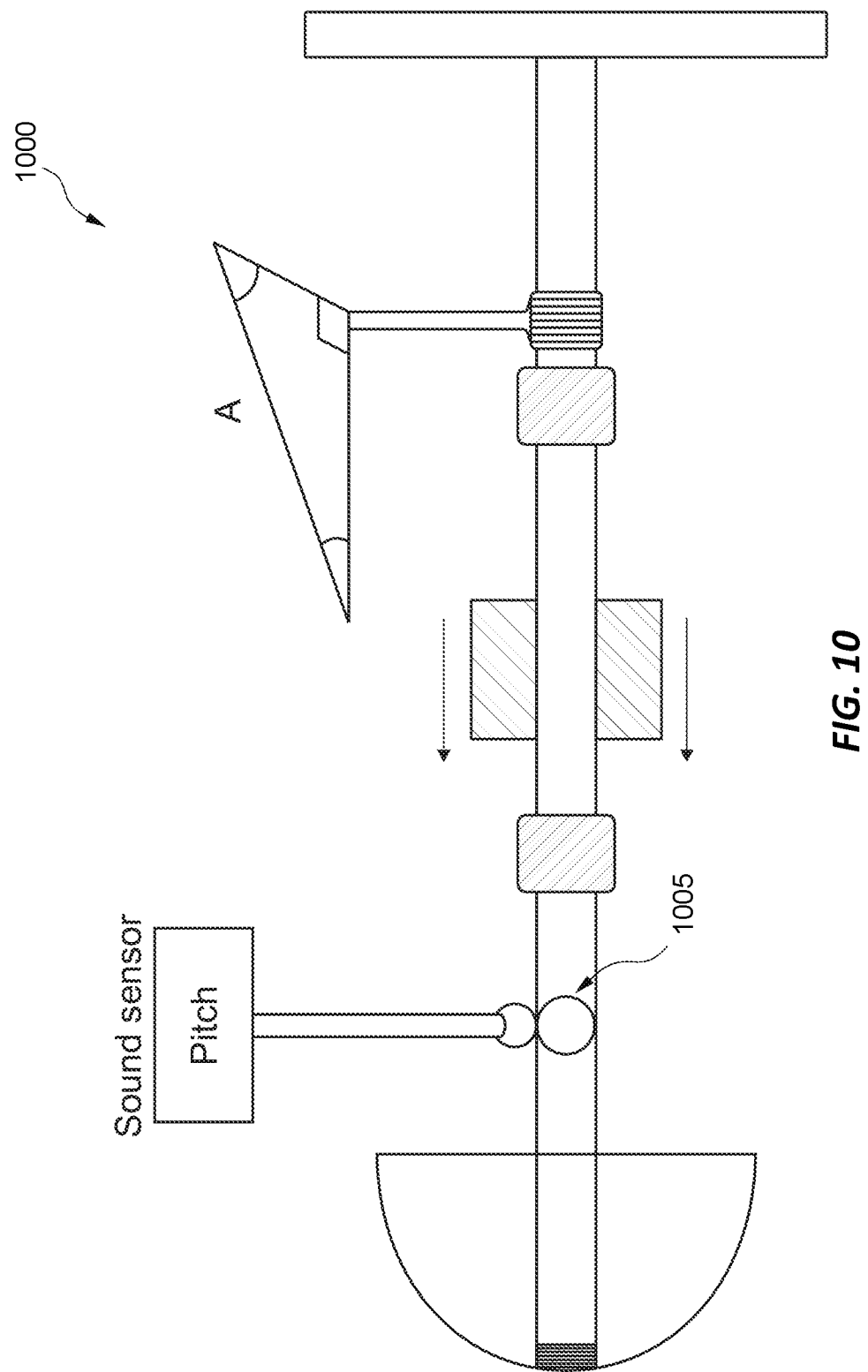

FIG. 10 illustrates an alternative device 1000 embodiment to the feedback system of FIG. 9 including a sound sensor 1005 to provide feedback for the embodiments of FIG. 5-9. Surgeons frequently use a change in pitch (sound) to gauge whether an implant (e.g., the cup) has "bottomed out" (an evaluation of a "seatedness" of the implant) and device 1000 includes sound sensor 1005 either attached or coupled to rod 510 or otherwise disposed separately in the operating room. Sound sensor system/assembly 1005 may be used in lieu of, or in addition to, pressure sensor system/assembly 905 illustrated in FIG. 9.

Figure 11:
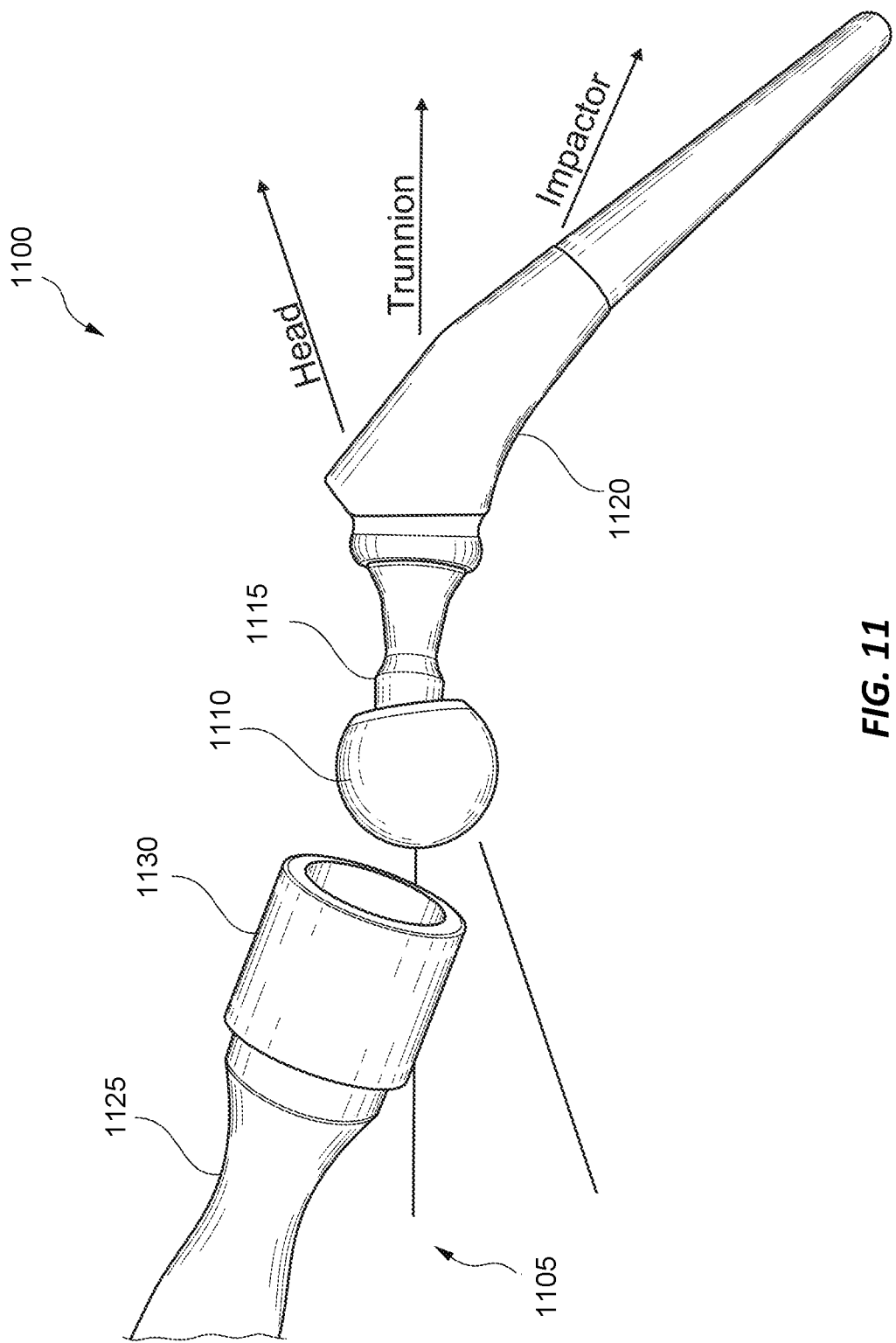
FIG. 11-FIG. 14 illustrate prosthesis assembly embodiments including use of variations of the prosthesis installation embodiments of FIG. 5-FIG. 10, such as may be used to reduce a risk of trunnionosis.

FIG. 11-FIG. 14 illustrate prosthesis assembly embodiments including use of variations of the prosthesis installation embodiments of FIG. 5-FIG. 10, such as may be used to reduce a risk of trunnionosis or for other advantage. FIG. 11 illustrates a modular prosthesis 1100 and assembly tool 1105. Prosthesis 1100 includes a head 1110 and a trunnion taper 1115 at an end of a stem 1120 (e.g., a femoral stem for supporting a ball head to fit within an acetabular cup used in a total hip replacement procedure). During the procedure, the surgeon assembles prosthesis 1100 by using tool 1105 which may include an impact rod 1125 attached to a head coupler 1130. The surgeon uses tool 1105 to drive head 1110 onto trunnion taper 1115 which conventionally includes a free mallet striking tool 1105. Such a procedure may be prone to the similar problems as installation of a prosthesis into an implant site, namely application of off-axis torqueing forces and an uncertainty of applied force and completion of assembly.

It is believed that even a 0.1 degree mal-alignment on head 1110 on trunnion taper 1115 may lead to progressive wear and metalosis. Variations of the embodiments of devices illustrated in FIG. 5-FIG. 10 and its associated content may be developed to help resolve this problem. In the case of "non-torqueing axiality" of forces from an assembly device, a bore of the head may define an axis, the trunnion taper may define an axis, with the assembly device aligning these axes and then applying its forces in co-axial alignment with these co-axially aligned axes. Such an embodiment may reduce or eliminate any force-responsive rotations of the head with respect to the taper as the head is seated into position by the assembly device.

Figure 12:
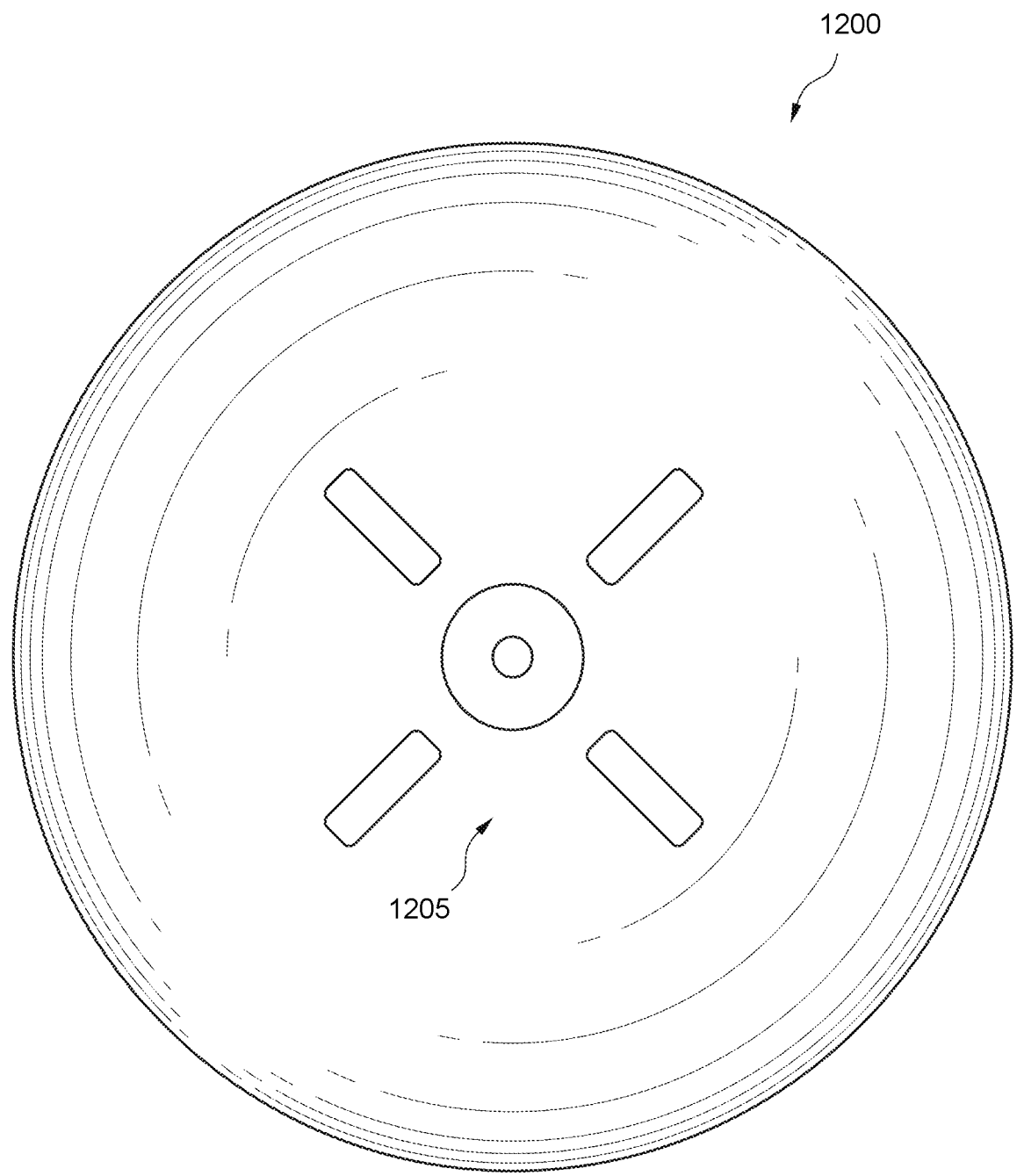

FIG. 12 illustrates a femoral head 1205, a variation of head 1110 illustrated in FIG. 11, to be assembled onto trunnion taper 1115 that is coupled to femoral stem 1120. A center dot 1210 may be placed on femoral (or humeral) head 1205 to be impacted using tool 1105.

Figure 13:
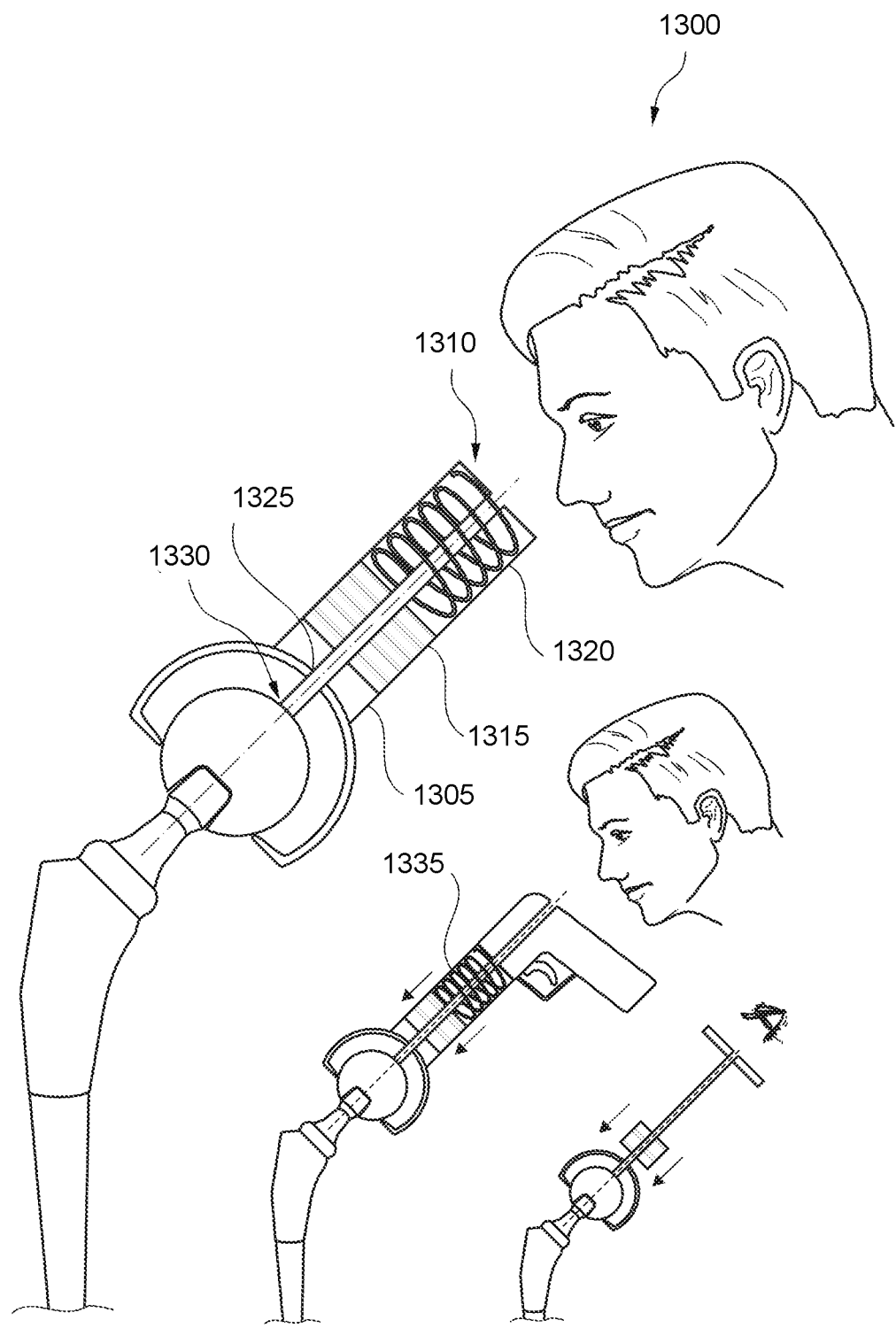

FIG. 13 illustrates alignment of an installation device 1300, a variation of any of devices 500-1000, with femoral head 1205 for properly aligned impaction onto trunnion taper 1115, such as an embodiment of FIG. 5-FIG. 10 adapted for this application. Such adaptation may include, for example, an axial channel 1310 to view dot 1210, and align force transference, prior to operation of hammer 505. Device 1300 includes a sledgehammer 1315 and a cock-up spring to drive sledgehammer 1315. A slot 1325 allows an operator to visualize a centering mark 1330. A spring-loading 1335 may be used to operate a device.

Dot 1210 can be aligned with an impactor/device/gun. Once axial alignment, such as through the sight channel, has been confirmed, a sledgehammer, a cockup gun, or other similar device can bang the impactor onto femoral (humeral) head 1205 to impact it on trunnion taper 1115. The co-axiality of the head and the device can be confirmed visually (for example, through a hollow cylinder that comprises a center shaft of the device) or with a variety of electronic and laser methods.

Figure 14:
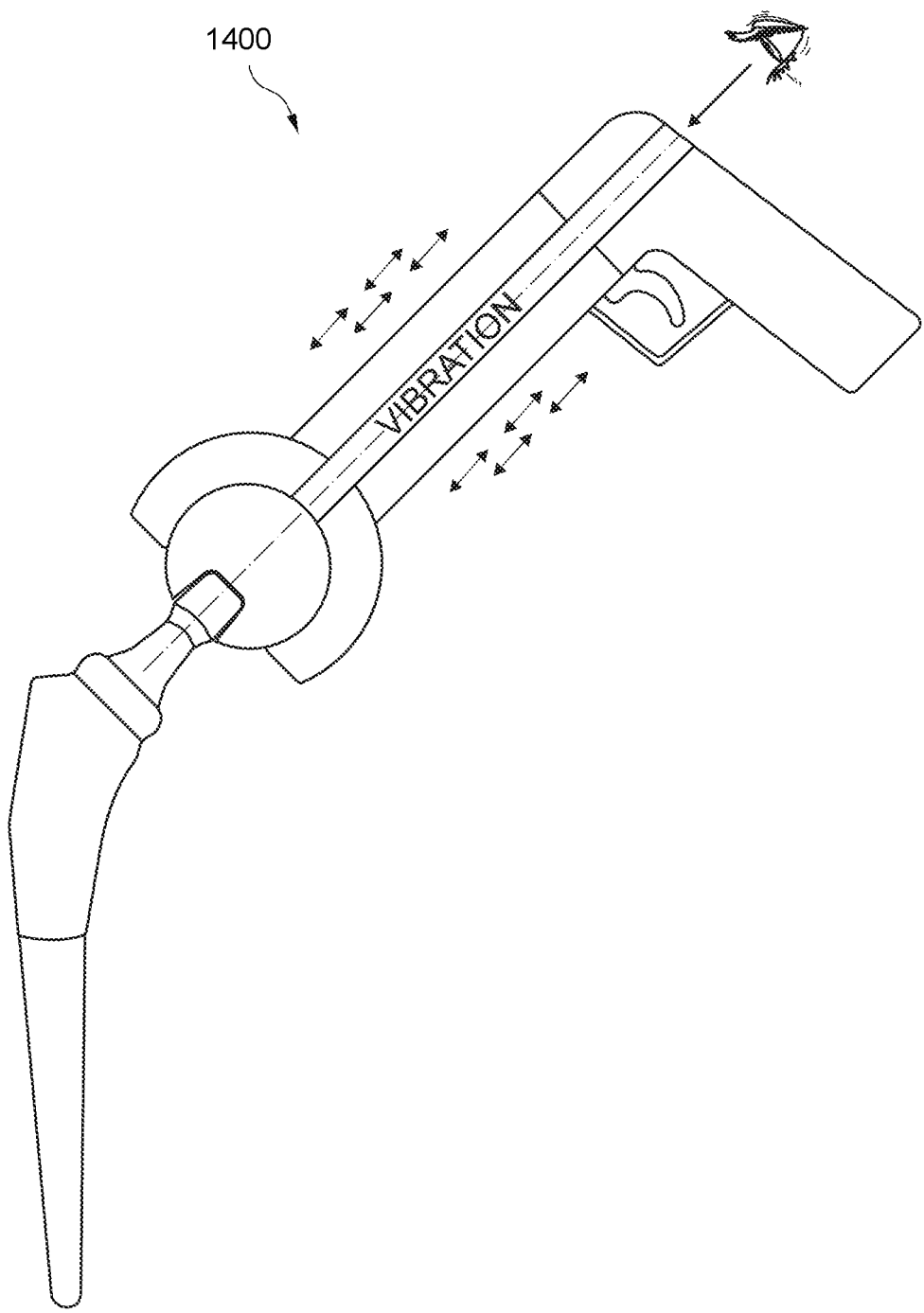

FIG. 14 illustrates use of a modified vibratory system 1400, a variation of installation device 1300 for assembly of the modular prosthesis illustrated in FIG. 11. Alternatively to device 1300, a variation of the BMD3 device can be used to insert the femoral and humeral heads 1110 onto trunnion taper 1115. For example, a version of the BMD3 device where femoral head 1110 is grasped by a "vibrating gun" and introduced methodically and incrementally onto trunnion taper 1115. Since there are no large forces being applied to the head/trunnion junction, there is essentially no possibility, or a reduced possibility, of head 1110 seating onto trunnion taper 1115 in a misaligned fashion. It would be possible to use the same technique of marking the center of head 1110 and lining it up with trunnion taper 1115 and device axially before operating the device.

Figure 15:
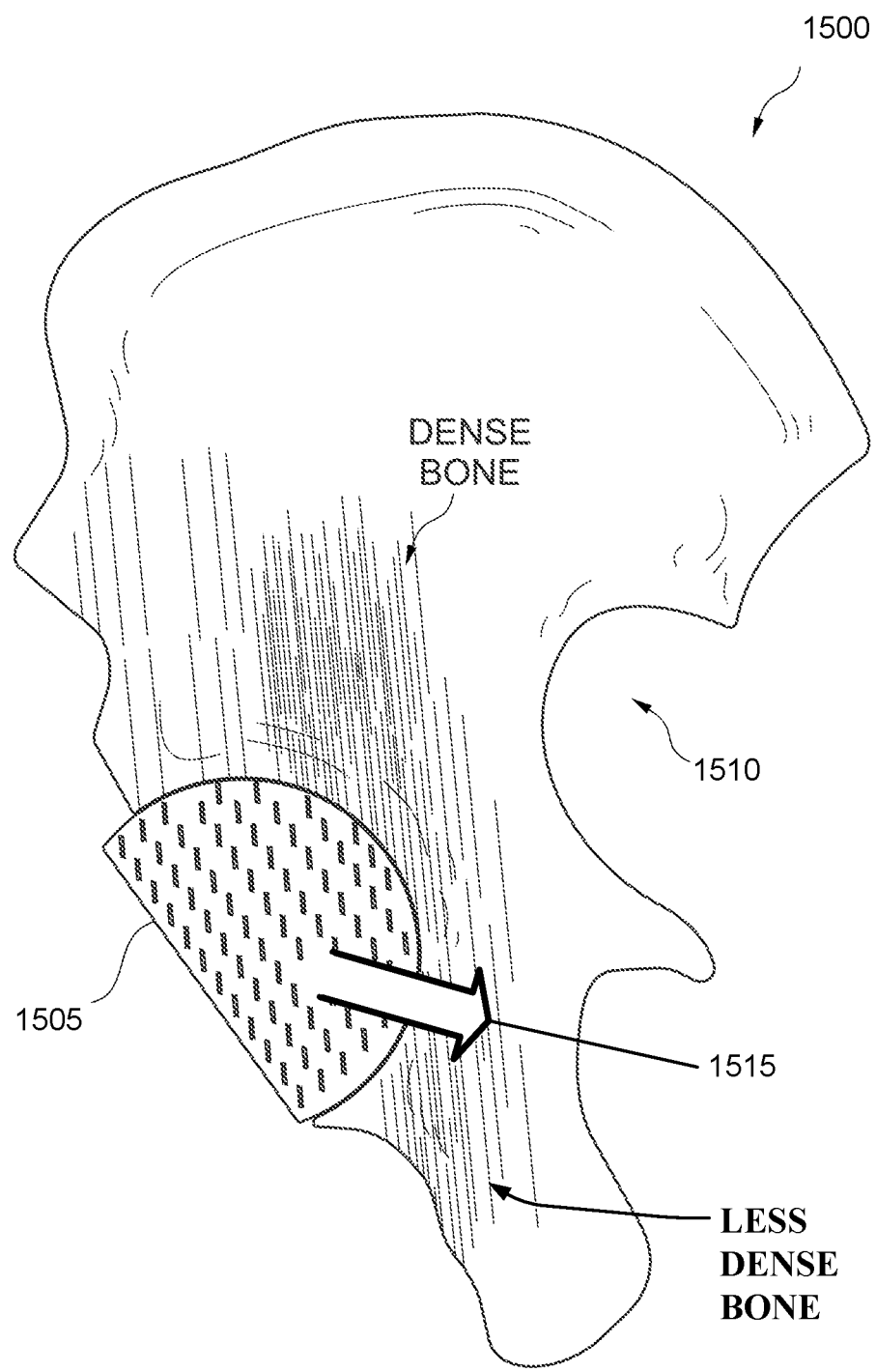
FIG. 15-FIG. 16 illustrate an improvement to site preparation for an installation of a prosthesis.
Figure 16:
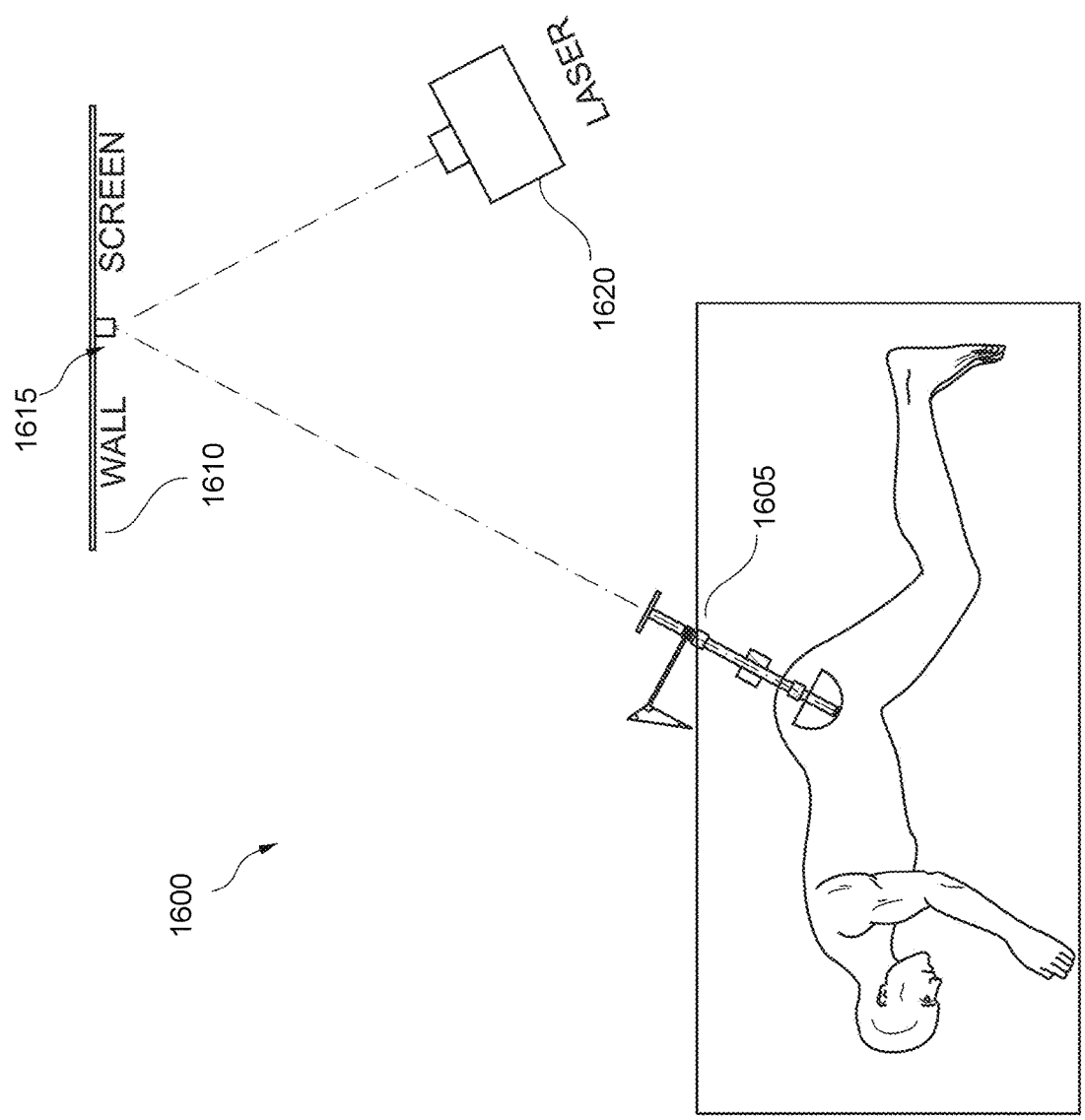

FIG. 15-FIG. 16 illustrate an improvement to site 1500 preparation for an installation of a prosthesis 1505. FIG. 15 illustrates a site 1500 in which prosthesis 1505 is installed highlighting a problem with site preparation for a prosthesis installation procedure having variable density bone (line thickness/separation distance reflecting variable bone density) of acetabulum 1510. There may be an implant or other site to be prepared having a region including dense bone and a region including less dense bone, both regions present at the site. Some processings (e.g., reaming or other cutting) can cause a processing tool have an altered path 1515 from an intended path deeper into the dense bone. Altered path 1515 is shifted, such as away from the dense bone towards the less dense bone.

There is a secondary problem with the process of acetabular preparation and implantation that leads to cup mal-alignment. Currently, during the process of acetabular reaming, surgeons make several assumptions. One common assumption is that the reamer is fully seated in a cavity and surrounded on all sides by bone. Another common assumption is that the bone that is being reamed is uniform in density. Imagine a carpenter that is preparing to cut a piece of wood with a saw. Now imagine that parts of this piece of wood are embedded with cement and some parts of the piece of wood are hollow and filled with air. The carpenter's saw will not produce a precise cut on this object. Some parts are easy to cut and some parts are harder to cut. The saw blades skives and bends in undesirable ways. A similar phenomenon happens in acetabular preparation with a reamer and when performing the cuts for knee replacement with a saw. With respect to the acetabulum, the side of the cavity that is incomplete (side of the reamer that is uncovered) will offer less resistance to the reamer and therefor the reamer preferentially reams towards the direction of the uncovering. Second, the reamer cuts the soft bone much more easily than the dense and sclerotic bone, so the reamer moves away from the sclerotic bone and moves toward the soft bone. From a machining perspective, the reaming and preparation of the acetabulum may not be concentric or precise. This maybe a significant factor in the surgeon's inability to impact the cup in the desired location FIG. 16 illustrates an alignment system 1600 for preparation and installation of a prosthesis to help address/minimize this effect. A first step that can be taken is to include directionality into the process of reaming at the outset, and not just at the last step during impaction. Current technique allows the surgeon to ream the cup haphazardly moving the reamer handle in all directions, being ignorantly unaware that he is actually creating a preference for the sinking path of the acetabular implant. Ultimately the direction in which the surgeon reams may in fact be determining the position/path of the final implant. The surgeon then impacts the cup using the traditional A-frame or any of the currently used intra-operative measurement techniques such as navigation or fluoroscopy. These methods provide information about the position of the cup either as it is being implanted or after the implantation has occurred. None of these techniques predetermine the cup's path or function to guide the cup in the correct path.

Proposed is a method and a technique to eliminate/reduce this problem. Before the surgeon begins to ream the acetabulum, the reamer handle should be held, with an A-frame attached, in such a way to contemplate the final position of the reamer and hence the implant, (e.g., hold the reamer in 40 degree abduction and 20 degree anteversion reaming is started). This step could also be accomplished with navigation or fluoroscopy. The surgeon could, for example, immediately mark this position on a screen or the wall in the operating room as described below and as illustrated in FIG. 16. After the anticipated position of the reamer is marked, the surgeon can do whatever aspect of reaming that needs to be done. For example the first reaming usually requires medialization in which the reamer is directed quite vertically to ream in to the pulvinar. Typically three or four reamings are done. First, the acetabular cavity is medialized. The other reamings function to get to the subchondral bone in the periphery of the acetabulum. One solution may be that after each reaming, the reamer handle be held in the final anticipated position of the implant. In some cases it may be difficult to have an A-frame attached to every reamer and to estimate the same position of the reamer in the operating space accurately with the A-frame.

An alternative to that is also proposed to address this process. For example, at a proximal end of the reamer shaft handle will be placed a first reference system 1605, for example a laser pointer. This laser pointer 1605 will project a spot 1610 either on a wall or on a screen 1615, a known distance from the operating room table. That spot 1610 on screen 1615 (or on the screen) is then marked with another reference system 1620, for example a second independent laser pointer that sits on a steady stand in the operating room. Thereafter manipulating the shaft handle so that the first reference system has the desired relationship, example co-aligned, with the second reference system, the surgeon knows that the device attached to the handle has the desired orientation. So when the first reamer is held in the anticipated and desired final alignment of the implant (e.g., 40 degree abduction, 20 degree anteversion for many preferred installation angles of an acetabular cup), the laser pointer at the proximal end of the reamer handle projects a spot on the wall or screen. That spot is marked with the second stationary laser, and held for the duration of the case. All subsequent reamings will therefore not require an A-frame to get a sense of the proper alignment and direction of the reamer. The surgeon assures that no matter how he moves the reamer handle in the process of reaming of the acetabulum, that the reaming finishes with the reamer handle (laser pointer) pointing to the spot on the wall/screen. In this manner, directionality is assured during the reaming process. In this way the sinking path of the actual implant is somewhat predetermined. And no matter what final intra-operative monitoring technique is used (A-frame, C-Arm, Navigation) that the cup will likely seat/sink more closely to the desired final position.

Figure 17:
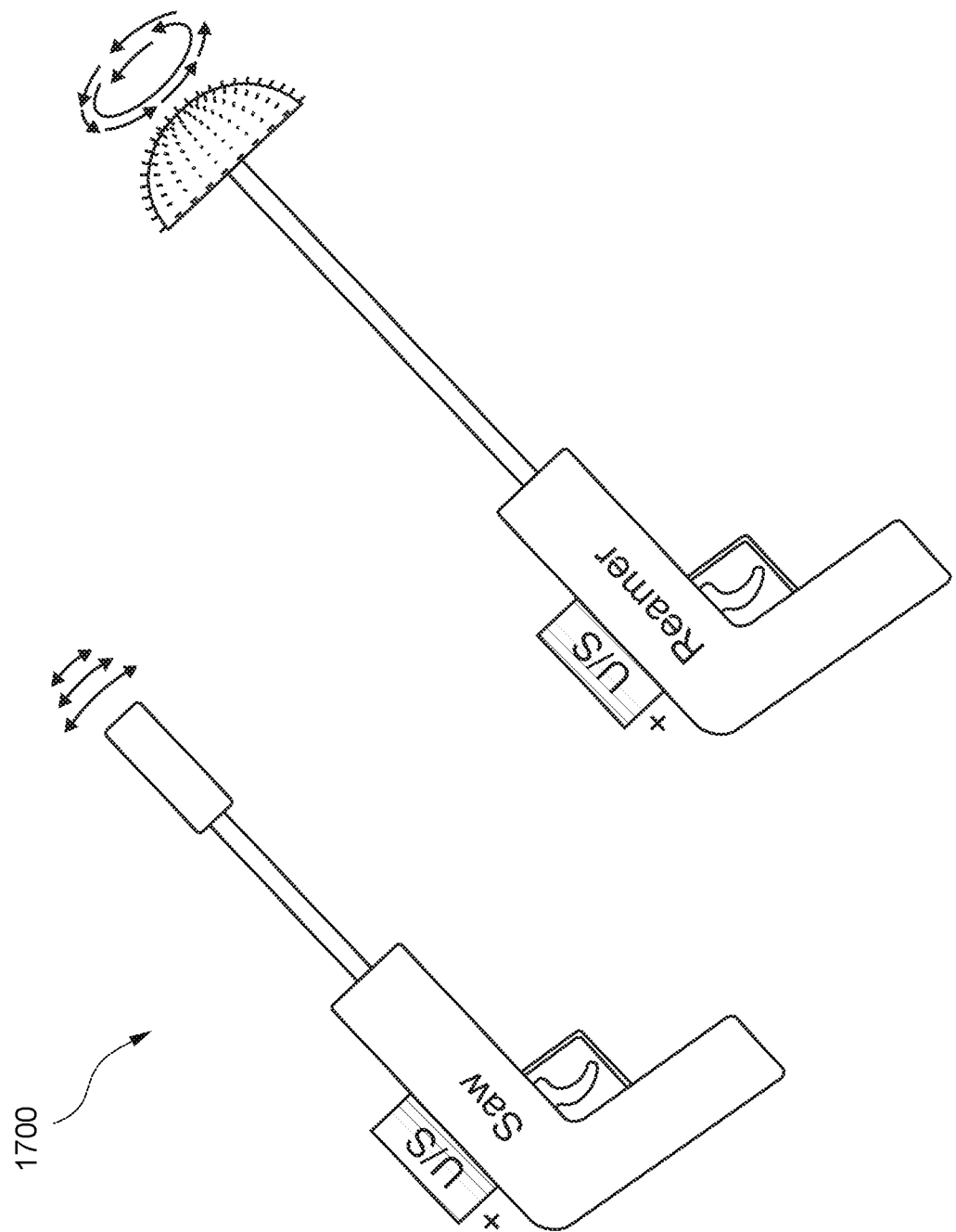
FIG. 17 illustrates modified surgical devices incorporating vibratory energy as at least an aid to mechanical preparation.

FIG. 17 illustrates modified surgical devices 1700 incorporating vibratory energy as at least an aid to mechanical preparation. Also proposed herein is another concept to address a problem associated with non-concentric reaming of the acetabulum caused by variable densities of the bone and the uncovering of the reamer. Imagine the same carpenter has to cut through a construct that is made out of wood, air, and cement. The carpenter does not know anything about the variable densities of this construct. There are two different saws available: one that cuts effectively through wood only, and ineffectively through the cement. Also available is a second saw that cuts just as effectively through cement as wood. Which of these saws would improve a chance of producing a more precise cut? Proposed is a mixing of ultrasonic energy with the standard oscillating saw and the standard reamer. In effect any oscillating equipment used in orthopedics, including the saw, reamer, drill, and the like may be made more precise in its ability to cut and prepare bone with the addition of ultrasonic energy. This may feel dangerous and counterintuitive to some, however, the surgeon typically applies a moderate amount of manual pressure to the saw and reamers, without being aware, which occasionally causes tremendous skiving, bending and eccentric reaming. An instrument that does not requires the surgeon's manual force maybe significantly safer and as well as more precise and effective.

A further option includes disposition of a sensor in the shaft of the ultrasonic reamers and saws so that the surgeon can ascertain when hard versus soft bone is being cut, adding a measure of safety by providing a visual numerical feedback as to the amount of pressure being utilized. This improvement (the ability to cut hard and soft bone with equal efficacy) will have tremendous implications in orthopedic surgery. When the acetabular cavity is prepared more precisely, with significantly lower tolerances, especially when directionality is observed, the acetabular implant (cup) may more easily follow the intended sinking path.

Other applications of this concept could be very useful. Pressfit and ingrowth fixation in total knee replacements in particular (as well as ankle, shoulder and other joints to a lesser degree) are fraught with problems, particularly that of inconsistent bony ingrowth and fixation. The fact that a surgeon is unable to obtain precise cuts on the bone may be a significant factor in why the bone ingrowth technology has not gotten off the ground in joints other than the hip. The problem is typically blamed on the surgeon and his less than perfect hands. The experienced surgeon boasts that only he should be doing this operation (i.e.: non-cemented total knee replacement). This concept (a more precise saw that cuts hard and soft bone equally allowing lower tolerances) has huge potential in orthopedics, in that it can lead to elimination of the use of cement in orthopedic surgery altogether. This can spark off the growth and use of bone ingrowth technology in all aspects of joint replacement surgery which can lead to tremendous time saving in the operating room and better results for the patients.

In addition to the incorporated parent applications, embodiments of the present invention may include aspects of resistive force measurement, resistive force curves, and BMD tools that include force sensing, such as described in U.S. patent application Ser. No. 15/234,782 filed 11 Aug. 2016 which claims benefit of the incorporated '434 Patent Application as well as U.S. Patent Application No. 62/355,657 and U.S. Patent Application No. 62/353,024 and also described in U.S. patent application Ser. No. 15/284,091, all of which are hereby expressly incorporated by reference thereto in their entireties for all purposes.

These applications include a description of a resistive force for insertion of a hemispherical acetabular cup into an under reamed cavity. This resistive force is sometimes referred to as the FR curve, defining a "cup print" for the insertion parameters. This resistive force has been described as being variable with three distinct sections. It has a profile that may be described as an "exponential curve". There is an identification of an early section/part of this FR curve where poor insertion and pull out forces exist. There is an identification of a middle section (a sweet spot) on this FR curve where good insertion and extraction forces are achieved. And, finally, the discussion describes that using larger forces beyond the sweet spot provide little additional benefit to the strength of fixation, and may increase a risk of fracture. In one analogy, this FR curve may represent a dangerous peak such as Mount Everest having five base camps. In the discussion, there is an observation that an orthopedic surgeon should be content to stop at base camp 3 or 4, and perhaps should not attempt to summit, when trying to obtain press fit fixation of the cup in an under-reamed cavity. This phenomena has been described in association with BMD3 and BMD4.

There is a very serious problem in orthopedics. Some of the incorporated patent applications discuss trunnionosis in connection with material regarding "BMD4" and "Intelligent Prosthesis Two". There are fundamental problems related to trunnionosis in orthopedics, specifically on the insertion of a femoral and humeral head onto the trunnion and the related problems that have been so far described as tribocorrosion. There many who believe that the mechanism of taper corrosion is best characterized as mechanically assisted crevice corrosion. Fretting initialed crevice corrosion in tapers is a complex problem and the severity is dependent on multiple factors. Corrosion has been associated with clinical complications, such as elevated metal ion levels, persistent pain, tissue damage, and early implant failure.

Regardless of the design, including shorter and slimmer trunnions and larger heads, as well as taper angles (including positive and negative mismatch) there appears to be some universal problems with the process of head impaction onto the trunnion that have to do with "taper impaction technique" and the "engagement of the modular taper interface" that doom the trunnion interface to failure.

Described herein are problems associated with head/trunnion impaction and possible solutions. Vibratory insertion of a prosthetic acetabular cup is extended here in that some of the same fundamental problems associated with mallet based impaction techniques of the prosthetic acetabular cup are present here with head/trunnion impaction.

Noted below are four specific and fundamental problems with current techniques of head to trunnion impaction:

A) Inconsistent magnitude of force. The force is delivered by a surgeon using a mallet. There is no standardization of magnitude of force. There is no guidance as to how much force needs to be delivered. The medical device companies have not done In Vitro studies to determine how much force to deliver for a good seal. There is no a priori information as to what type of force produces a desired "cold weld", which appears to be what we need to accomplish strong fixation with no micro-motion.

B) Inconsistent direction of force. Non-axial alignment of force is the norm for head to trunnion impaction. This produces "canting" which leads to micro motion and corrosion.

C) Impacting against a soft object. The impact is not "elastic" but "inelastic" or plastic. The kinetic energy produced by the surgeon and the mallet is mostly lost in a system that is inelastic. Momentum is conserved in that much of the energy produced by the surgeon and the hammer is dissipated by the spring like quality of the whole leg/femur/thigh/prosthesis complex. But kinetic energy is not conserved, with most of the energy lost by the system described above, and therefore, the transfer of energy from the head to trunnion interface is highly inefficient.

D) Assuming a surgeon is able to get the right amount (magnitude) of force delivered with the right technique (perfectly axially), How do you know you have actually achieved a "cold weld"? How do you know when to stop application of Force? No In Vitro studies have ever been done to guide the surgeon as to how much force to apply. Also, a proper tool have never been provided to the surgeon to accomplish this job.

The solution may include a new design with several key features.

1) A head may include a flat edge that allows it to sit flat on a table. A "head holder" may grasp the head in a 'normal' fashion on the flat edges. On an opposite side of the head holder a center axis point may be created, which allows ONLY central axis application of force.

2) The force as will be described can be delivered dynamically through controlled impaction as with BMD4 technique (e.g., various slide hammer configurations), or vibratory insertion as with BMD3 techniques or with Constant insertion (to allow the system to mostly deal with friction (e.g., a coefficient of kinetic friction $U_k$).

3) The prosthesis may have either indentations, holes, or ridges created in it to allow an insertion apparatus (BMD5) to purchase and grasp the prosthesis. This is a way to avoid unnecessary loss and waste of kinetic energy.

4) A force sensor/torque wrench/strain gauge within the tool measures the force experienced within the tool/head/trunnion/prosthesis complex.

5) An amount (magnitude) of force required to obtain a perfect weld can be determined in vitro. The force can be delivered with controlled impaction, vibratory insertion, or constant insertion. The force sensor may, in some implementations, act much like a torque wrench (possibly) stopping the application of the perfectly tuned force (both magnitude and direction) when a cold weld is obtained. Little to no dissipation of force/energy may occur in this system. The inconsistencies that are introduced by the surgeon and the mallet with current techniques are eliminated entirely. Since the surgeon is told in advance how much force to deliver and given the proper tool to accomplish this job, it is impossible to deliver less than required force. Since the tool only applies perfectly axial force, no canting can occur. Since the head and trunnion are now coupled/constrained in one physical system, wasting of kinetic energy will reduced or eliminated. The insertion of the head onto the trunnion is now done with a technologically intelligent and reliable system.

Figure 18:
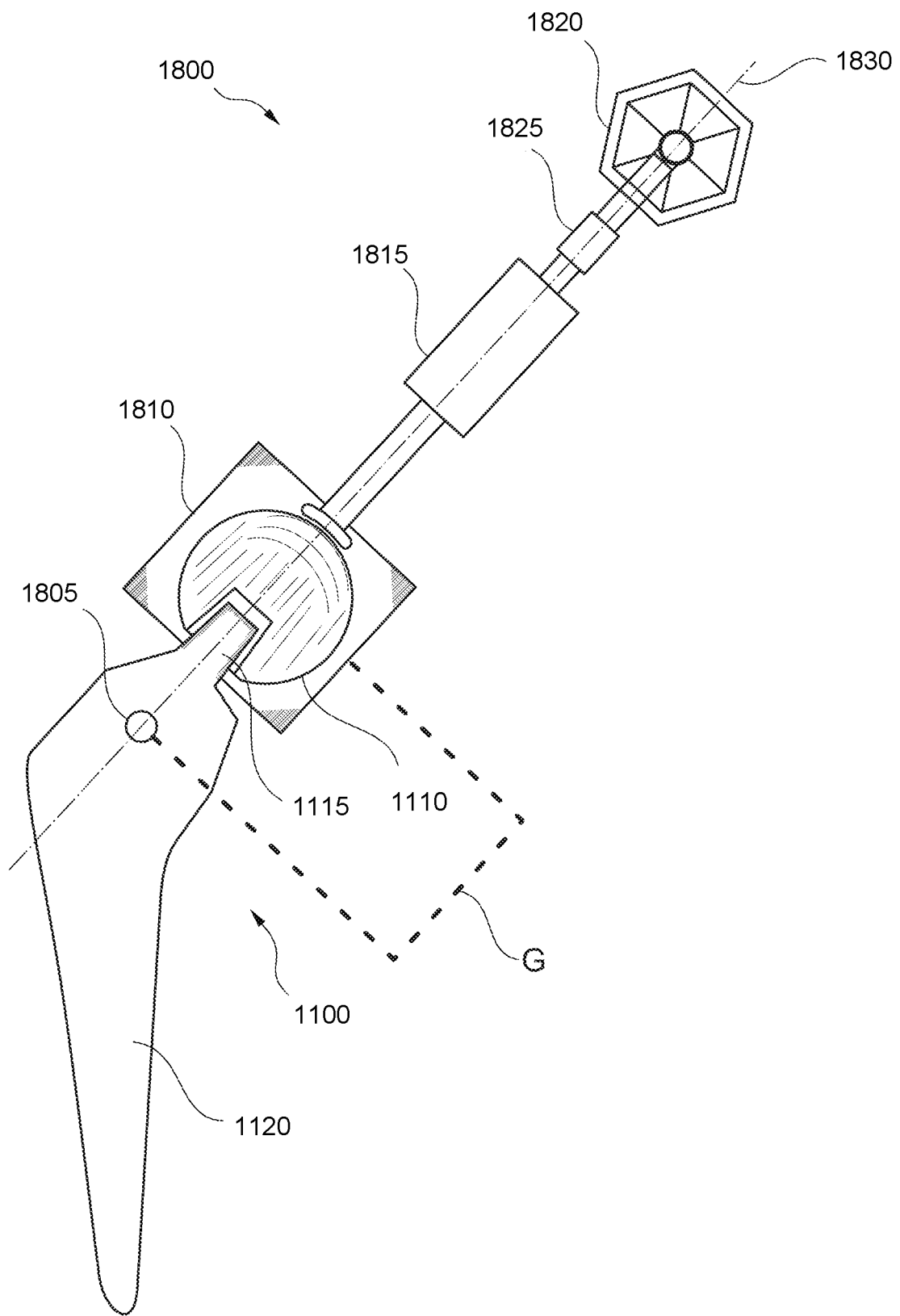
FIG. 18 illustrates a first embodiment for a BMD5 tool.
Figure 19:
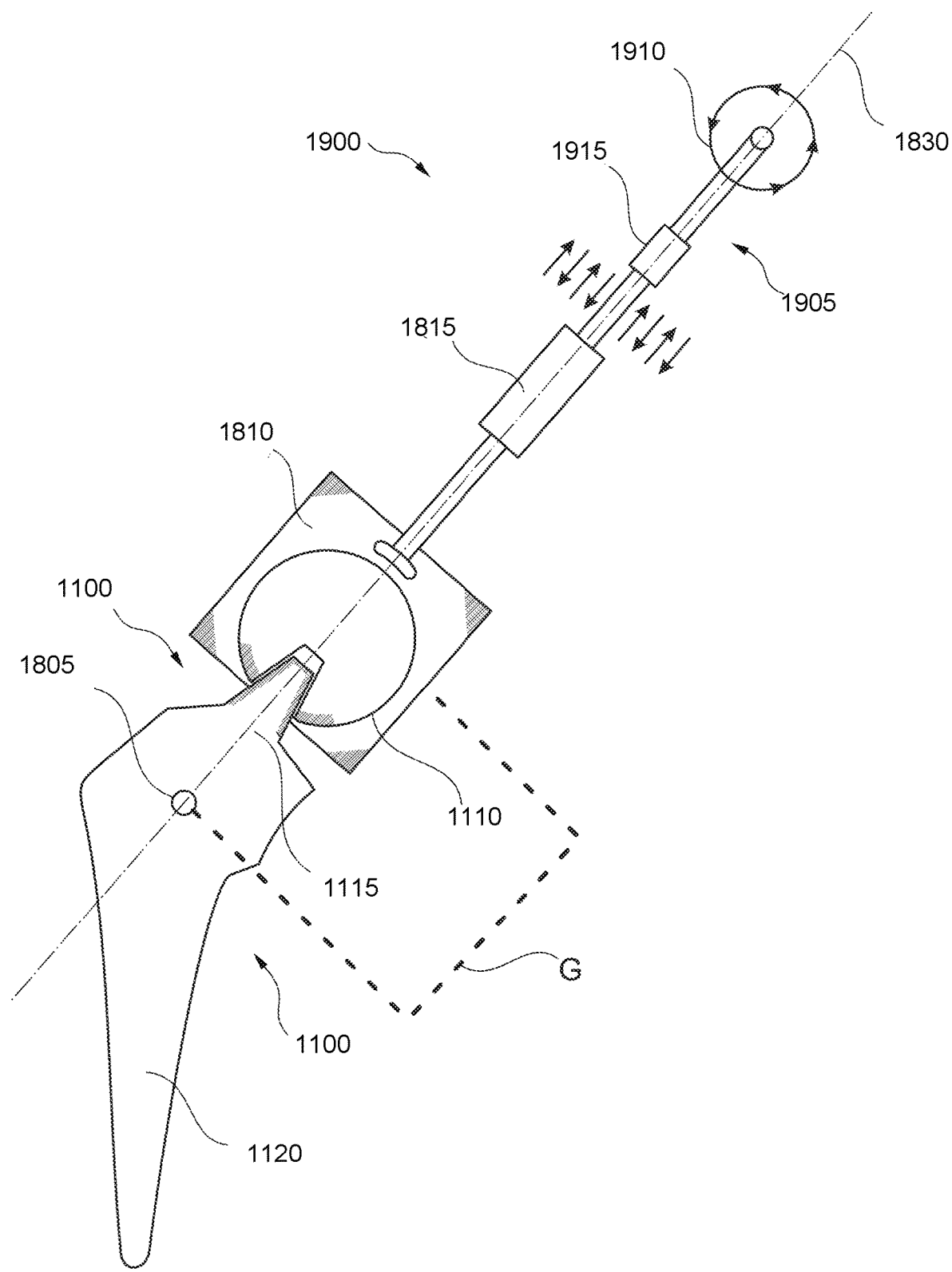
FIG. 19 illustrates a second embodiment for a BMD5 tool.
Figure 20:
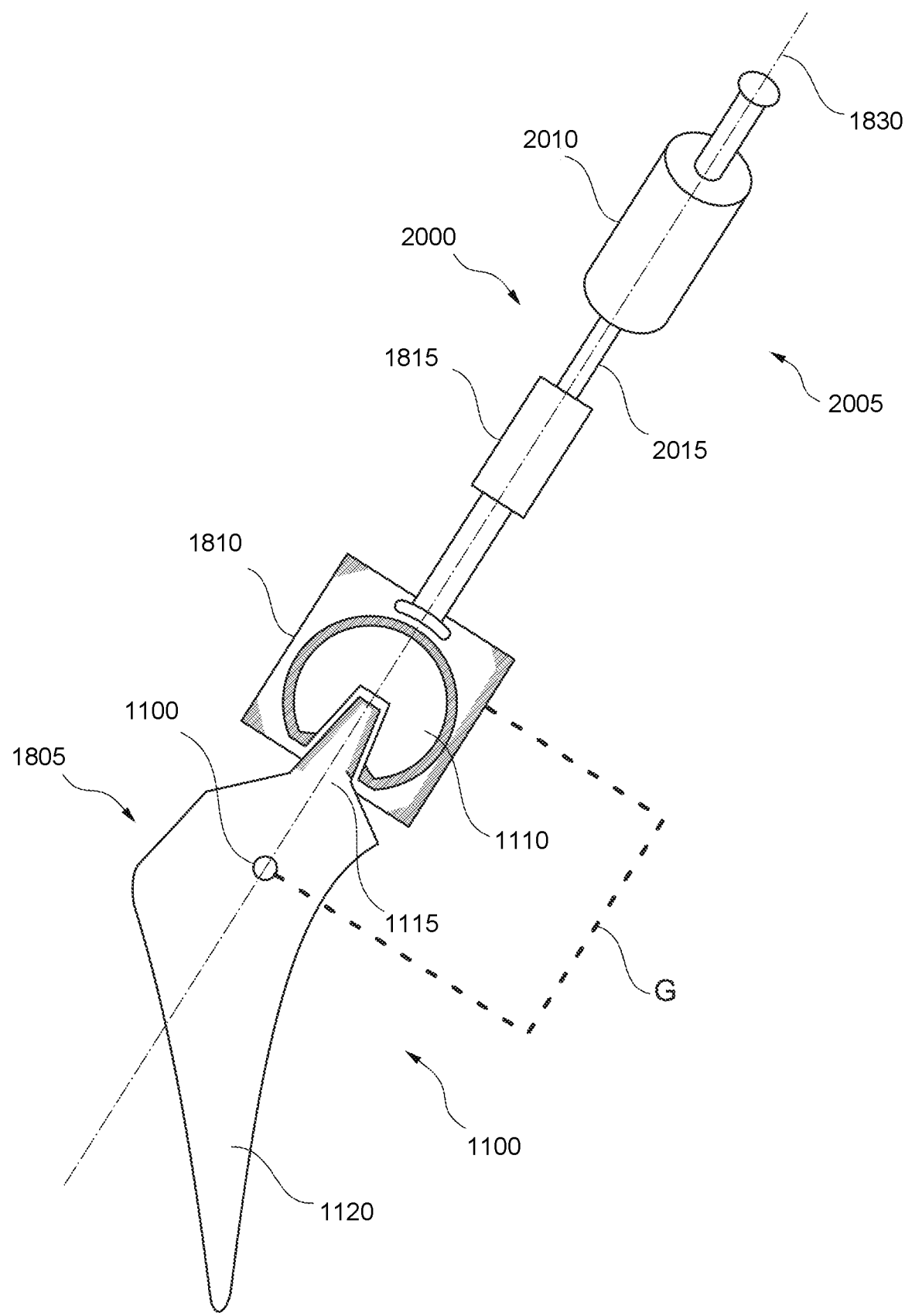
FIG. 20 illustrates a third embodiment for a BMD5 tool.

In each of FIG. 18-FIG. 20, an embodiment of a BMD5 tool will be used to help assemble a modular prosthesis. This is similar to the discussion of FIG. 11. In FIG. 11, modular prosthesis 1100 was assembled using assembly tool 1105 while in these discussions, a BMD5 tool replaces tool 1105 (with an optional modification to prosthesis 1100). Prosthesis 1100 includes a head 1110 and a trunnion taper 1115 at an end of a stem 1120 (e.g., a femoral stem for supporting a ball head to fit within an acetabular cup used in a total hip replacement procedure). During some embodiments of this alternative procedure, the surgeon assembles prosthesis 1100 by using a BMD5 tool. The surgeon uses the BMD5 tool to drive, and cold weld, head 1110 onto trunnion taper 1115.

FIG. 18 illustrates a first embodiment for a BMD5 tool 1800 used in cooperation with assembly of modular prosthesis 1100 to install head 1110 onto trunnion taper 1115 at an end of stem 1120. Prosthesis 1100 is modified to include a grip structure 1805 (e.g., an indentation, hole, cavity, aperture, and the like) to allow engagement of a retention structure (e.g., a claw, grasper, gripper, and the like—represented by G) coupled to both tool 1800 and to prosthesis 1100. Optional grip structure 1805 may be used to reduce or eliminate wasting of kinetic energy during assembly and welding of head 1110 onto taper 1115.

BMD5 tool 1800 includes a head grasper 1810, an in-line force sensor module 1815, a torquer 1820, and torque converter 1825. Head grasper 1810 retains and aligns head 1110 into an optimum installation orientation (e.g., perpendicular/normal) to allow application of force only along an assembly axis 1830 joining, and aligned with, grip structure 1805, head 1110, taper 1115, grasper 1810, module 1815 and torque converter 1825. This alignment allows for only force application only along assembly axis 1830 which prevents/reduces canting. Gripper G is illustrated as being functionally connected to grasper 1810, but could be mechanically communicated to another portion or component of tool 1800. This is a functional representation as there may be several mechanical ways to implement this function, including allowing relative displacement of the grasper and trunnion while maintaining the desired alignment(s).

Grasper 1810 is important in positioning (including alignment and relative orientation) of head 1110 and trunnion 1115. Head 1110 includes an aperture, typically complementary to the taper of a mating surface of trunnion 1115. Grasper 1810 secures head 1110 for assembly in a very simple and efficient manner that positions, without relative canting, head 1110 and trunnion 1115.

Module 1815 may include a torque wrench/strain gauge allowing a surgeon to understand one or more forces in play, such as knowing exactly how much force needs to be, and is being, delivered to obtain perfect cold weld of head 1110 onto taper 1115.

Torquer 1820 may include a manual or motorized source of force or torque, such as a torque engine which may include a rotary motor.

Torque converter 1825 transforms torque of torquer 1820 into axial-exclusive linear force for module 1815. When the torque engine provides rotary force, converter 1825 may include a linear motion converter to alter the rotary force into an axially-aligned linear force.

In operation, femoral head 1110 may be joined to trunnion taper 1115 using constant insertion. That is, head 1110 is "press-fit" with a constant (but potentially variable) axial force. This is distinguished from application of one or more discrete impacts or impulses onto grasper 1810. Constant insertion strongly implicates Uk (coefficient of kinetic friction) which may be less than a series of discrete impacts that more strongly implicate a coefficient of static friction. In some cases, stem 1120 is installed into bone and thereafter tool 1800 is used to install head 1110 onto the taper of trunnion 1115 to obtain a sufficient mechanical connection. Herein, that mechanical connection is sometimes referred to as a "cold weld" which for purposes of this application means that head 1110 and trunnion 1115 are engaged enough that relative micro-motion is eliminated or sufficiently reduced that risks of relative micro-motion are reduced below a predetermined threshold.

This is one aspect of the present invention, that a manufacturer of modular prosthetics may develop, or share, information on the forces necessary to produce a cold weld as noted above. Without recognition of the problems noted herein and a BMD5 tool to measure and/or control assembly forces and a surgeon swinging uncalibratingly a mallet to freely strike head 1110 and drive it onto trunnion 715, there was insufficient need or motivation to develop or share this type of information.

FIG. 19 illustrates a second embodiment for a BMD5 tool 1900 used in cooperation with assembly of modular prosthesis 1100 to install head 1110 onto trunnion taper 1115 at an end of stem 1120. Tool 1900 varies from tool 1800 in that tool 1900 performs insertion using a vibration profile. The vibration profile is provided by a vibration engine 1905 that may include a rotary motor 1910 coupled to a linear motion converter 1915 to impart a vibration to head grasper 1810 (and then to head 1110) to insert and cold weld head 1110 onto trunnion taper 1115. There are other ways to implement vibration engine 1905.

In operation, tool 1900 may join head 1110 to taper 1115 with a vibratory force (implicating a blend of static and kinetic coefficients of friction—Us and Uk), which may require less force than a series of discrete/dynamic impacts onto head 1110.

FIG. 20 illustrates a third embodiment for a BMD5 tool 2000 used in cooperation with assembly of modular prosthesis 1100 to install head 1110 onto trunnion taper 1115 at an end of stem 1120. Tool 2000 varies from tool 1800 in that tool 2000 performs insertion using an impact profile. The impact profile is provided by an impact engine 2005 that may include a slide hammer 2010 having an axially-limited sliding mass to impart a discrete impact onto a shaft 2015 and by that mechanism to head grasper 1810 (and then to head 1110) to insert and cold weld head 1110 onto trunnion taper 1115. There are other ways to implement impact engine 2005, including manual, mechanized (e.g., robotic), and semi-mechanized solutions.

In operation, tool 2000 may join head 1110 to taper 1115 with a series of one or more discrete impacts from impact engine 2005 (implicating predominantly/exclusively static coefficient of friction Us).

In summary BMD 5 is a tool that:

1. Advantageously modifies a femoral prosthesis in such a way to allow a grasp or engagement of the prosthesis by the BMD5 tool. This can be accomplished in a variety of ways: A hole, dent, ridges, and indentations can be created on the prosthesis. The ability to grasp the prosthesis is important in some embodiments in that it prevents, or reduces, waste of kinetic energy.

2. The BMD5 tool may include a "head grasper" which holds the femoral or humeral head in a perpendicular or "normal" fashion. This allows the force of insertion/impaction to be applied perfectly axially, without the risk of "canting".

3. The BMD5 tool has a torque wrench/strain gauge/force sensor of a wide variety of possible types that measures an amount of force applied through the tool/head/trunnion/prosthesis complex. The surgeon will always know exactly how much force is being applied. The amount of force required to obtain a perfect "cold weld" can be predetermined in the laboratory. The surgeon can simply apply the force that is recommended by the medical device company to obtain a perfect cold weld every single time, eliminating all variability that is currently present with application of force with variable surgeon strengths and mallet sizes.

4. For Constant insertion, manual or motorized rotatory motion is converted into linear motion with any linear motion converter. In a simple form, the rotatory motion of a screw/thread is converted into linear compression. For Vibratory insertion, similarly, rotatory motion by a motor is converted into linear vibration. For Discrete Impacts a sliding mass of known weight can travel over a known distance to deliver a predetermined amount of force.

BMD5 may include a self-contained system that reduces any wasting of energy. BMD5 may allow for perfect axial delivery of force while providing for quantitative measurement of applied/communicated/transmitted force(s). So stakeholders can rest assured that every step has been taken to obtain a cold weld at the trunnion/head interface. Embodiments of BMD5 may allow a surgeon to cold weld the femoral head onto the trunnion simply, efficiently, and accurately while minimizing risks of improper installation. Some embodiments of BMD5 may include ultrasonic press-fitting, such as described in Csaba LAURENCZY et al., "ULTRASONIC PRESS-FITTING: A NEW ASSEMBLY TECHNIQUE" S. Ratchev (Ed.): IPAS 2014, IFIP AICT 435, pp. 22-29, 2014, hereby expressly incorporated by reference in its entirety for all purposes.

Figure 21:
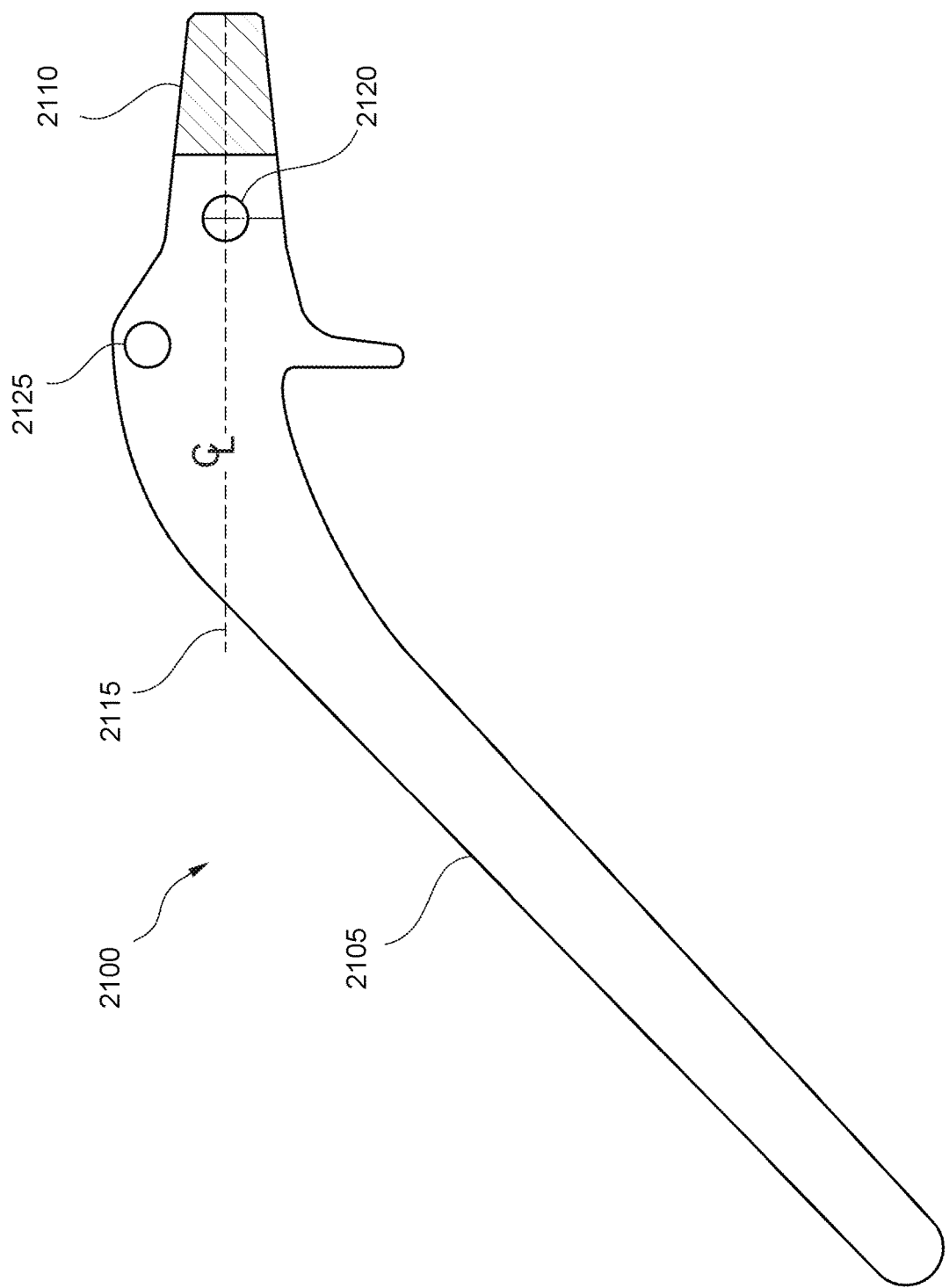
Figure 37:
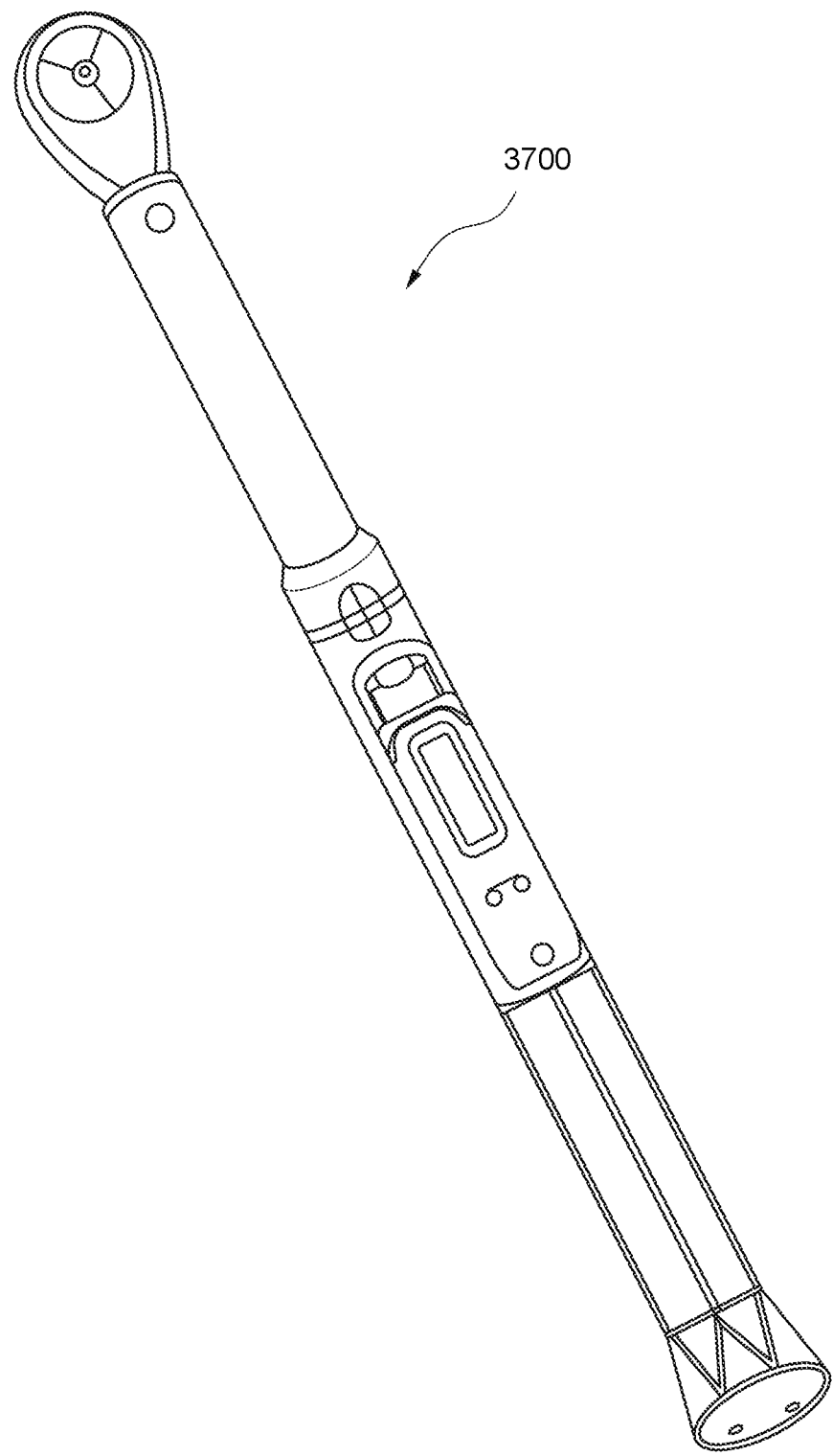

FIG. 21 through FIG. FIG. 37 illustrate a particular implementation of a mechanical alignment system for use with an embodiment of a BMD5 tool, such as, for example, those illustrated and/or described herein. FIG. 21 illustrates a side view of a prosthetic body 2100 to be mechanically joined to an installable prosthetic head. Body 2100 includes a stem portion 2105 for insertion into a prepared bone and a taper portion 2110 for mechanical joinder to a selected installable prosthetic head. A center line 2115 is defined as a central axis of taper portion 2110. Taper portion 2110 may include a two-dimensional symmetry along a length of center line 2115. The installable prosthetic head will include a complementary taper cavity that may further match this two-dimensional symmetry over a depth of the taper cavity along a taper cavity center line. Maintaining an alignment of these center lines as the prosthetic head is mechanically joined to taper portion 2110 may reduce, minimize, and/or eliminate canting or dangerous installation conditions that may contribute to or exacerbate any trunnionosis related to assembly of the prosthetic head onto taper portion 2110. Body 2100 may include, as a grip structure, a non-traditional through-hole 2120 centered on center line 2115 proximate taper portion 2110.

In some embodiments, grip structure 2120 may not be a through hole but may include, for example, laterally opposed divots with each centered on center line 2115. In other embodiments, the grip structure may include a conventional non-center line aligned element 2125. An adaptor, jig, or engagement system cooperating with element 2125 may provide a predetermined offset to align such other assembly components with center line 2115.

Figure 22:
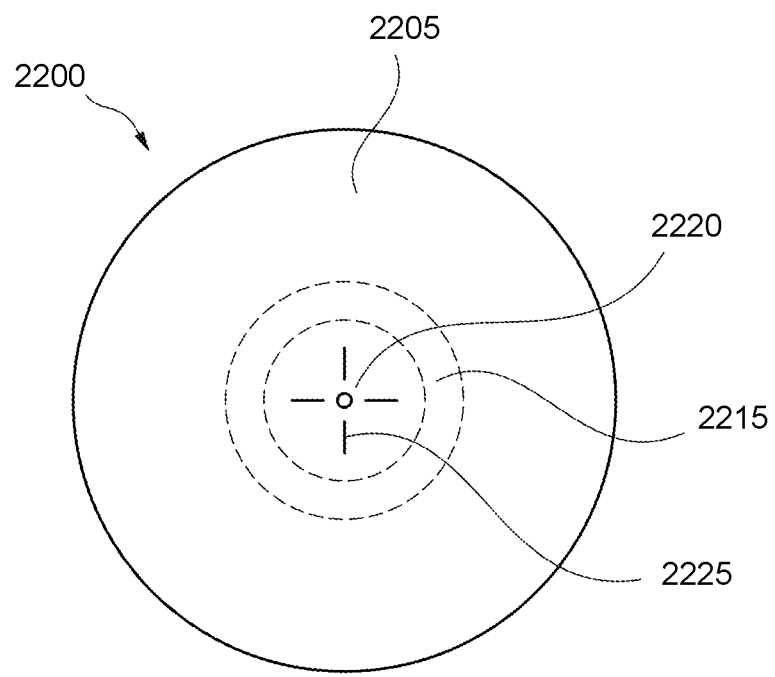
Figure 23:
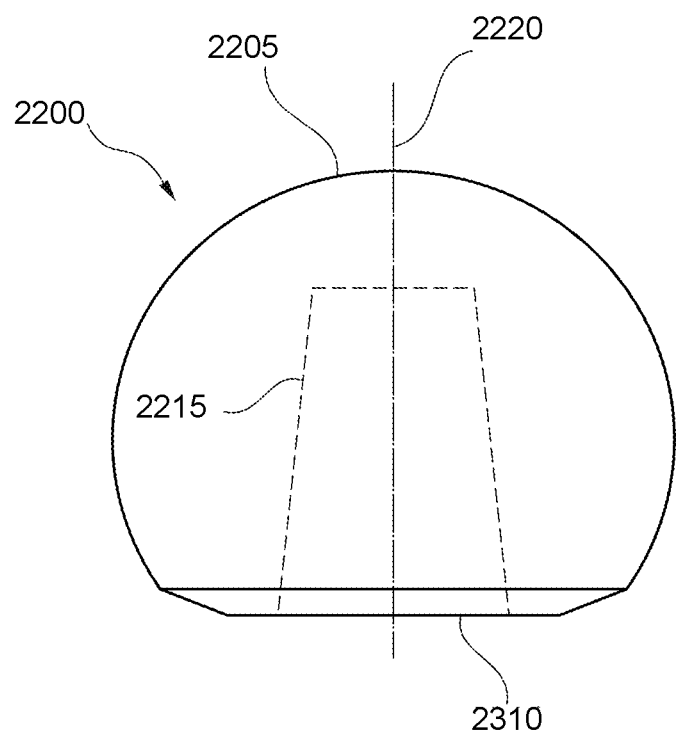

FIG. 22 and FIG. 23 illustrate a set of views of a prosthetic head 2200 to be installed on taper portion 2110 of prosthetic body 2100. FIG. 22 illustrates a top view of prosthetic head 2200 and FIG. 23 illustrates a side view of prosthetic head 2200. Prosthetic head 2200 defines an outer spherical surface 2205, at least a hemisphere, and further includes a planar face 2310, offset from but generally parallel to a diameter of the spherical portion of head 2200. An aperture is defined in planar face 2310, this aperture provides an opening into a taper cavity 2215 disposed within prosthetic head 2200. Taper cavity 2215 is designed to mate and engage with taper portion 2110 and in this sense is referred to herein as being complementary. Taper cavity 2215 also defines a taper cavity center line 2220 also having a two-dimensional symmetry along a depth of taper cavity 2215, and in some cases taper cavity center line 2220 is perpendicular to planar face 2310. An optional feature includes a marking, for example, a laser etch or other patterning modality, that applies a visible set of "cross hairs" 2225 centered on taper cavity center line 2220.

A goal of the supporting structures of some embodiments of the present invention may include configuring alignment of center line 2115 with center line 2220, maintaining that alignment while taper portion 2110 is mechanically joined with taper cavity 2215, and in some cases monitoring a magnitude of applied assembly forces to achieve a desired mechanical join (e.g., a cold weld or the like).

While the cross sections along a length of the center lines for both taper portion 2110 and taper cavity 2215 are circular, other cross sectional shapes may be employed without departing from the present invention.

FIG. 24 through FIG. 27 illustrate a set of views for an anvil 2400 intended to impart an assembly force to prosthetic head 2200 relative to prosthetic body 2100. FIG. 24 illustrates a side view of anvil 2400, FIG. 25 illustrates a top view of anvil 2400, FIG. 26 illustrates a bottom view of anvil 2400, and FIG. 27 illustrates a sectional view through anvil 2400 at A-A of FIG. 24. Anvil 2400 includes a solid body 2405 having a circumferential channel 2410 extending completely around an outside of a lateral sidewall of body 2405. Body 2405 includes a top face 2415 and a bottom face 2420 spaced apart from top face 2415 by the sidewall. A spherical sectional depression 2425 is defined in top face 2415. Depression 2425 is complementary to outer spherical surface 2205. Depression 2425 has a depth to position the planar face of prosthetic head 2200 into a predetermined relationship with top face 2415. In some instances, bottom face 2420 may define a tap or aperture 2605 that is centered at a longitudinal axis 2705 of body 2405 that extends through top face 2415 and bottom face 2420 and automatically aligns with taper cavity center line 2220 when prosthetic head 2200 is installed into mating depression 2425. Bottom surface 2420 supports an anvil axis interaction structure, such as tap or aperture 2605 and/or other structure, which may be used for visual confirmation of axial alignment with indicia 2220, or may be used for receipt of a force applicator, or some additional or other interaction with anvil 2400.

In some embodiments, aperture 2605, the optional structure, may extend from bottom surface 2420 into depression 2425. When so provided, and when prosthetic head is further provided with optional cross hairs 2225, it is possible to confirm alignment of axis 2705 with center line 2220 when cross hairs 2225 are visible in aperture 2605.

FIG. 28 through FIG. 32 illustrate a set of views of a multi-part adaptor 2800 for securing anvil 2400 to prosthetic head 2200. FIG. 28 illustrates a side view of multi-part adaptor 2800, FIG. 29 illustrates a top view of multi-part adaptor 2800, FIG. 30 illustrates a bottom view of multi-part adaptor 2800, FIG. 31 illustrates a sectional view through multi-part adaptor 2800, and FIG. 32 illustrates an enlarged view of FIG. 31. As illustrated, multi-part adaptor 2800 includes two half-shells (half-shell 2805 and half-shell 2810, each half-shell a mirror image of the other) though other configurations may provide for a different number of parts.

These are half-shells because they each include a rigid exterior wall cooperatively defining an interior cavity 3105 that is sized and configured to secure and hold prosthetic head 2200 within depression 2424 of anvil 2400 while center line 2225 is aligned with axis 2705. Adaptor 2800 defines a top face 2815 and a bottom opening 2820. Top face 2815 defines an aperture 2905 for receipt of taper portion 2110 when prosthetic head 2200 is installed into depression 2424 of anvil 2400 and both head 2200 and anvil 2400 are installed into cavity 3105.

Interior portions of the walls of adaptor 2800 further define an interior circumferential ledge 3110 that is designed to mate to circumferential channel 2410 when adaptor 2800 secures anvil 2400 and head 2200. A distance from ledge 3110 to top face 2815 is based upon a height of the planar face of head 2200 above depression 2424 when head 2200 is installed in anvil 2400 with axis 2705 aligned with center line 2225. By matching the distance to the height, top face 2815 will automatically align center line 2225 with axis 2705 when the half-shells are closed down on head 2200 and anvil 2400.

As further detailed in the enlarged view of adaptor 2800 in FIG. 32, aperture 2905 in top face 2815 may be formed with sloped edges to match an angle of taper portion 2110.

As illustrated, adaptor 2800 may be configured to a particular one size of prosthetic head 2200. When a differently sized prosthetic head 2200 is to be installed on taper portion 2110, a different adaptor 2800 may be used and in some embodiments, this is the only modification that need be made to the system to accommodate differently sized heads. Similarly, with proper attendance to the configuration options, different sized bodies may be matched to different sized heads by only varying adaptor 2800 in appropriate fashion.

FIG. 33 through FIG. 35 illustrate a set of views of a clamp 3300 for attachment to prosthetic body 2100 and apply an aligned assembly force to prosthetic head 2200 by use of the multi-part adaptor 2800. FIG. 33 illustrates a top view of clamp 3300, FIG. 34 illustrates an end view of clamp 3300, and FIG. 35 illustrates a side view of clamp 3300. Clamp 3300 includes a "U-shaped" body 3305 having a first leg 3310, a second leg 3315, and a bridge 3320 coupled to each leg. A distal end of each leg defines an aperture 3325 that are aligned with each other.

Bridge 3320 defines a force application structure 3330 for allowing an assembly force to be transferred from outside of clamp 3300 to a location disposed between the legs. In FIG. 34, structure 3330 includes a tapped/threaded interior surface to allow a complementary threaded bolt to pass into the location. FIG. 35 illustrates that in this implementation, structure 3330 is aligned (e.g., coplanar) with apertures 3325.

As noted herein, there may be many different types of assembly forces used and therefore the transfer structure may need to be adapted accordingly to accommodate the particular assembly force in use. For example, in some cases, a simple aperture may be used and other cases clamp 3300 may be part of a robotic system, among other variations.

Figure 36:
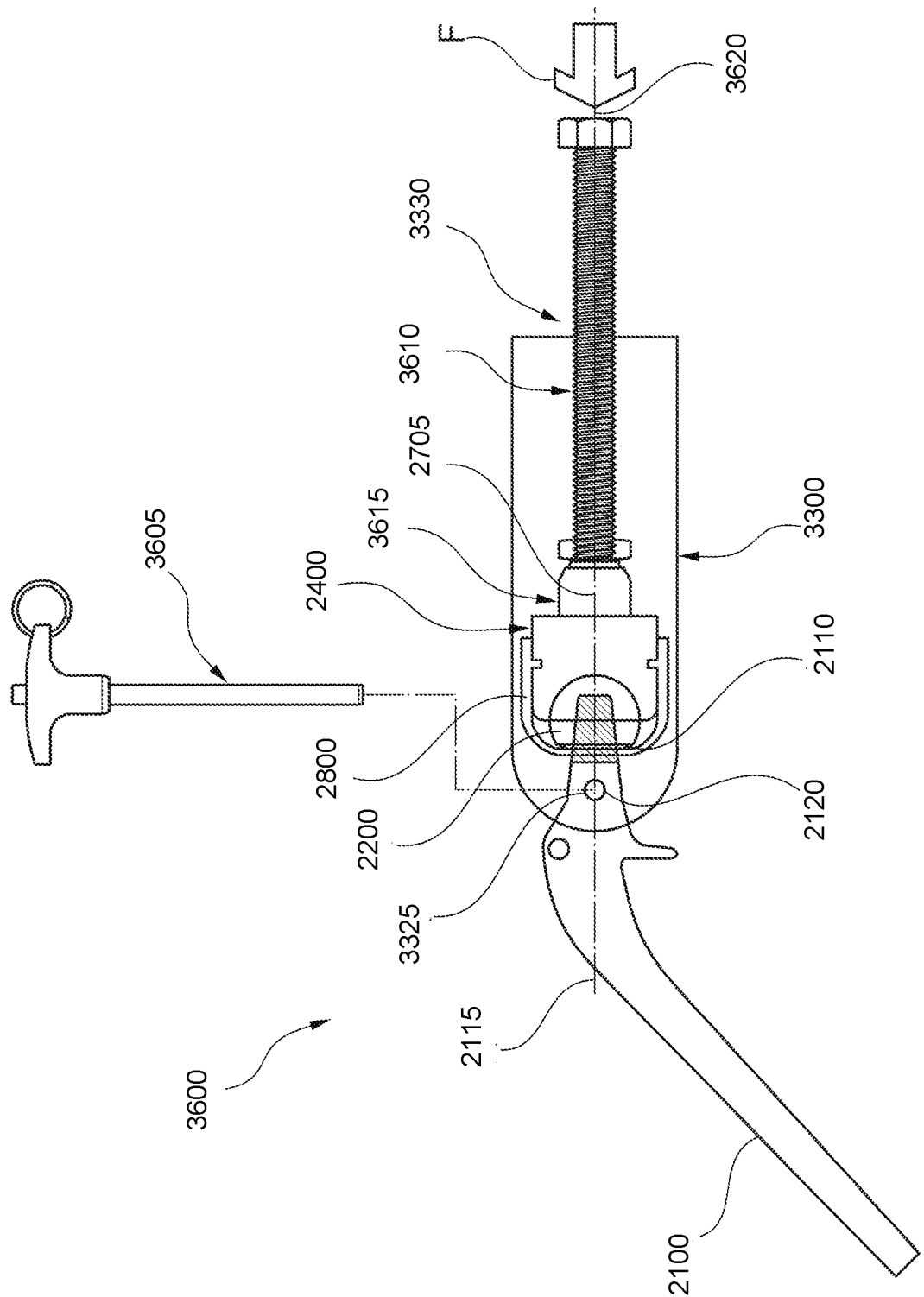

FIG. 36 illustrates a stackup view for a mechanical alignment system 3600 shown securing, aligning, and applying an assembly force F to prosthetic head 2200 to install it onto prosthetic taper 2110. A pin 3605 is illustrated that is passed through aligned apertures 3325 and structure 2120 which aligns to center line 2115 and secures the components to prosthetic body 2100.

A representative assembly force F is applied by use of a screw 3610 threaded through structure 3330. A pad 3615 at a distal end of screw 3610 contacts anvil 2400 and helps to distribute assembly force F when applied against the assembly including head 2200, anvil 2400, and adaptor 2800. Assembly force F, applied on a force application axis 3620 is automatically aligned with center line 2115 as is the taper cavity of head 2200.

As screw 3610 is rotated, it is advanced into the space between the legs of clamp 3300 which transfers assembly force F onto the assembly that includes prosthetic head 2200. Assembly force F causes head 2200 and taper portion 2110 to join together without tilting, canting, or off-axis torqueing impacts, such as is often applied from a mallet.

During joinder of head 2200 and taper portion 2110, as assembly force F increases at some point a desired mechanical join is achieved. In some cases, this mechanical join may include a desired cold weld with reduced risk of trunnionosis. As noted herein, in some cases it may be desirable to continue to increase assembly force F until a desired assembly force profile is achieved.

FIG. 37 illustrates a representative manual torque wrench 3700 which may be used with the system illustrated in FIG. 36 to apply a predetermined assembly force, or assembly force profile (e.g., Force F) to produce a desired mechanical join of prosthetic head 2200 onto prosthetic body 2100.

Figure 38:
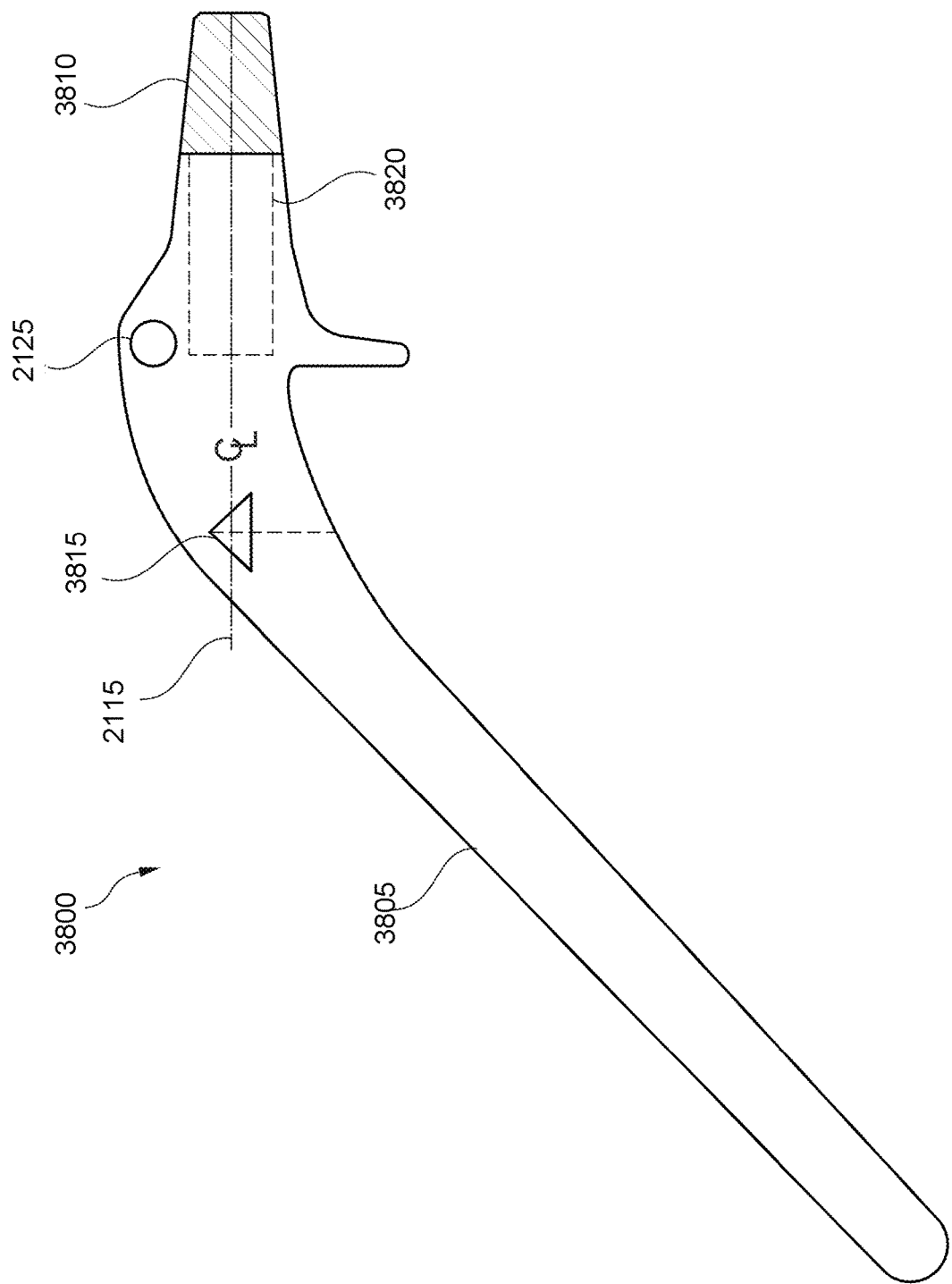
FIG. 38 illustrates a side view of an alternative prosthetic body to be mechanically joined to an installable prosthetic head.

FIG. 38 illustrates a side view of an alternative prosthetic body 3800 to be mechanically joined to installable prosthetic head 2200. Body 3800 includes a stem portion 3805 for insertion into a prepared bone and a modular taper portion 3810 for mechanical joinder to selected installable prosthetic head 2200. A center line 2115 is defined as a central axis of modular taper portion 2110. Modular taper portion 2110 may include a two-dimensional symmetry along a length of center line 2115. Installable prosthetic head 2200 will include a complementary taper cavity that may further match this two-dimensional symmetry over a depth of the taper cavity along a taper cavity center line. Maintaining an alignment of these center lines as prosthetic head 2200 is mechanically joined to taper portion 2110 may reduce, minimize, and/or eliminate canting or dangerous installation conditions that may contribute to or exacerbate any trunnionosis or tribocorrosion related to assembly of prosthetic head 2200 onto taper portion 2110 and installation of modular trunnion 3810 into body 3800. Body 3800 may include, as a grip structure, a non-traditional through-hole 3815 (or detent/depression/extension/pin or other physical structure centered on center line 2115.

In some embodiments, grip structure 3815 may not be a through hole on center line 2115 but may include, for example, laterally opposed divots with each centered on center line 2115. In other embodiments, the grip structure may include a conventional non-center line aligned element 2125 which may have optionally been provided for removal of body 3800 when installed. An adaptor, jig, or engagement system cooperating with element 2125 may provide a predetermined offset to align such other assembly components with center line 2115.

Differences between body 3800 as compared to body 2100 may include one or more of the following possible elements. Illustrated in FIG. 38 is use of modular taper portion 3810 in which the modular prosthesis may include three interchangeable elements: stem, trunnion taper, and head (FIG. 38) as compared to two interchangeable elements: integrated stem/trunnion and head (FIG. 21).

Modular trunnion taper 3810 may be a separate element that includes taper portion 3810 coupled to a trunnion extension 3820. Trunnion extension 3820 is designed to be inserted into and received and secured by a complementary trunnion extension channel defined in stem 3805. Trunnion extension 3820 may also include a center line and may also use an extension taper for mechanical joinder of modular trunnion taper onto stem 3805. The system described herein may be used to center and axially install modular trunnion taper 3810 into the channel of stem 3805. Modular trunnion taper 3810 may optionally include a visible indicia marking a center line of trunnion extension 3820 to aid in non-tilting/non-canting installation of extension 3820 into the channel of stem 3805.

As illustrated, a centerline of extension 3420 is aligned with center line 1715 of modular trunnion portion 3410 and grip structure 2120 or grip structure 3815 may be used for installation of both elements (extension 3820 into the channel and then head 2200 onto modular trunnion portion 3810 thereafter). Alternatively, extension 3820 may be provided with a grip structure and head 2200 first installed onto modular trunnion portion 3810 and then the subassembly of head 2200 and modular trunnion portion 3810 thereafter installed onto stem 3805.

In some cases, a more complex assembly system results when a center line of extension 3820 is not aligned with center line 2115 of modular trunnion portion 3810 but the system described herein may be suitably adapted for assembly, including but not limited to multiple grip structures aligned with each center line (or variable jigs for proper offset at each stage of assembly).

There are a number of functions may be achieved by the assembly system including establishment and maintenance of alignment of all axes during assembly, reduce inefficient use of assembly forces, and provide for measure of assembly force(s) used during assembly.

Reduction of inefficient energy usage may be achieved by the mechanical coupling of the two elements being joined (e.g., stem and head, stem and modular trunnion, head and modular trunnion, subassembly of head/modular taper and stem, and the like). This is contrasted to a conventional approach of installing a stem into a patient bone and then using a mallet to hammer a head onto the stem—some of the kinetic energy is absorbed by the bone, body portion, operating table, and the like. By mechanically linking one portion to the other during the assembly, this loss of assembly energy is reduced or eliminated.

Another function of establishment and maintenance of axial alignment may be achieved by awareness of axes and ensuring that these axes are aligned as assembly forces are applied. As noted, the various structures, systems, and processes described herein aid in the establishment and confirmation, in some cases this is done automatically, of alignment before and during application of force assembly. The definition and establishment of predetermined center line(s), fixing structures to these center line(s), and ensuring that appropriate axes are aligned to the appropriate center line(s) during application of the assembly force(s).

Body 3800 of FIG. 38 differs from body 2100 of FIG. 21 not only from the description of the optional modularity of the trunnion portion, but further illustration of an optional use of a non-circular grip structure. Grip structure 2120, as implemented in FIG. 36, allows clamp 3300 to rotate about pin 3605 because pin 3605 may act as axle or pivot. In some cases, such as when there is some misalignment of an application of force to the center line(s) of center line 2115. This misalignment may contribute an undesired tilting, canting, or other non-aligned assembly.

Body 3800 provides grip structure 3815 with an irregular perimeter that inhibits or prevents rotation. As illustrated, grip structure 3815 includes a polygon (e.g., an N-sided regular polygon, N an element of an integer set {3, 4, 5, 6, 7, 8, 9, 10, 11, 12, or more} of sides, N=3 for in FIG. 38. The irregular perimeter need not be a regular polygon, it may be an irregular polygon. In other instances, it may be an oval, oblong, ovoid, or other non-circular perimeter.

In other implementations, anti-rotation may be provided by use of two or more grip structures that are spaced apart from any other grip structure, when the multiple grip structures are used concurrently during application of an assembly force. One or both of these grip structures may include a circular perimeter.

As illustrated, the prosthesis bodies (body 2100 and body 3800) are illustrated for use in shoulder (e.g., humerus) and hip (e.g., femur) modular prosthetic assemblies. There are other modular prostheses systems in which there are mechanical joinders of multiple prosthesis components. Whenever there are two prosthesis components that must be mechanically joined together, some embodiments of the present invention may be applied to axial assembly of these other modular prosthesis systems. For example there are modular systems for knee, ankle, wrist and other joints and skeletal systems that may benefit from use of the present invention when a body (not limited to a stem or the like) is joined to another modular component.

Regarding ultrasonic assisted bone preparation in orthopedics, there is a problem with preparation of bone in joint replacement: these procedures are typically performed using conventional orthopedic equipment such as 1) saw, 2) broach, 3) reamer, and 4) burr.

Figure 39:
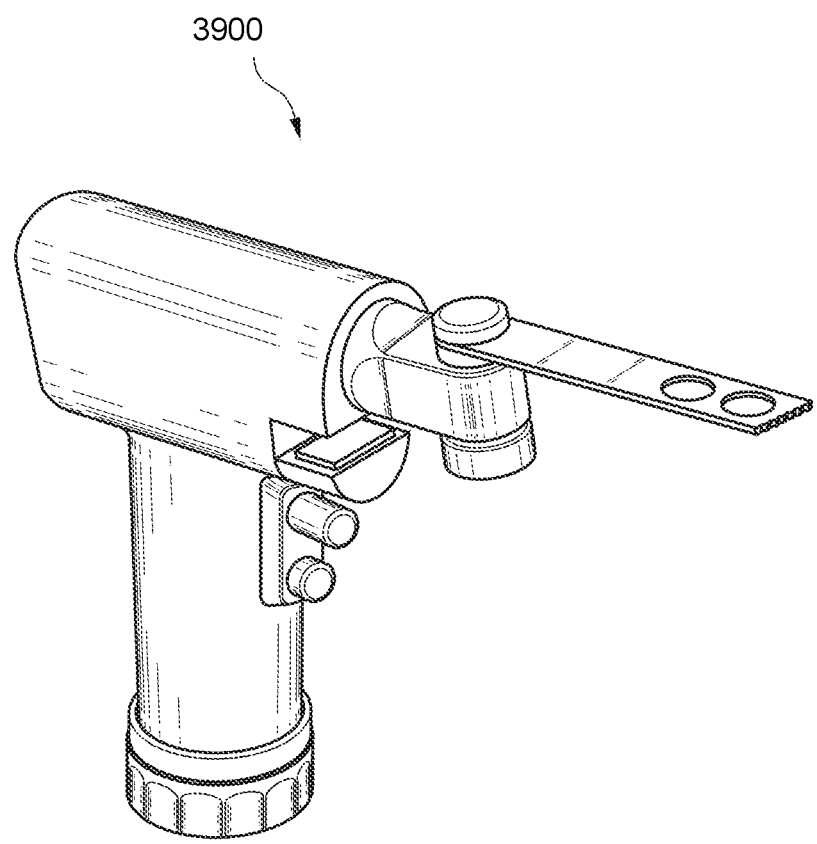
FIG. 39-FIG. 42 illustrate a set of standard orthopedic bone preparation tools.
Figure 40:
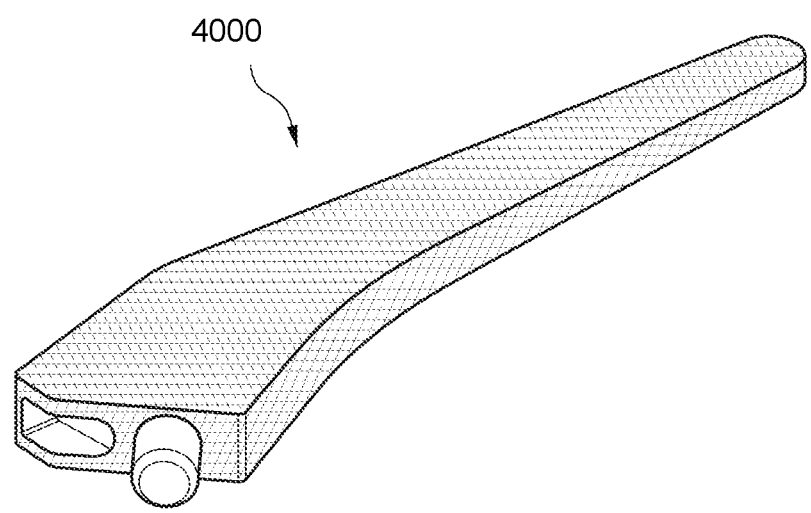
Figure 41:
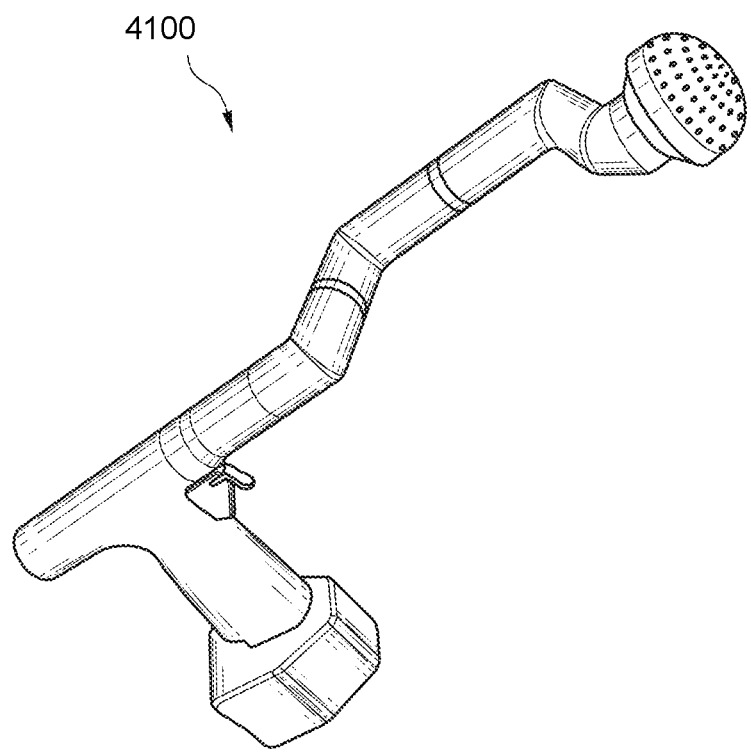
Figure 42:
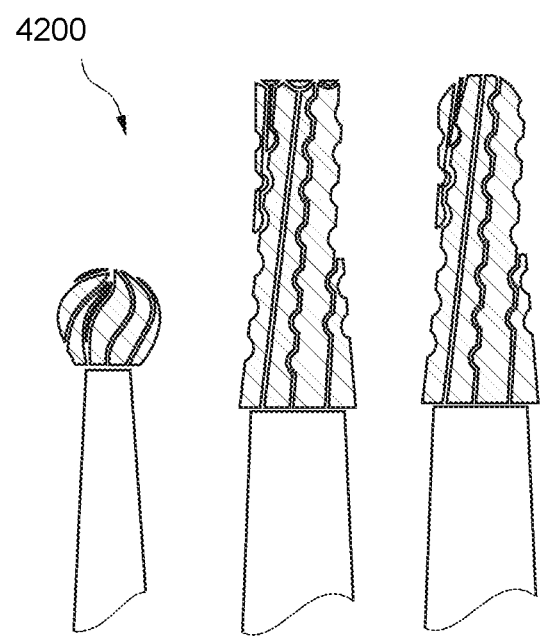

FIG. 39-FIG. 42 illustrate a set of standard orthopedic bone preparation tools, FIG. 39 illustrates a perspective view of a powered bone saw 3900, FIG. 40 illustrates a broach attachment 4000 for a powered reciprocating bone preparation tool (a surface including a set of cutting, abrading, bone removing structures), FIG. 41 illustrates a hand-operated reamer 4100, and FIG. 42 illustrates a set of bone preparation burrs 4200. Conventionally, these tools include an operating motion with one degree of freedom (e.g., saw 3900 has a blade that moves laterally, broach attachment 4000 reciprocates longitudinally, reamer 4100 and burrs of set of burrs 4200 each rotate about a longitudinal axis).

As noted below, these bone preparation tools may be enhanced by adding an additional vibratory motion component, preferably but not necessarily required, that is "orthogonal" to the conventional cutting motion. Saw 3900 includes a laterally reciprocating cutting blade that may be ultrasonically enhanced by an additional ultrasonic vibratory motion in one of the other five degrees of motion (e.g., vertical, longitudinal, or vibratory rotations of the blade such as pitch, yaw, and/or roll). Similarly each of the conventional tools has a primary mode of freedom of motion for the bone processing and an enhancement may be made by adding an additional vibratory motion in one or more other modes of freedom. Embodiments of the present invention may include an additional vibratory motion, in the primary mode and/or the additional mode(s) that may be imperceptible visually (a very small amplitude and/or very fast about or beyond 20,000 hertz).

During bone preparation, two types of bony surfaces are generally encountered which include flat surfaces and contained surfaces. For the flat surfaces, seen in knee replacement, (end of the femur or the top of the tibia) saw 3900 is used to cut the bone. For the contained surfaces (such as the acetabulum and the proximal femur), as in hip replacement surgery, broach attachment 4000 or reamer 4100 is used to prepare the bone.

A problem with all of these techniques is that the density of the bone is not uniform between patients and even within the same compartment or joint of a single patient. The bone can be very soft or very hard and vary from region to region. With hard bone, saw 3900 may "skive" which causes an uneven cut surface and which minimizes that chance of successful "porous ingrowth". This fact may be a principle reason that cement is still used in knee replacement. For the contained bone cavities such as the acetabulum and proximal femur a "goldilocks" situation exists. During preparation, a surgeon may desire to know how with confidence to prepare the bone to provide just the right amount of compressive (fit). Not too loose and not too tight. Too loose leads to loosening and potential infection of the prosthesis. Too tight leads to either poor seating (which can lead to failure of fixation) or fracture (which leads to loss of press fit fixation and loosening).

Current art does not provide a reliable and consistent tool or method for the orthopedic surgeon to reliably prepare a (variable density bone) in order to obtain a "perfect" fit for the prosthesis, whether the bone is flat as in the tibia in knee replacement or contained as in the acetabulum in hip replacement.

For contained cavities such as the acetabulum, U.S. patent application Ser. No. 15/234,782 filed 11 Aug. 2016 (all the content hereby expressly incorporated by reference thereto in its entirety) described a basic estimation of the compressive forces involved in bone. This was named a compressive force and developed an FR curve where FR is related Fn. Us; where Fn represents the normal forces and Us represents the coefficient of static friction. Vis a vis Hooke's law the FR=K. x. Us. Where K represents the material properties of bone (the spring like quality of bone) and x represents the amount of under-reaming of bone compared to an oversized prosthesis intended for press fit.

This current discussion mostly concerns itself with the variable "x" which represents the spring like quality of bone. In Hooke's law F=k. x; k is the spring's constant and x is amount of stretch placed on the spring. In orthopedic bone preparation k is represented by the material properties of bone and x is represented by the difference between the diameters of the prepared bone versus the prosthesis to be press fit.

As we have stated in the earlier papers, the surgeon and industry both appear to have a poor understanding of the basic science of the prosthesis/bone cavity interaction. It is believed that x can be more tightly and precisely machined to give a better tuning of the bone, which is to accept an oversized prosthesis.

BMD3 bidirectional vibratory tool for preparation of bone, and in particular the acetabular cavity: The use of a Acetabular Broach: a new idea. BMD3 bi-directional vibratory tool can be used for preparation of bone (any cavity of bone that needs to be prepared for application of a prosthesis, but especially the acetabulum, as well as the proximal femur, proximal tibia, proximal humerus, and any other long bone in the body that receives a prosthesis). With regards to the acetabulum, unlike the other bones discussed above, this structure has never before been prepared with a broach, but rather always prepared with a hemispherical "cheese grater type" reamers that rotates in one direction (forward). We are proposing that the acetabulum be prepared with a broach using one of the two degrees of freedom for oscillation (1. Longitudinal and 2. rotational), utilizing a bidirectional BMD vibratory tool. The outer surface of this broach will very closely resemble the rough surface of the prosthesis, with high coefficient of static friction. We have seen this method in action in our experiments, particularly at higher frequencies of around 300 hertz, and believe that this method of acetabular preparation will provide a cut surface that is much more precise and conferring the ability to produce lower tolerances. This method may also allow preparation of acetabular cavity in "half" sizes. Currently the cavity is reamed in 1 mm intervals. It may be much easier to prepare the acetabulum with ½ mm interval broaches than ½ mm reamers. Half size broaching may dramatically improve the ability of the surgeon to cut and prepare the acetabular precisely and at lower tolerances.

For purposes of review we recall the equation FR=K. x. Us. Where x is represents the amount of under reaming and the shape of the cup being inserted.

X is controlled by the amount of under or over reaming of the acetabulum. In the past when the surfaces of the cup were not as rough (lower coefficient of static friction, i.e. Zimmer Fiber Metal cup), surgeons used to under ream by 2 mm. Now most companies recommend under reaming by 1 mm, since the surfaces of most cups are much more rough with better porosity characteristics that allow better and quicker bony ingrowth. Sometimes when the surgeon has difficulty seating the cup, he/she reams line to line, and describes this action as "touching up the rim". This action however, many times, eliminates the compressive quality of the acetabulum by decreasing the value of x towards zero. This issue brings attention to the problem that we have described which is that the surgeon does not have anything but a most basic understanding of the spring like qualities of bone. If he/she is can understand the basic science involved in this system, he can then use the proper tools to appropriately fine tune the pelvis for a good press fit fixation, without fear of under seating or fracture. There is a huge market need for better tools to prepare (fine tune) the acetabulum, for good press fit fixation.

Current techniques utilize 'cheese grater type' hemispherical reamers to prepare the bed of the acetabulum. As discussed in our BMD4 paper the quality of acetabular bone can be drastically different between patients and even within the same patient, particularly at different locations around the acetabular fossa. Some parts of the bone are soft, and some are hard. Current cheese grater hemispherical reamers come in 1 mm intervals. This creates two specific problems: 1. The current acetabular reamers in 1 mm intervals for preparation of the acetabular bone do not provide the ability to precisely machine the acetabulum, and obtain lower tolerances, and therefore proper tuning of the pelvic bone. 2. No method exists to cut hard and soft bone with the same level of effectiveness, i.e.: hard bone always pushes the reamers towards the soft bone which ends up being chewed up more, and in that sense, a perfect hemisphere is not created with current cheese grater reaming techniques. We therefore are proposing two distinct and separate solutions which we believe can remedy this problem of poor quality acetabular preparation.

1. The creation of half reamers. The production and use of half reamers gives the surgeon the ability to ream up or down by half millimeters. Which gives him/her the ability to fine tune x more precisely, and therefore FR more precisely. This basically gives the surgeon a better set of tuning forks to obtain better tension for the acetabulum and utilize its viscoelastic properties to his/her advantage to obtain a better press fit fixation.

2. Ultrasonic assisted reaming or broaching: Lastly, we believe that there is some room for creating a better cutting tool by adding ultrasonic energy to either the acetabular broach described above or the acetabular half reamers described above to create an ultrasonic assisted reaming or broaching of the acetabulum for obtaining a more precise cut and at a lower tolerance. We believe this is a new and novel idea that can be considered for preparation of the acetabulum for obtaining better tension of the pelvis for application of an acetabular prosthesis.

The following further elaborates upon ultrasonic assisted preparing, milling, burring, sawing, broaching, reaming, and the like in order to obtain a more precise and efficient process of bone preparation in joint replacement surgery.

Another important advance in orthopedics is the use of robotics in the operating room. Sensors and computer-controlled electromechanical devices are integrated into a robot with a haptic sense, where robotic manipulators now have a complete spatial sense of the patient's bone in the operating room, sometimes to within a half millimeter of accuracy.

Currently robots such as the Stryker Mako robot use a standard rotating burr, reamer or a standard saw to prepare the bone for application of a knee or hip prosthesis. The term "robot" has a special meaning in the context of preparation of live bone in a living patient. Currently it is impermissible to automate any cutting of the live bone. Robot in this sense operates as a realtime constraint that provides haptic feedback to the surgeon during use when certain movements of the processing tool are outside predetermined limits.

An advantage of the robot is that it is helps in processing bone to within less than half a millimeter. This means that the surgeon cannot easily push the burr, reamer or saw out of the allowed haptic plane. In a sense, with the robot, the cutting tool is in safer hands. These standard tools (burr, saw, reamer) provide no particular advantage for the robotic system, that is, the conventional robotic system uses conventional tools with the constraint haptic system. A disadvantage of the robot is that the process of cutting bone with a burr, saw and reamers are very inefficient (slow) especially in hard sclerotic bone. The robot is also very a bulky piece of equipment that adds time to the operation. Mako or other robotic knee surgeries have been somewhat adopted in the uni-compartmental knee replacement procedures (less than 10% of surgeons), and is currently being investigated for use in total knee replacement (Not yet in general markets). The use of the Mako robot in hip replacement however, has shown a very poor adoption rate; less than 0.01% of surgeons have used the Mako robot for hip replacement. Some of the weakness of this robotic procedure is in the process of 1. bone preparation and 2. the actual insertion of the prosthesis into bone.

Earlier tools have addressed tools for installing an acetabular cup into the bony cavity with either "vibratory-BMD3" technique or "discrete impact-BMD4" technique. These solutions are believed to largely eliminate the problems associated with insertion of the prosthesis, providing the ability not only to insert but also to position the prosthesis in proper alignment. Other tools have dealt with manipulating the value of Us, coefficient of static friction, during a process of insertion.

An embodiment of the present invention may include a better job of preparation of bone. In effect, some embodiments provide a tool or process that more precisely manipulates the value of x in the formula: FR=K. x. Us. A goal of some embodiments of the present invention is to obtain lower (tighter tolerances) and do it more quickly, with different tools and methods such as disclosed herein.

An embodiment of the present invention may include bone preparation using robotic surgery through use of haptic control and management to provide an unprecedented level of safety and accuracy coupled with modified equipment that more efficiently prepares in-patient bone while offering novel solutions for bone preparation. In some of these implementations the robotic haptic feedback may be exploited by addition and utilization of a more powerful and efficient bone cutting tool/method never before used or contemplated in orthopedics as it would have been too easy to mis-process a bone portion.

Ultrasonic motion may be added to traditional bone processing tools (e.g., to the tools of FIG. 39-FIG. 42) to offer effective non-traditional bone processing tools. This addition of ultrasonic energy to standard cutting, milling, reaming, burring and broaching techniques can be used to provide (methods and tools) in orthopedic surgery to remove bone more effectively with a (higher material removal rate) MMR and with significantly less force, and therefore more efficiency.

Specifically, in hip replacement surgery the traditional reamer, broach or burr can each be equipped with an ultrasonic transducer to provide an additional ultrasonic vibratory motion (e.g., longitudinal axial ultrasonic vibration). These new cutting methods can then be incorporated within, or in association with, a robot that only allows operation of the tool within safe haptic zones. This ultrasonic robotic cutting tool is therefore more powerful, fast and precise. It would cut hard and soft bone with equal efficiency. Additionally, the robotic operation of an ultrasonic assisted cutting tool is safe, in that the robot does not allow operation of the tool outside of the haptic safe planes.

For example, a Mako robot may be equipped with a rotatory ultrasonic bone preparation tool, operating a bone processing tool (such as single metal-bonded diamond abrasive burr) that is ultrasonically vibrated, for example in the axial direction while the burr is rotated about this axis. This tool can prepare both the proximal femur and acetabulum quickly with extreme precise. This tool and method therefore does away with the standard manual broaching techniques used for femoral preparation and the standard reaming techniques used for acetabular preparation.

An implementation of this system of a constrained ultrasonic vibration of a bone processing tool such as a rotating burr enables a three-dimensional bone-sculpting tool or a smart tool robot. The sculpting tool and smart tool robot may allow a surgeon to accurately, quickly, and safely provide non-planar contours when cutting bones as further described below while also potentially replacing all the conventional preparation tools of FIG. 39-FIG. 42.

The addition of the ultrasonic bone preparation tool to a robot makes the system a truly efficient and precise tool. The surgeon can sculpt the surfaces of the bone, for example a femur, tibia or an acetabulum and the like, and in some implementations any tissue may be sculpted with the sculpting tool, with high degree of accuracy and speed.

With current tools, it would take too much time to perform such bone preparation with a burr, making the operation extremely slow and adding risk to the patient and is therefore not performed. Some implementations include an addition of an improved bone processing tool to any haptically constrained system will make the preparation of bone for joint replacement easy, fast and efficient, ultimately delivering on the promise of a better, faster and more precise operation.

With respect to knee and shoulder replacement, some of the bone surfaces are flat which have led to prosthetic designs that have a flat undersurfaces, and the decision to prepare these bones with a saw. One concept is to add ultrasonic axial vibrations to the saw for a more effective cut.

Ultrasonic enhancement may be added to all current bone removal techniques in orthopedics, including the burr, saw, reamer, and the broach, making all of these bone preparation tools more effective.

In some instances, use of the same burr described above (e.g., a rotating tool with metal-bonded diamond abrasives that is ultrasonically vibrated in the axial direction) to prepare surfaces of the tibia, femur and the glenoid in the shoulder for mating to an implant surface. One important benefit of use of such a burr is that the surgeon and the smart tool robot can now very quickly and effectively machine these mating surfaces any way desired, potentially introducing waves and contours that can match the undersurface of the prosthesis (which itself has been created with waves and contours for additional stability. Portions of the tibia and the glenoid in the shoulder are flat bones that do not have inherent stability. These bones are prepared in such a way to accept a prosthesis with a flat surface. With the advent of high-power 3D bone sculpting, 3D printing, and smart tool haptic constraint, the sculpting/smart tool system may create prostheses that have waves and contours on their bottom surface to enhance stability when mated. For example, a bone surface may be 3D sculpted/contoured and a prosthesis produced to match the profile or a preformed contoured prosthesis may be provided with a non-flat profile and the mating bone surface may be sculpted/contoured to match the preformed non-flat prosthesis mating surface, particularly for the "flat ended" bone and the associated prostheses. These contouring profiles for bone and implant mating surfaces are not limited to "flat ended" bones and may have benefit in other implants or bone mating surface.

These changes can enhance the initial fixation of the prosthesis to bone by creating a contact surface areas which are more resistant to shear forces. This may provide a specific advantage for the tibial component in knee and the glenoid component in shoulder replacement surgery. These prostheses generally have flat undersurfaces and are less inherently stable. They can be made significantly more stable with the suggested changes in the method of bone preparation and prosthesis fabrication.

FIG. 43 illustrates a side view of a first set of components 4300 for a conventional bone preparation process and FIG. 44 illustrates a side view of a second set of components 4400 for a three-dimensional bone sculpting process that may be enabled by some embodiments of the present invention.

Components 4300 include a bone B (e.g., a tibia) having a flat end 4305. Flat end 4305 is typically removed by a conventional version of saw 3900, to allow an implant 4310 to be installed. In the conventional process, bone B is prepared having a flat/planar bone mating surface 4315 which matches a flat/planar implant mating surface 4320 of implant 4310. As noted, the pair of mated surfaces may exhibit instability, especially with lateral shear loading.

Components of 4400 include bone B that has been prepared differently by removing flat end 4305 using an orthopedic sculpting system as described herein. The sculpting system enables use of an implant 4405 that includes a contoured (non-flat/planar) implant mating surface 4410. A bone mating surface 4415 produced by the orthopedic sculpting system is contoured to match/complement implant mating surface 4410. Components 4400 may include a preformed implant 4405 and surface 4415 is sculpted to match/complement for bonding or surface 4415 is sculpted and surface 4410 is thereafter formed to match/complement surface 4415. An additive/subtractive manufacturing process may be used to make surface 4410 and/or implant 4405. For example, implant 4405 may include two portions—a premade head portion and a later-formed body portion that may be contoured or manufactured as needed to produce surface 4410, with the head portion and body portion joined together to produce implant 4405

Bone ingrowth technology has not enjoyed that same success in shoulder and knee replacement surgery as it has done in hip replacement surgery. One reason that this may be true is because current methods do not allow precise and uniform preparation of bone due to variable density of bone, and especially on the flat surfaces. The ultrasonic assisted bone preparation (example, the orthopedic sculpting system or smart tool robot) discussed herein has a potential to solve this problem of inconsistent bone preparation. The use of the above bone preparation method/tools instead of the standard techniques may represent a disruptive technology. The ability to quickly machine bone, and to do it in an extremely precise and safe manner may eliminate the need for bone cement in joint replacement surgery. This fact can cause an explosion in the use of porous ingrowth prosthesis/technology in orthopedics joint replacement surgery.

Figure 45:
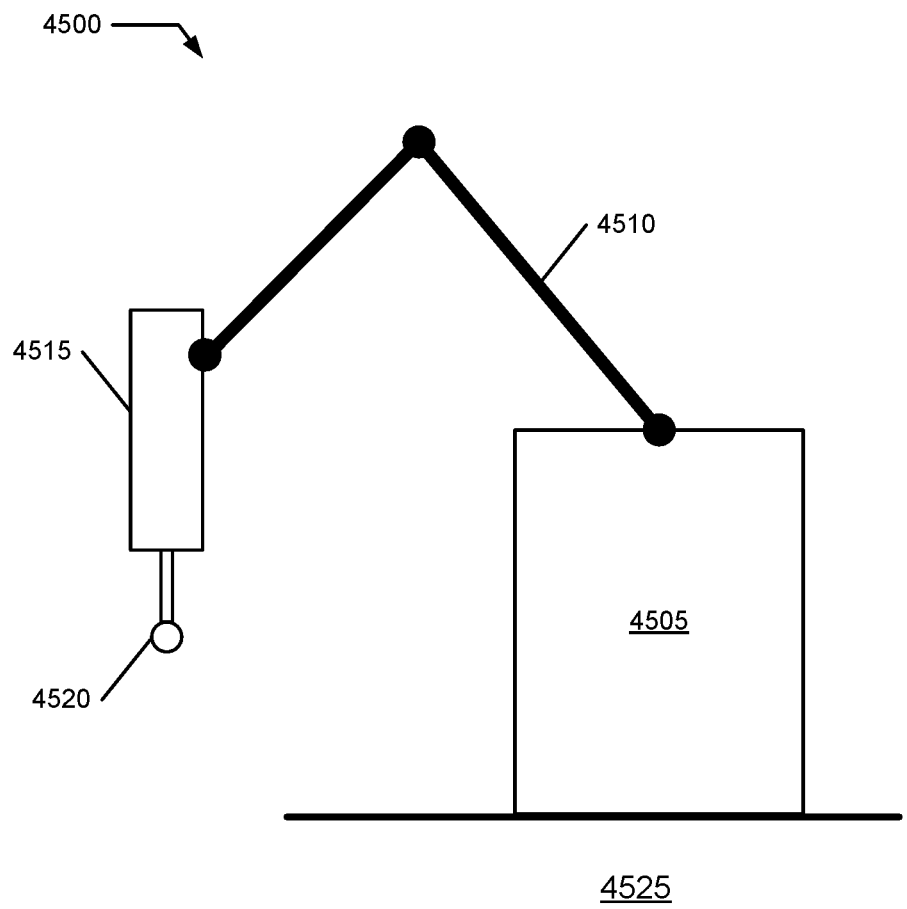
FIG. 45 illustrates a plan diagram of a smart tool robot.

FIG. 45 illustrates a diagram of a smart tool robot 4500 which may include a type of three-dimensional bone processing tool. Robot 4500 includes a local controller 4505 coupled to a linkage 4510 which is coupled to a high-efficiency bone processing tool 4515, with tool 4515 including a bone interface implement 4520. Controller 4505 includes systems and methods for establishing and monitoring a three-dimensional spatial location for implement 4520. Controller 4505 further includes governance systems for linkage 4510. Collectively controller 4505 and linkage 4510 may be a type of constraint, other systems and methods for another type of constraint and providing feedback may be included in some embodiments of the present invention. Linkage 4510 may include a set of sensors for a set of parameters (e.g., navigational, positional, location, force, and the like) and controller 4505 may include systems to access and read the set of parameters from linkage 4510. Alternatively, or in addition, controller 4505 may include a set of sensors producing a set of parameters. In some implementations, the set(s) of parameters may include information regarding forces, location, orientation, and motion of tool 4515 and/or implement 4520. In some embodiments, these set(s) of parameters may include information and data relative to a portion of bone 4525 that is to be processed using interface 4520 of tool 4515. Controller 4505 is secured, constrained, and/or fixed to portion of bone 4525. In some cases, controller 4505 may be optional and linkage 4510 may be secured, constrained, and/or fixed to portion of bone 4525. Any sensors or functions associated with controller 4505 may be omitted and/or distributed among linkage 4510 and/or tool 4515 and/or interface 4520.

Linkage 4510, illustrated as including a mechanically limited articulating arm, is coupled to both optional controller 4505 and tool 4515 (or to portion of bone 4525). In some cases when processing a particular in-patient bone, controller 4505 may predefine a set of bone regions of the in-patient bone for a processing (e.g., a cutting, a removing, a reaming, a sawing, a broaching, a burring, implanting and the like). Controller 4505 may monitor a relative location of interface 4520 relative to a particular portion of the in-patient bone to be processed and compare that particular portion with the predefined regions. Those predefined regions may include a first subset of regions to be processed by interface 4520 and in some cases also include (or alternatively substitute for the first subset) a second subset of regions not to be processed by interface 4520. Controller 4505 provides a realtime feedback to the user regarding an appropriateness or desirability of processing each the particular portion of bone at the location of interface 4520.

In some cases, the realtime feedback may include a realtime haptic signal imparted from controller 4505 through linkage 4510 to tool 4515. That haptic signal may be of sufficient strength to significantly restrict an ability of an operator to casually move interface 4520 to a region of the in-patient bone that is not to be processed, and some cases may essentially prevent or inhibit the locating of interface 4520 to those regions of the in-patient that are not to be processed.

Other feedback signals may be included in addition, or in lieu of, the haptic system. Audio feedback may in some cases be sufficient to provide feedback to an operator.

Tool 4515 may be an embodiment of an ultrasonically enhanced bone preparation tool which operates interface 4520. Tool 4515 includes a motive system that operates interface 4520 with a bone processing motion. The bone processing motion includes a primary motion having a primary freedom of motion (e.g., for a burr as illustrated, the primary motion may include a rotation about a longitudinal axis, this primary motion having a freedom of motion that includes the rotation about the longitudinal axis). The bone processing motion includes a secondary motion having a secondary freedom of motion, the secondary freedom of motion different from the first freedom of motion. The secondary motion includes an ultrasonic vibratory motion that enhances the bone-preparation of interface 4520 than would be the case of the primary motion alone. Other tools may include tools for preparation of implant site in portion of bone 4525 and/or installation of an implant into portion of bone 4525 and/or repositioning of a mal-positioned implant installed into portion of bone 4525.

Different implements and tools may include varying primary and secondary motions, there generally being six freedom of motion possibilities for the primary or secondary motions: x, y, and z translations and rotations about any of the x, y, and z axes. Typically the primary motion will include a repetitive (and sometimes reciprocating) component.

An operator grips tool 4515 and manipulates it by hand. Controller 4505 automatically monitors these manipulations to establish a relative location of interface 4520 with respect to a particular portion of an in-patient bone. Comparison of the relative location to predetermined/premapped regions of the in-patient bone that identify processable/non-processable regions results in controller 4505 is used to provide appropriate realtime feedback signals to the operator for each particular portion of bone.

Figure 46:
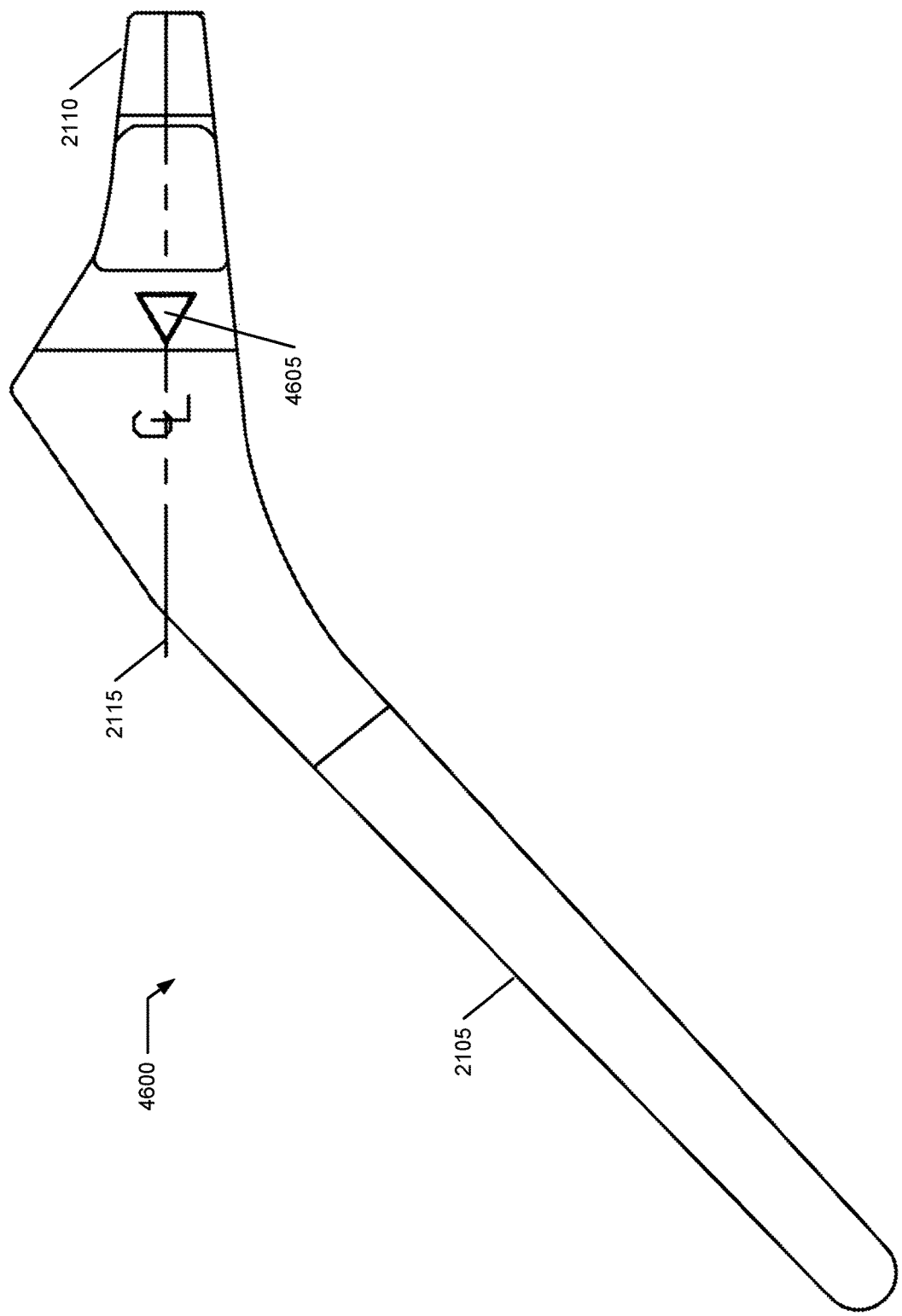
FIG. 46-FIG. 49 illustrate an alternative implementation of a mechanical alignment system.
Figure 47:
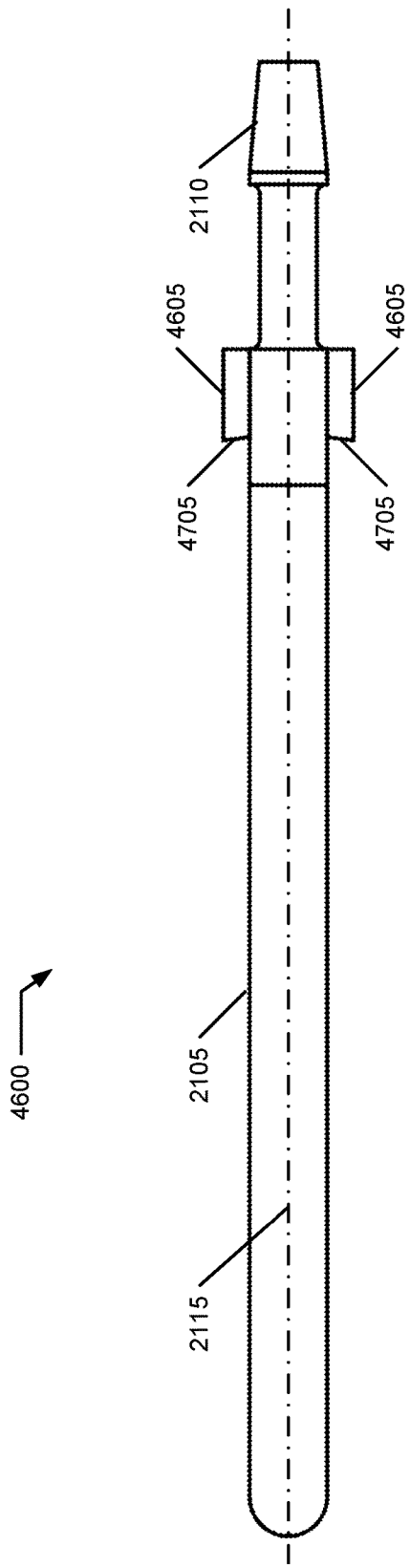
Figure 48:
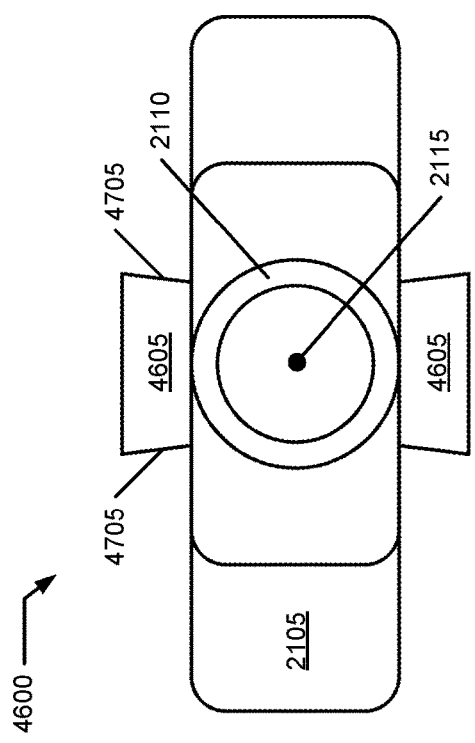

FIG. 46-FIG. 49 illustrate an alternative implementation of a mechanical alignment system similar to that described herein in connection with prosthetic body 2100 and clamp 3300, including the following differences. FIG. 46 illustrates a side view of an alternative prosthetic body 4600 to be mechanically joined to an installable prosthetic head (e.g., head 2200), FIG. 47 illustrates a top view of alternative prosthetic body 4600 and FIG. 48 illustrates an enlarged front view of alternative prosthetic body 4600.

Body 4600 includes stem portion 2105 for insertion into a prepared bone and taper portion 2110 for mechanical joinder to a selected installable prosthetic head. Center line 2115 is defined as a central axis of taper portion 2110. Taper portion 2110 may include a two-dimensional symmetry along a length of center line 2115. The installable prosthetic head will include a complementary taper cavity that may further match this two-dimensional symmetry over a depth of the taper cavity along a taper cavity center line. Maintaining an alignment of these center lines as the prosthetic head is mechanically joined to taper portion 2110 may reduce, minimize, and/or eliminate canting or dangerous installation conditions that may contribute to or exacerbate any trunnionosis related to assembly of the prosthetic head onto taper portion 2110. Body 2100 may include, as a grip structure, a non-traditional engagement element 4605 centered on center line 2115 proximate taper portion 2110.

Element 4605 includes a protrusion or an indentation into body 4600. Body 4600 may include one element 4605 on opposite sides. These element(s) 4605 may be the same (i.e., both protruding or indented) or they may be different (one protruding and one indenting). These grip structures are complementary to a mating grip structure on an engagement clamp used to join the installable head onto taper 2110. Element(s) 4605 is non-planar with surrounding portions of body 4600 (i.e., it extends or retracts relative to the surrounding portion) and is not a complete aperture/hole through body 4600.

Element 4605 includes a perimeter profile (illustrated in FIG. 46 as an equilateral triangle centered on centerline 2115 but may be an irregular or other regular triangle such as an isosceles triangle or the like). That profile may be any non-circular shape and in a special case, the profile may be circular in an event that elements on opposite side are not co-axial on centerline 2115 (e.g., one element 4605 is centered on centerline 2115 somewhat closer to taper 2110 than the other element 4605 on the opposite side of body 4600). The profile may include a regular or irregular polygon of N number of sides, N ∈ {3, 4, 5, 6, 7, 8, 9, 10, or more}, and may include an appropriate positive or negative dove tail on lateral portions of one or more walls as described herein, or other regular or irregular non-circular perimeter, or circular perimeters when opposing structures are not co-axial (all representative of structures preventing, inhibiting, and/or resisting having these grip structures act as an axle and allow rotation of the clamp out of centerline alignment(s).

In some embodiments, there may be particular arrangements or additional considerations for element 4605. As noted herein, a compatible clamp includes an engagement system compatible with element(s) 4605 which may be designed to mechanically join an installable prosthetic head onto taper 2110. This will include an application of force and it may be desirable to improve an interlocking interaction of such a compatible clamp and body 4600.

One way that this interlocking interaction may be improved is to provide dove tails on one or more engaging surfaces. Another way is for consideration of an orientation of element 4605.

FIG. 47 and FIG. 48 illustrate a dove tail 4705 on an extending wall when elements 4605 include a protruding element 4605. Further, as illustrated in FIG. 46, element(s) 4605 have a vertex of the equilateral triangle that is further away from taper 2110 aligned on centerline. In some embodiments, it may be preferred that dove tail 4705 is at a negative angle (an angle between an outermost surface and the extending wall is less than ninety degrees as illustrated in FIG. 47 and FIG. 48). For example, an angle may be less than fifteen degrees, preferably less than ten degrees, and in some embodiments about seven degrees. In some embodiments, a mating engagement structure for extending element 4605 on a compatible clamp may include a complementary cavity. That complementary cavity may include a positive dove tail.

A dove tail on a cavity wall when element 4605 includes an indenting element 4605 may also be provided—however in such cases it may be desirable to reorient the equilateral triangle so that one vertex is closest to taper 2110 and lies on centerline 2115. An embodiment including this arrangement may include indenting element 4605 generally equivalent to the complementary cavity described herein with the mating engagement structure of the compatible clamp including a complementary extending structure. The indenting element 4605 may thus have a positive angle dove tail and the mating engagement structure the negative dove tail, including the range of angles as described herein.

These dove tails help to create a locking interface between body 4600 and the compatible clamp as the aligned body and clamp force the head onto taper 2110. This locking interface helps to further resist rotations of the clamp relative to body 4600, among other potential advantages (in addition to the perimeter profile shapes and relative positioning of element(s) 4605).

Figure 49:
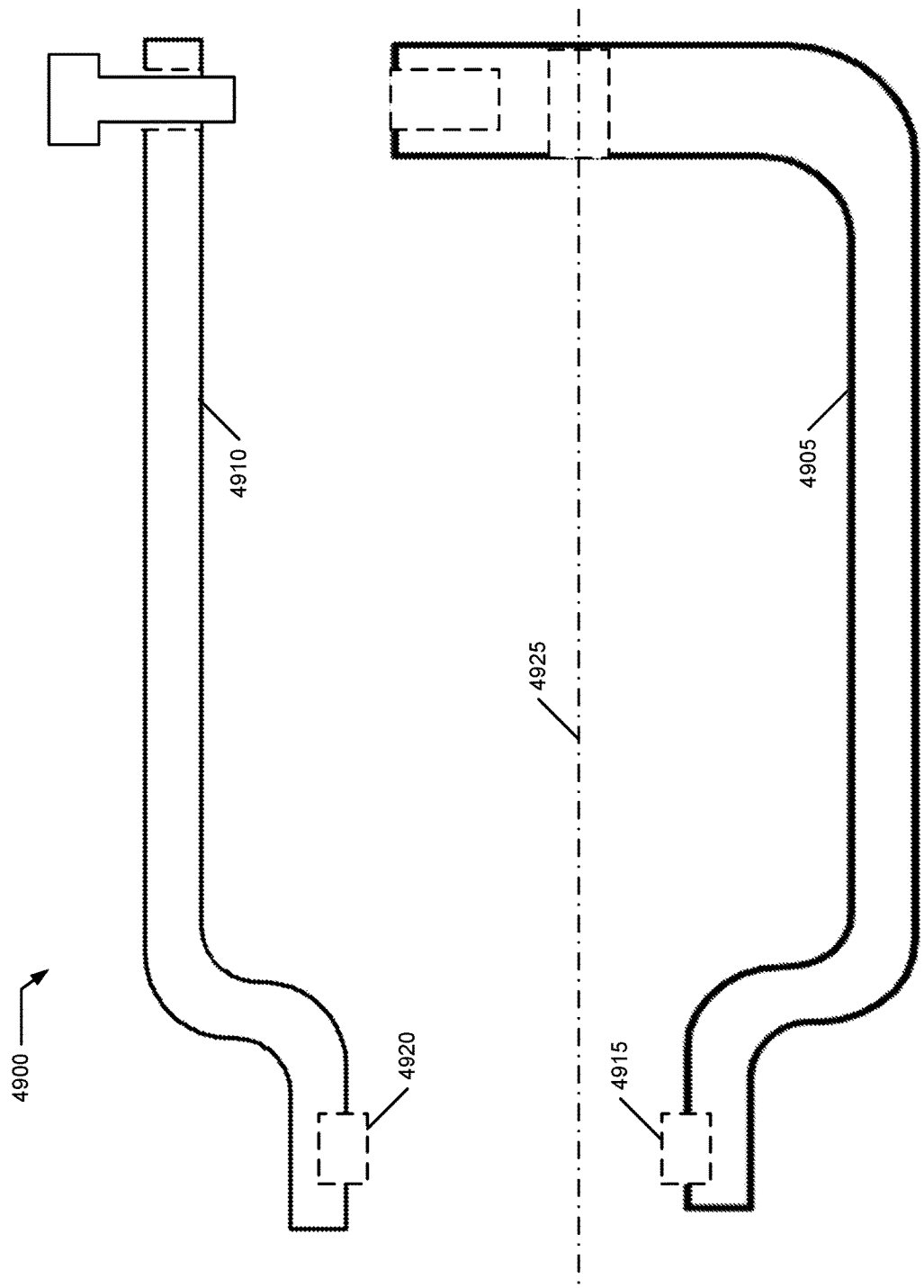

FIG. 49 illustrates an alternative clamp 4900 for use with prosthetic body 4600 of FIG. 46. As illustrated, clamp 4900 defines an assembly (some embodiments may include a unitary design) having a first arm 4905 and a second arm 4910 that may be joined to first arm 4905 and form a generally U-shaped structure.

First arm 4905 includes a first mating engagement structure 4915 and second arm 4910 includes a second mating engagement structure 4920. These structures are compatible and complementary to the appropriate grip structures (including element(s) 4605) on body 4600. As noted herein, when the grip structures include an extending element, the corresponding compatible and complementary mating engagement structure may include a conforming cavity. When the grip structures include an indenting element, the corresponding compatible and complementary mating engagement structure may include an extending structure.

Depths, perimeter shapes, and other mechanical coupling parameters are compatible for corresponding element and mating structures.

Clamp 4900 includes a clamp centerline 4925 that is designed to be co-axial with centerline 2115 of body 4600. In some embodiments described herein, engagement systems may have included an adapter to maintain an axis of the installable head aligned with these centerlines.

Some embodiments may not include this optional adapter. For example, in some instances, installable head may be "self-centering" such that an application of the aligned assembly forces by the alignment of the centerlines during installation causes installable head to automatically align and achieve the desired orientation relative to body 4600. Thus some embodiments may include, and some embodiments may exclude, such an adapter for the installable head.

Figure 50:
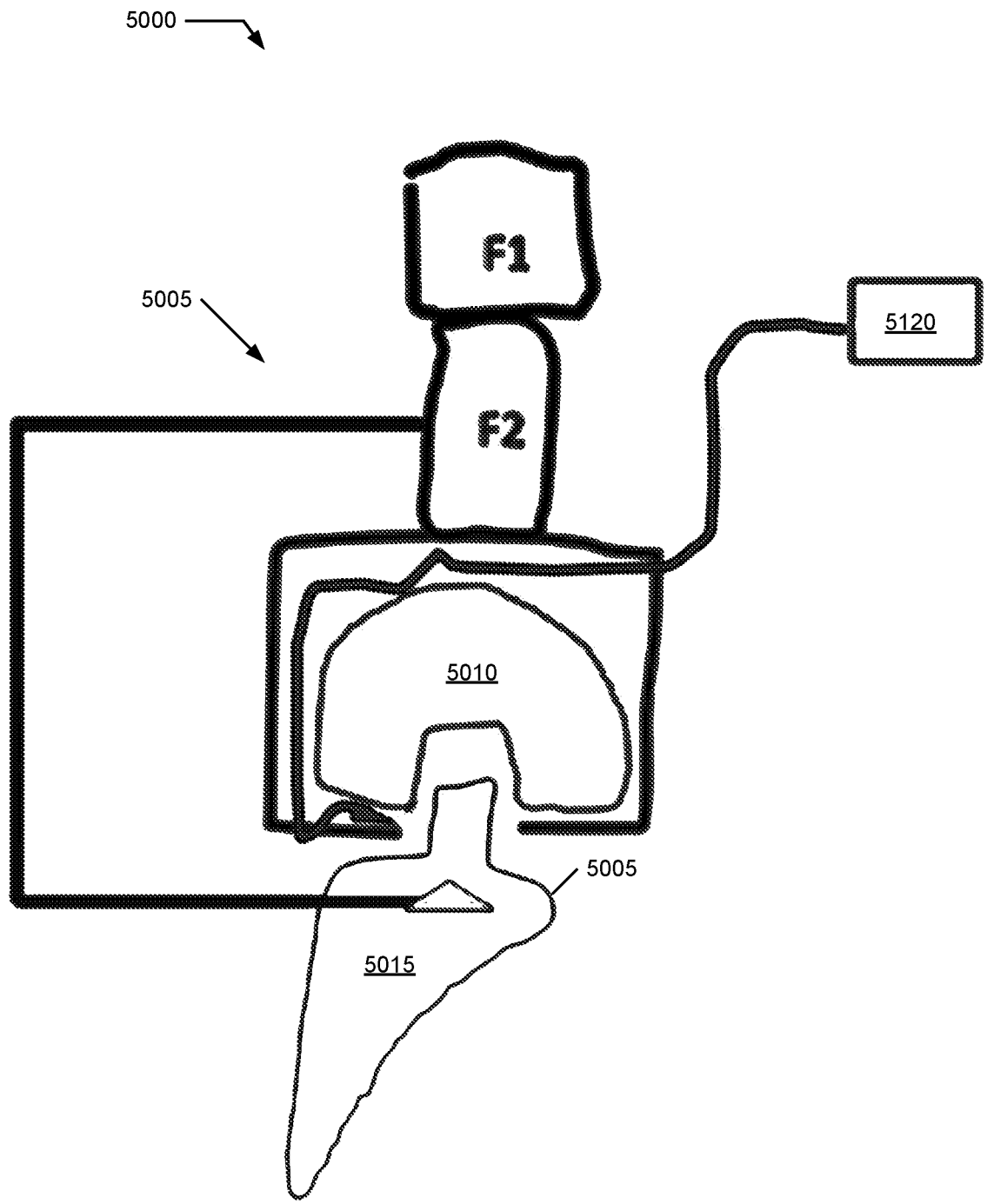
FIG. 50-FIG. 52 illustrate an embodiment of an enhancement to the assembly systems described herein.
Figure 51:
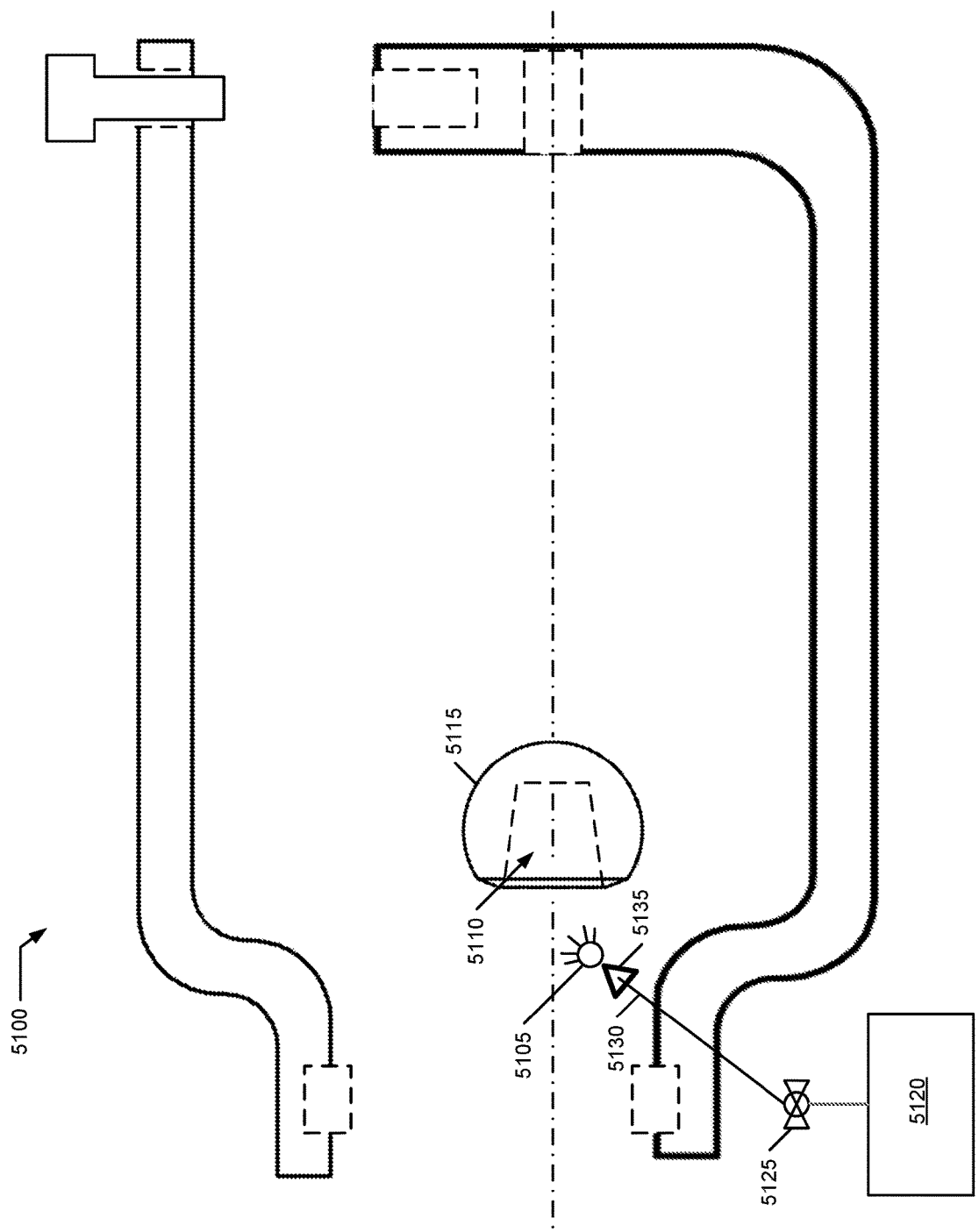
Figure 52:
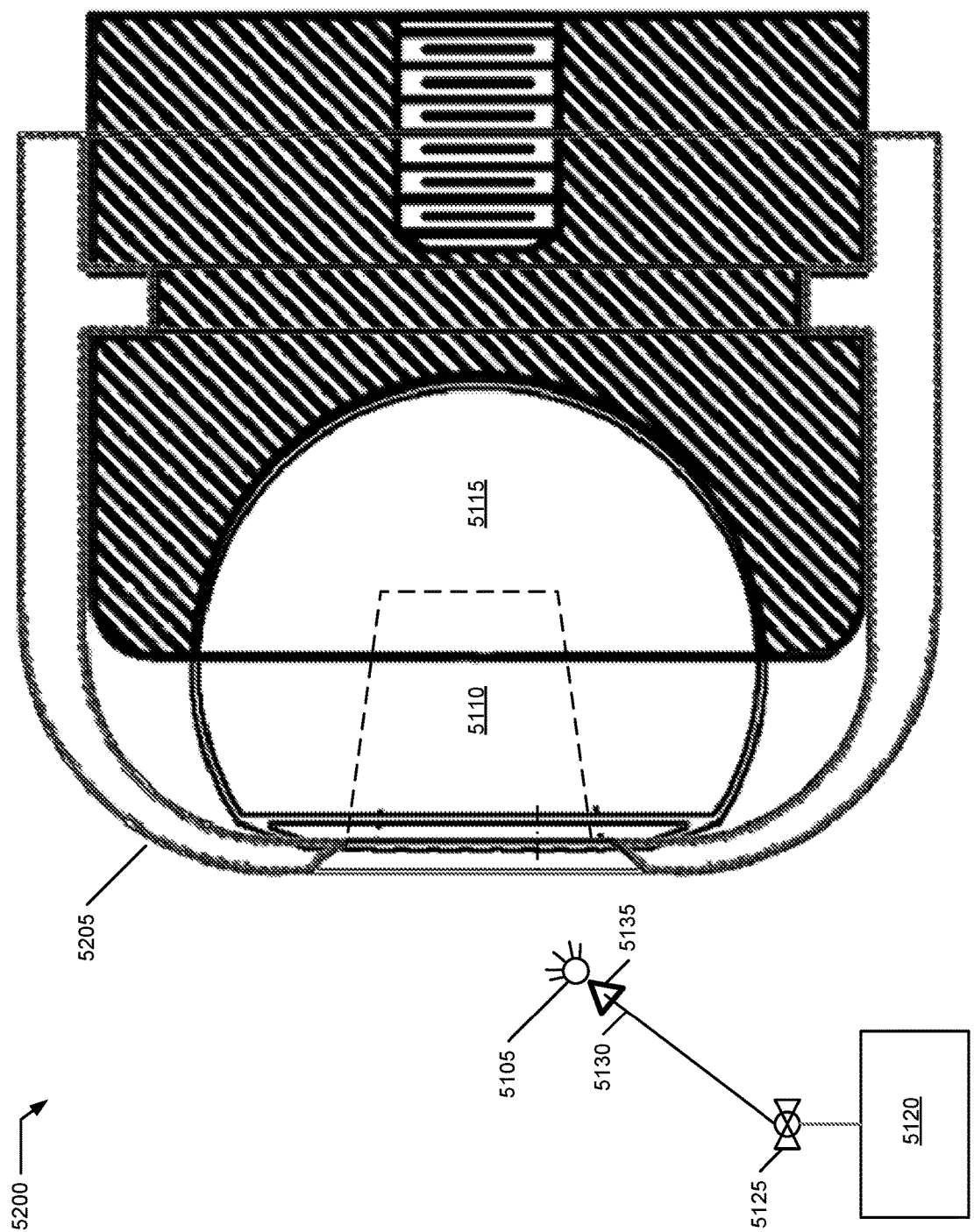

FIG. 50-FIG. 51 illustrate an embodiment of an enhancement to the assembly systems described herein. An embodiment may provide a surgeon with a solution to assure a proper environment (e.g., dry) for the taper assembly. FIG. 50-FIG. 52 illustrate and inclusion of tubes, channels, or the like in or in association with one or more components of the assembly device, for example the clamp, head holder, or other structure, to provide a steady flow of fluid (i.e., gas) to keep the trunnion head taper interface dry and free of contaminants during the taper impaction process. During actual assembly in an operating room environment, it is sometimes necessary or desirable to remove fluids from the insides of various cavities, such as a cavity of the installable head designed to be mounted to taper 2110. One modality of removing fluids from a cavity is to direct a stream of a safe fluid (e.g., carbon dioxide gas, ambient air, or other gas) into the cavity. The fluid may include a gas exclusively when the desired environment is to dry out the cavity. In some applications, a special liquid (e.g., saline solution or the like) may be desirable when the environment need not be dry, particularly when the liquid may facilitate the mechanical joinder and not adversely affect the patient/procedure.

The embodiments described herein may include one or more discrete or integrated channels having outlet jets directed to the installable head cavity to automatically purge fluid from inside the cavity during assembly of the head onto the taper such as when force is being applied to the prosthesis body and installable head to join them together.

FIG. 50 illustrates a generic fluid injection system 5000 for use with a modular assembly tool 5005, examples of which are described herein. Tool 5005 mechanically joins installable head 5010 to prosthesis body 5015 by various force application and transfer modalities. For example, tool 5005 may include a force generator 5020 coupled to a force applicator 5025 that coaxially applies joinder forces to head 5010 to assemble head 5010 onto body 5015. As noted herein, tool 5005 may include an optional head holder 5030 to further aid in alignment of the various relevant axes (e.g., force application, body, and head).

In some instances, body 5015 is installed into living bone first and then head 5010 is joined onto body 5015. There may be various contaminants present during this joining process which may interfere with assembly, joinder, cold-welding, and the like. It may be desirable to aid the surgeon in assembly and improve a quality of the final result by purging the contaminants from the cavity, taper, and the like during the assembly process.

An embodiment of the present invention may include use of a fluid jet system that includes a reservoir 5035 for holding a desired purging fluid, one or more channels, tubes, conveyance structures, and other devices 5040 for communicating the desired purging fluid to the cavity/taper area, and a nozzle, aperture, or jet 5045 proximate the cavity/taper during assembly to direct the desired purging fluid to the appropriate locations.

FIG. 51 illustrates a fluid jet system 5100 directing a fluid 5105 (e.g., a gas) into a cavity 5110 of the installable prosthetic head 5115. An irrigation system for providing fluid 5105 may be implemented in several ways, including a pressurized fluid reservoir 5120 including the irrigating fluid 5105, a valve 5125 controlling a flow of fluid 5105 in one or more channels 5130, each channel may terminate in a nozzle 5135 directed towards head 5115.

Preferably one or more channels 5130 are coupled to and/or integrated with one or more arms of the clamp. Valve 5125 may be manually operated or automatically synchronized with application of an installation force to head 5115.

FIG. 52 illustrates an alternative fluid jet system 5200 for directing fluid 5105 into cavity 5110 of installable prosthetic head 5115. System 5200, similar to system 5100, illustrates an alternative irrigation system for use when optional adapter 5205 is used to secure and align head 5115 to the centerlines. In addition, or in lieu of, channels 5130 being coupled to the clamp, one or more channels 5130 may be coupled to adapter 5205. In practice these may be very small channels or adapters and there may be many ways to provide the fluid directing channels and nozzles to maintain a desired stream of desired fluid into cavity 5110 during assembly of head 5115 onto taper 2110.

In addition to the use of a fluid, FIG. 50 also illustrates use of a realtime interface-force evaluation system. This evaluation system uses a first force F1 (which may be measured or known a priori) from force applicator 5020 and transfers that to a joinder force that assembles head 5010 onto body 5015. Forcer applicator 5025 evaluates interface parameters (which may include measurement of force, velocity, acceleration of one or more interface elements or combinations of such elements), such as a magnitude of a second force F2 and compares that to the first force F1—it may further include first and second derivatives related to interface element motions and accelerations, and characterizations of a response of head/body to the first force. In some cases, among other uses, the realtime interface-force evaluation system enables an operator to understand when the head/body interface has produced a cold weld. For example, this may be indicated when F2 is within a predetermined threshold of F1. There may be many different ways to implement such an evaluation system, for example, U.S. patent application Ser. No. 15/716,533 filed on 27 Sep. 2017, further discusses details of a realtime interface-force system which may be used for this purpose, the contents of this patent application are hereby expressly incorporated by reference thereto in their entireties for all purposes.

Further, such a realtime interface-force evaluation system may advantageously be used with smart tool robot 4500, e.g., a 3D sculptor, an ultrasonic machining tool, robotic tool, or the like, in which realtime response evaluations of a processing element, for example during operation on bone or other tissue, to applied force(s) may allow additional insight into the bone or tissue. For example, this additional insight may inform subsequent processing, such as installation of an implant, an elasticity constant of the bone/tissue, a recommended or optimum size of the implant relative to the installation site, or other information. The incorporated patent application Ser. No. 15/716,533 filed on the same day referenced herein further discusses details of a realtime interface-force system which may be used for this purpose.

Figure 53:
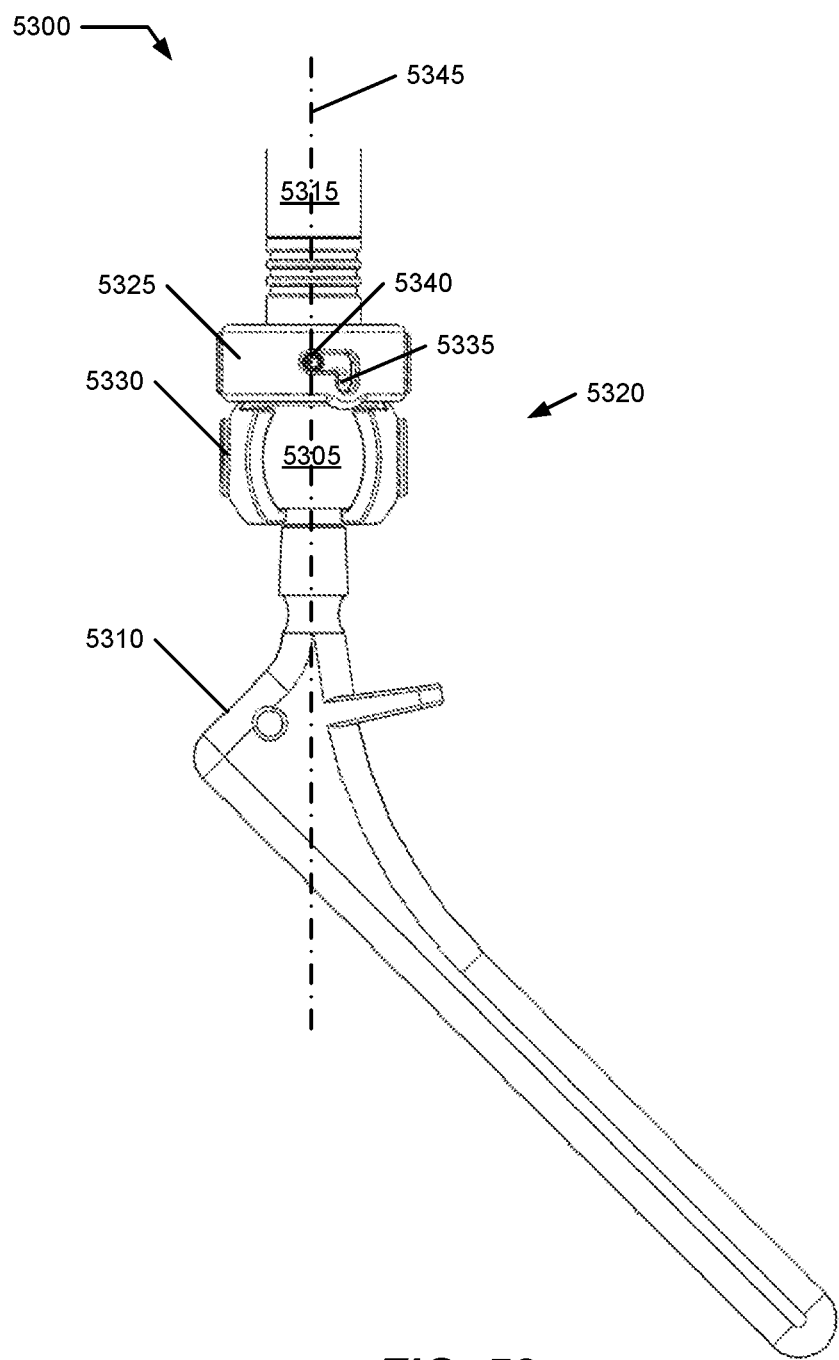
FIG. 53 illustrates an additional embodiment for a trunnion head holding system.
Figure 54:
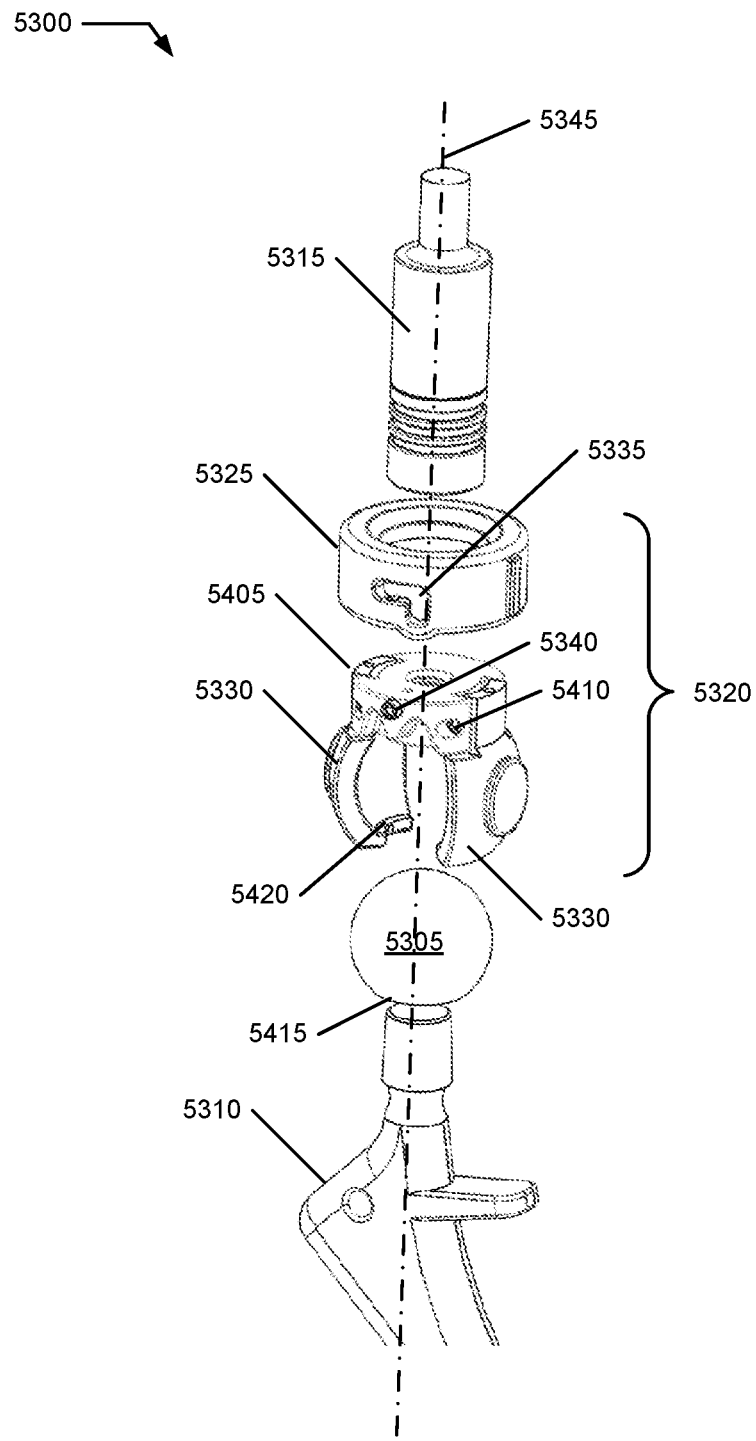
FIG. 54 illustrates an exploded view of the trunnion head holding system of FIG. 53.
Figure 55:
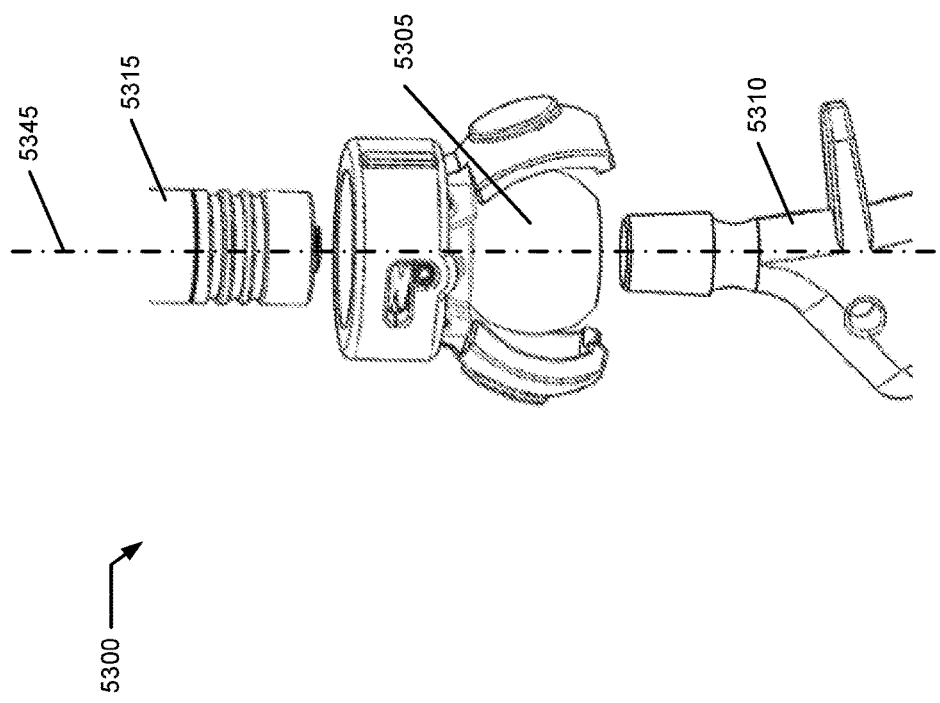
FIG. 55 illustrates a detailed view of the trunnion head holding system of FIG. 53 in an open/disengaged mode.
Figure 56:
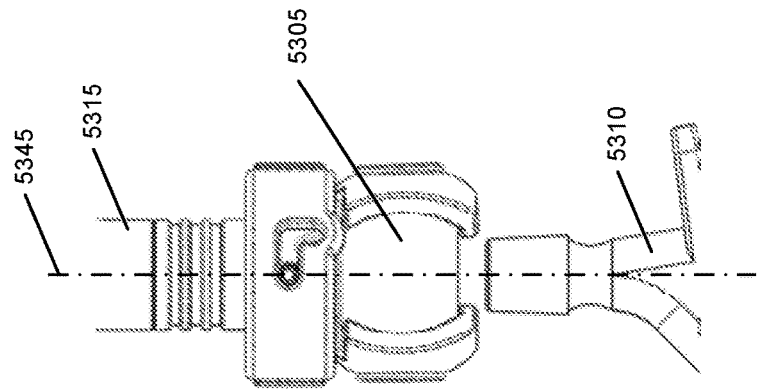
FIG. 56 illustrates a detailed view of the trunnion head holding system of FIG. 53 in a closed/engaged mode.

FIG. 53 illustrates an additional embodiment for a representative trunnion head holding system 5300 and FIG. 54 illustrates an exploded view of the trunnion head holding system of FIG. 53. FIG. 55 illustrates a detailed view of the trunnion head holding system 5300 in an open/disengaged mode and FIG. 56 illustrates a detailed view of the trunnion head holding system 5300 in a closed/engaged mode. As illustrated, system 5300 is configured to precisely align and install a femoral head 5305 onto a femoral stem 5310 by use of a force applied to a force applicator 5315. System 5300 reduces and/or eliminates off-axis force application during installation of head 5305 onto stem 5310 as discussed herein.

System 5300 includes a head holder 5320 that secures and aligns a trunnion cavity of femoral ball 5305 with force applicator 5315 while concurrently aligning the trunnion cavity with a trunnion shaft of femoral stem 5310 such as described herein.

Head holder 5320 has an assembly that includes a lock ring 5325 coupled to two or more pivoting clamp elements 5330. One or more lock ring slot guides 5335 interact with a lock ring guide 5340 to set a mode for clamp elements 5330. Clamp elements 5330 include portions of a spherical cavity that are complementary to a portion of femoral ball 5305 that allow clamp elements 5330 to close onto femoral ball 5305 to engage it and to open for engagement/disengagement with/from femoral ball 5305. Rotation and operation of lock ring 5325 about a clamp top 5405 that is coupled to pivoting clamp elements 5330 about a set of pivots 5410.

Guide 5335 has a vertical portion and a vertical portion— the vertical portion allows ring 5325 to shift up (e.g., FIG. 55) which in turn disengages from pivoting clamp elements 5330 and allows them to swing open about pivots 5410 to release femoral ball 5305. Shifting ring 5325 down (FIG. 56) and rotating guide laterally locks ring 5325 over the closed pivoting clamp elements 5330.

Femoral ball 5305 includes a flat face portion 5415 about an opening for receipt of the trunnion of stem 5310. Each clamp element 5330 includes a ledge 5420 around a bottom portion that is complementary and matching to flat face portion 5415 that aligns the opening with an axis 5345 that aligns an opening of femoral ball 5305 to the trunnion of stem 5310 and force applicator 5315.

FIG. 57 illustrates a detailed view of an embodiment for an additional representative trunnion head holding system 5700 an addition of a fluid system to trunnion head system 5300 as illustrated in FIG. 55 and FIG. 58 illustrates a detailed view of system 5700 with addition of fluid system to the trunnion head system illustrated in FIG. 56.

The fluid system may be implemented in a number of ways to direct a stream of fluid (e.g., a gas, liquid, composite fluid stream) during a joining assembly of femoral ball 5305 onto an exposed morse taper 5710 of stem 5310 as taper 5710 into a bore 5805. A flow tube 5715 is coupled to a modified lock ring 5720. A modification for lock ring 5720 may include an annular flow channel 5810 inside lock ring 5720 coupled to flow tube 5715. Channel 5810 is communicated to a set of fluid channels 5815 that are provided in modified pivoting clamp elements 5725 to exit the fluid stream from a channel port 5730 in each clamp element 5725.

Alternatives may include use of a "Y" tube assembly can input fluid directly into each pivoting clamp element 5725 which is coupled to fluid channels 5815 of each pivoting clamp element 5725 or use of the "Y" tube assembly to direct fluid to a set of external channels coupled to external exit ports and direct fluid onto morse taper 5710.

Fluid, such as $CO_2$, provided from a reservoir an air conditioning function for dispersion and direction of the fluid as needed or desired, such as onto the exposed morse taper of a trunnion as it is being inserted into a cavity into a component of the modular prosthesis. This helps to clean and/or maintain the morse taper dry and contaminant-free during the process of assembling the prosthesis. Foreign material and/or misalignment during assembly as noted may contribute to problems of use of the prosthesis with a patient.

The embodiment illustrated in FIG. 53-FIG. 58 detail a specific implementation of a head holder for alignment of a cavity axis of the trunnion head with an axis of a force applicator. In some implementations, a clamp system as described herein coupled to the head holder will align the axes of the head cavity and the force application with an axis of the trunnion/morse taper. In this way the three axes are all aligned when force is applied by the applicator to mechanically join the head to the morse taper.

The system and methods above has been described in general terms as an aid to understanding details of preferred embodiments of the present invention. In the description herein, numerous specific details are provided, such as examples of components and/or methods, to provide a thorough understanding of embodiments of the present invention. Some features and benefits of the present invention are realized in such modes and are not required in every case. One skilled in the relevant art will recognize, however, that an embodiment of the invention can be practiced without one or more of the specific details, or with other apparatus, systems, assemblies, methods, components, materials, parts, and/or the like. In other instances, well-known structures, materials, or operations are not specifically shown or described in detail to avoid obscuring aspects of embodiments of the present invention.

Reference throughout this specification to "one embodiment", "an embodiment", or "a specific embodiment" means that a particular feature, structure, or characteristic described in connection with the embodiment is included in at least one embodiment of the present invention and not necessarily in all embodiments. Thus, respective appearances of the phrases "in one embodiment", "in an embodiment", or "in a specific embodiment" in various places throughout this specification are not necessarily referring to the same embodiment. Furthermore, the particular features, structures, or characteristics of any specific embodiment of the present invention may be combined in any suitable manner with one or more other embodiments. It is to be understood that other variations and modifications of the embodiments of the present invention described and illustrated herein are possible in light of the teachings herein and are to be considered as part of the spirit and scope of the present invention.

It will also be appreciated that one or more of the elements depicted in the drawings/figures can also be implemented in a more separated or integrated manner, or even removed or rendered as inoperable in certain cases, as is useful in accordance with a particular application.

Additionally, any signal arrows in the drawings/Figures should be considered only as exemplary, and not limiting, unless otherwise specifically noted. Combinations of components or steps will also be considered as being noted, where terminology is foreseen as rendering the ability to separate or combine is unclear.

The foregoing description of illustrated embodiments of the present invention, including what is described in the Abstract, is not intended to be exhaustive or to limit the invention to the precise forms disclosed herein. While specific embodiments of, and examples for, the invention are described herein for illustrative purposes only, various equivalent modifications are possible within the spirit and scope of the present invention, as those skilled in the relevant art will recognize and appreciate. As indicated, these modifications may be made to the present invention in light of the foregoing description of illustrated embodiments of the present invention and are to be included within the spirit and scope of the present invention.

Thus, while the present invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the present invention. It is intended that the invention not be limited to the particular terms used in following claims and/or to the particular embodiment disclosed as the best mode contemplated for carrying out this invention, but that the invention will include any and all embodiments and equivalents falling within the scope of the appended claims. Thus, the scope of the invention is to be determined solely by the appended claims.

What is claimed as new and desired to be protected by Letters Patent of the United States is:

1. A grasper for a head of a modular prosthesis having an opening to a bore complementary to a morse taper of a complementary trunnion of the modular prosthesis, the head including a planar face centered on the opening and a bore axis centered through the opening and aligned with the morse taper, comprising:
    a set of two or more pivoting gripping elements, each gripping element defining a portion of a spherical cavity disposed between a first edge and a second edge with said second edge defining a ledge complementary to a portion of the planar face when the head is disposed within said portion of said spherical cavity;
    a clamp top rotatively coupled to said first edge of each said gripping element and defining a longitudinal clamp axis; and
    a locking mechanism, coupled to said clamp top and operatively coupled to said set of pivoting gripping elements, said locking mechanism configured to secure said pivoting locking members in either a first mode or a second mode, said first mode configured to permit said set of pivoting gripping members to pivot about said clamp top to open and close and said second mode configured to secure said set of pivoting gripping members in a closed position while inhibiting said set of pivoting gripping members from transitioning to an opened position, said closed position configured to align an axis of said spherical cavity with said longitudinal clamp axis responsive to a collective interaction of said ledges with the planar face when the head is disposed within all said portions of said spherical cavity;
    wherein said locking mechanism includes a lock ring that includes two positions, a locked position that engages with said set of pivoting gripping elements to inhibit their transition and an unlocked position that disengages from said set of pivoting gripping elements to permit their transition.

2. The grasper of claim 1 further comprising a fluid conditioning system configured to direct and emit a quantity of fluid from a set of one or more fluid emitters proximate to said second edges, said fluid conditioning system configured for fluid communication with a fluid reservoir.

3. The grasper of claim 2 wherein said fluid conditioning system includes a set of one or more fluid ports communicated to said fluid reservoir and a set of one or more fluid conduits coupled to said set of fluid ports and to said set of fluid emitters.

4. The grasper of claim 3 wherein said lock ring includes a set of one or more annular fluid channels, wherein said set of pivoting gripping elements include a set of one or more element fluid channels, and wherein said set of fluid conduits include said sets of fluid channels.

5. A grasper for a head of a modular prosthesis having an opening to a bore complementary to a morse taper of a complementary trunnion of the modular prosthesis, the head including a planar face centered on the opening and a bore axis centered through the opening and aligned with the morse taper, comprising:
    a set of two or more pivoting gripping elements, each gripping element defining a portion of a spherical cavity disposed between a first edge and a second edge with said second edge defining a ledge complementary to a portion of the planar face when the head is disposed within said portion of said spherical cavity;
    a clamp top rotatively coupled to said first edge of each said gripping element and defining a longitudinal clamp axis; and
    a locking mechanism, coupled to said clamp top and operatively coupled to said set of pivoting gripping elements, said locking mechanism configured to secure said pivoting locking members in either a first mode or a second mode, said first mode configured to permit said set of pivoting gripping members to pivot about said clamp top to open and close and said second mode configured to secure said set of pivoting gripping members in a closed position while inhibiting said set of pivoting gripping members from transitioning to an opened position, said closed position configured to align an axis of said spherical cavity with said longitudinal clamp axis responsive to a collective interaction of said ledges with the planar face when the head is disposed within all said portions of said spherical cavity;
    further comprising a fluid conditioning system configured to direct and emit a quantity of fluid from a set of one or more fluid emitters proximate to said second edges, said fluid conditioning system configured for fluid communication with a fluid reservoir.

6. The grasper of claim 5 wherein said fluid conditioning system includes a set of one or more fluid ports communicated to said fluid reservoir and a set of one or more fluid conduits coupled to said set of fluid ports and to said set of fluid emitters.

7. The grasper of claim 5 wherein the head includes a femoral head and the trunnion is coupled to a femoral stem.

8. The grasper of claim 5 wherein the head includes a humeral head and the trunnion is coupled to a humeral stem.

* * * * *